(12) United States Patent
Banet et al.

(10) Patent No.: US 9,173,594 B2
(45) Date of Patent: Nov. 3, 2015

(54) BODY-WORN MONITOR FOR MEASURING RESPIRATORY RATE

(75) Inventors: Matt Banet, Kihei, HI (US); Marshal Dhillon, San Diego, CA (US); Devin McCombie, San Diego, CA (US)

(73) Assignee: SOTERA WIRELESS, INC., San Diego, CA (US)

( * ) Notice: Subject to any disclaimer, the term of this patent is extended or adjusted under 35 U.S.C. 154(b) by 935 days.

(21) Appl. No.: 12/762,925

(22) Filed: Apr. 19, 2010

(65) Prior Publication Data

US 2011/0257551 A1   Oct. 20, 2011

(51) Int. Cl.
| | |
|---|---|
| *A61B 5/08* | (2006.01) |
| *A61B 5/0205* | (2006.01) |
| *A61B 5/021* | (2006.01) |
| *A61B 5/0245* | (2006.01) |
| *A61B 5/113* | (2006.01) |
| *A61B 5/00* | (2006.01) |

(52) U.S. Cl.
CPC ............. *A61B 5/0816* (2013.01); *A61B 5/0809* (2013.01); *A61B 5/0205* (2013.01); *A61B 5/0245* (2013.01); *A61B 5/02125* (2013.01); *A61B 5/1135* (2013.01); *A61B 5/7239* (2013.01)

(58) Field of Classification Search
CPC combination set(s) only.
See application file for complete search history.

(56) References Cited

U.S. PATENT DOCUMENTS

| | | | |
|---|---|---|---|
| 3,608,542 A * | 9/1971 | Pacela et al. | 600/536 |
| 4,086,916 A | 5/1978 | Freeman et al. | |
| 4,263,918 A | 4/1981 | Swearingen et al. | |
| 4,270,547 A | 6/1981 | Steffen et al. | |
| 4,305,400 A | 12/1981 | Logan | |
| 4,577,639 A | 3/1986 | Simon et al. | |
| 4,582,068 A | 4/1986 | Phillipps et al. | |
| 4,653,498 A | 3/1987 | New, Jr. et al. | |

(Continued)

FOREIGN PATENT DOCUMENTS

| | | |
|---|---|---|
| EP | 0443267 A1 | 8/1991 |
| GB | 2329250 A | 3/1999 |

(Continued)

OTHER PUBLICATIONS

Measuring Respirational Parameters with a Wearable Bioimpedance Device, Seppa et al. IFMBE Proceedings 17, 2007 (Seppa 2007).*

(Continued)

*Primary Examiner* — Michael Kahelin
*Assistant Examiner* — Mitchell E Alter
(74) *Attorney, Agent, or Firm* — Michael A. Whittaker; Acuity Law Group, P.C.

(57) ABSTRACT

The invention provides a system for measuring respiratory rate (RR) from a patient. The system includes an impedance pneumography (IP) sensor, connected to at least two electrodes, and a processing system that receives and processes signals from the electrodes to measure an IP signal. A motion sensor (e.g. an accelerometer) measures at least one motion signal (e.g. an ACC waveform) describing movement of a portion of the patient's body to which it is attached. The processing system receives the IP and motion signals, and processes them to determine, respectfully, frequency-domain IP and motion spectra. Both spectra are then collectively processed to remove motion components from the IP spectrum and determine RR. For example, during the processing, an algorithm determines motion frequency components from the frequency-domain motion spectrum, and then using a digital filter removes these, or parameters calculated therefrom, from the IP spectrum.

19 Claims, 38 Drawing Sheets

(56) References Cited

U.S. PATENT DOCUMENTS

| | | | |
|---|---|---|---|
| 4,710,164 A | 12/1987 | Levin et al. | |
| 4,722,351 A | 2/1988 | Phillipps et al. | |
| 4,802,486 A | 2/1989 | Goodman et al. | |
| 4,807,638 A | 2/1989 | Sramek | |
| 4,905,697 A | 3/1990 | Heggs et al. | |
| 5,025,791 A | 6/1991 | Niwa | |
| 5,140,990 A | 8/1992 | Jones et al. | |
| 5,190,038 A | 3/1993 | Polson et al. | |
| 5,197,489 A | 3/1993 | Conlan | |
| 5,224,928 A | 7/1993 | Sibalis et al. | |
| 5,247,931 A | 9/1993 | Norwood | |
| 5,289,824 A | 3/1994 | Mills et al. | |
| 5,316,008 A | 5/1994 | Suga et al. | |
| 5,339,818 A | 8/1994 | Baker et al. | |
| 5,448,991 A | 9/1995 | Polson et al. | |
| 5,465,082 A | 11/1995 | Chaco | |
| 5,482,036 A | 1/1996 | Diab et al. | |
| 5,485,838 A | 1/1996 | Ukawa et al. | |
| 5,490,505 A | 2/1996 | Diab et al. | |
| 5,515,858 A | 5/1996 | Myllymaki | |
| 5,517,988 A | 5/1996 | Gerhard | |
| 5,524,637 A | 6/1996 | Erickson | |
| 5,549,650 A | 8/1996 | Bornzin et al. | |
| 5,575,284 A | 11/1996 | Athan et al. | |
| 5,588,427 A | 12/1996 | Tien | |
| 5,593,431 A | 1/1997 | Sheldon | |
| 5,632,272 A | 5/1997 | Diab et al. | |
| 5,645,060 A | 7/1997 | Yorkey | |
| 5,649,543 A | 7/1997 | Hosaka et al. | |
| 5,680,870 A | 10/1997 | Hood et al. | |
| 5,685,299 A | 11/1997 | Diab et al. | |
| 5,709,205 A | 1/1998 | Bukta | |
| 5,743,856 A | 4/1998 | Oka et al. | |
| 5,766,131 A | 6/1998 | Kondo et al. | |
| 5,769,785 A | 6/1998 | Diab et al. | |
| 5,800,349 A | 9/1998 | Isaacson et al. | |
| 5,820,550 A | 10/1998 | Polson et al. | |
| 5,848,373 A | 12/1998 | DeLorme et al. | |
| 5,853,370 A | 12/1998 | Chance et al. | |
| 5,857,975 A | 1/1999 | Golub | |
| 5,865,755 A | 2/1999 | Golub | |
| 5,865,756 A | 2/1999 | Peel, III | |
| 5,873,834 A | 2/1999 | Yanagi et al. | |
| 5,876,353 A | 3/1999 | Riff | |
| 5,895,359 A | 4/1999 | Peel, III | |
| 5,899,855 A | 5/1999 | Brown | |
| 5,913,827 A | 6/1999 | Gorman | |
| 5,919,141 A | 7/1999 | Money et al. | |
| 5,941,836 A | 8/1999 | Friedman | |
| 5,964,701 A | 10/1999 | Asada et al. | |
| 5,964,720 A | 10/1999 | Pelz | |
| 5,971,930 A | 10/1999 | Elghazzawi | |
| 6,002,952 A | 12/1999 | Diab et al. | |
| 6,011,985 A | 1/2000 | Athan et al. | |
| 6,018,673 A | 1/2000 | Chin et al. | |
| 6,036,642 A | 3/2000 | Diab et al. | |
| 6,041,783 A | 3/2000 | Gruenke | |
| 6,057,758 A | 5/2000 | Dempsey et al. | |
| 6,067,462 A | 5/2000 | Diab et al. | |
| 6,081,735 A | 6/2000 | Diab et al. | |
| 6,081,742 A * | 6/2000 | Amano et al. | 600/513 |
| 6,094,592 A | 7/2000 | Yorkey et al. | |
| 6,117,077 A | 9/2000 | Del Mar et al. | |
| 6,129,686 A | 10/2000 | Friedman | |
| 6,157,850 A | 12/2000 | Diab et al. | |
| 6,159,147 A | 12/2000 | Lichter et al. | |
| 6,160,478 A | 12/2000 | Jacobsen et al. | |
| 6,168,569 B1 | 1/2001 | McEwen et al. | |
| 6,198,394 B1 | 3/2001 | Jacobsen et al. | |
| 6,198,951 B1 | 3/2001 | Kosuda et al. | |
| 6,199,550 B1 | 3/2001 | Wiesmann et al. | |
| 6,206,830 B1 | 3/2001 | Diab et al. | |
| 6,236,872 B1 * | 5/2001 | Diab et al. | 600/323 |
| 6,251,080 B1 | 6/2001 | Henkin et al. | |
| 6,261,247 B1 | 7/2001 | Ishikawa et al. | |
| 6,262,769 B1 | 7/2001 | Anderson et al. | |
| 6,263,222 B1 | 7/2001 | Diab et al. | |
| 6,287,262 B1 | 9/2001 | Amano et al. | |
| 6,334,065 B1 | 12/2001 | Al-Ali et al. | |
| 6,371,921 B1 | 4/2002 | Caro et al. | |
| 6,388,240 B2 | 5/2002 | Schulz et al. | |
| RE37,852 E | 9/2002 | Aso et al. | |
| 6,443,890 B1 | 9/2002 | Schulze et al. | |
| 6,480,729 B2 | 11/2002 | Stone | |
| 6,491,647 B1 | 12/2002 | Bridger et al. | |
| 6,503,206 B1 | 1/2003 | Li et al. | |
| 6,516,289 B2 | 2/2003 | David | |
| 6,526,310 B1 | 2/2003 | Carter et al. | |
| 6,527,729 B1 | 3/2003 | Turcott | |
| 6,533,729 B1 | 3/2003 | Khair et al. | |
| 6,541,756 B2 | 4/2003 | Schulz et al. | |
| 6,544,173 B2 | 4/2003 | West et al. | |
| 6,544,174 B2 | 4/2003 | West et al. | |
| 6,546,267 B1 | 4/2003 | Sugiura et al. | |
| 6,551,252 B2 | 4/2003 | Sackner et al. | |
| 6,584,336 B1 | 6/2003 | Ali et al. | |
| 6,589,170 B1 | 7/2003 | Flach et al. | |
| 6,595,929 B2 | 7/2003 | Stivoric et al. | |
| 6,605,038 B1 | 8/2003 | Teller et al. | |
| 6,606,993 B1 | 8/2003 | Wiesmann et al. | |
| 6,616,606 B1 | 9/2003 | Petersen et al. | |
| 6,650,917 B2 | 11/2003 | Diab et al. | |
| 6,684,090 B2 | 1/2004 | Ali et al. | |
| 6,694,177 B2 | 2/2004 | Eggers et al. | |
| 6,699,194 B1 | 3/2004 | Diab et al. | |
| 6,732,064 B1 | 5/2004 | Kadtke et al. | |
| 6,745,060 B2 | 6/2004 | Diab et al. | |
| 6,770,028 B1 | 8/2004 | Ali et al. | |
| 6,790,178 B1 | 9/2004 | Mault et al. | |
| 6,811,538 B2 | 11/2004 | Westbrook et al. | |
| 6,845,256 B2 | 1/2005 | Chin et al. | |
| 6,850,787 B2 | 2/2005 | Weber et al. | |
| 6,879,850 B2 | 4/2005 | Kimball | |
| 6,893,396 B2 | 5/2005 | Schulze et al. | |
| 6,912,414 B2 * | 6/2005 | Tong | 600/372 |
| 6,934,571 B2 | 8/2005 | Wiesmann et al. | |
| 6,947,781 B2 | 9/2005 | Asada et al. | |
| 6,976,958 B2 | 12/2005 | Quy | |
| 6,985,078 B2 | 1/2006 | Suzuki et al. | |
| 6,997,882 B1 | 2/2006 | Parker et al. | |
| 7,020,508 B2 | 3/2006 | Stivoric et al. | |
| 7,020,578 B2 | 3/2006 | Sorensen et al. | |
| 7,029,447 B2 | 4/2006 | Rantala | |
| 7,041,060 B2 | 5/2006 | Flaherty et al. | |
| 7,048,687 B1 | 5/2006 | Reuss et al. | |
| 7,079,888 B2 | 7/2006 | Oung et al. | |
| 7,115,824 B2 | 10/2006 | Lo | |
| 7,156,809 B2 | 1/2007 | Quy | |
| 7,184,809 B1 | 2/2007 | Sterling et al. | |
| 7,186,966 B2 | 3/2007 | Al-Ali | |
| 7,194,293 B2 | 3/2007 | Baker, Jr. | |
| 7,215,984 B2 | 5/2007 | Diab et al. | |
| 7,215,987 B1 | 5/2007 | Sterling et al. | |
| 7,225,007 B2 | 5/2007 | Al-Ali et al. | |
| 7,241,265 B2 | 7/2007 | Cummings et al. | |
| 7,257,438 B2 | 8/2007 | Kinast | |
| 7,296,312 B2 | 11/2007 | Menkedick et al. | |
| 7,299,159 B2 | 11/2007 | Nanikashvili | |
| 7,301,451 B2 | 11/2007 | Hastings | |
| 7,314,451 B2 | 1/2008 | Halperin et al. | |
| 7,351,206 B2 | 4/2008 | Suzuki et al. | |
| 7,355,512 B1 | 4/2008 | Al-Ali | |
| 7,373,191 B2 | 5/2008 | DeLonzor et al. | |
| 7,373,912 B2 | 5/2008 | Self et al. | |
| 7,377,794 B2 | 5/2008 | Al-Ali et al. | |
| 7,382,247 B2 | 6/2008 | Welch et al. | |
| 7,383,069 B2 | 6/2008 | Ruchti et al. | |
| 7,383,070 B2 | 6/2008 | Diab et al. | |
| 7,384,398 B2 | 6/2008 | Gagnadre et al. | |
| 7,400,919 B2 | 7/2008 | Petersen et al. | |
| 7,420,472 B2 | 9/2008 | Tran | |
| 7,427,926 B2 | 9/2008 | Sinclair et al. | |
| 7,455,643 B1 | 11/2008 | Li et al. | |
| 7,468,036 B1 | 12/2008 | Rulkov et al. | |

(56) References Cited

U.S. PATENT DOCUMENTS

| | | |
|---|---|---|
| 7,477,143 B2 | 1/2009 | Albert |
| 7,479,890 B2 | 1/2009 | Lehrman et al. |
| 7,485,095 B2 | 2/2009 | Shusterman |
| 7,502,643 B2 | 3/2009 | Farringdon et al. |
| 7,508,307 B2 | 3/2009 | Albert |
| 7,509,131 B2 | 3/2009 | Krumm et al. |
| 7,509,154 B2 | 3/2009 | Diab et al. |
| 7,522,035 B2 | 4/2009 | Albert |
| 7,530,949 B2 | 5/2009 | Al-Ali et al. |
| 7,539,532 B2 | 5/2009 | Tran |
| 7,541,939 B2 | 6/2009 | Zadesky et al. |
| 7,542,878 B2 | 6/2009 | Nanikashvili |
| 7,586,418 B2 | 9/2009 | Cuddihy et al. |
| 7,598,878 B2 | 10/2009 | Goldreich |
| 7,602,301 B1 | 10/2009 | Stirling et al. |
| 7,616,110 B2 | 11/2009 | Crump et al. |
| 7,625,344 B1 | 12/2009 | Brady et al. |
| 7,628,071 B2 | 12/2009 | Sasaki et al. |
| 7,628,730 B1 | 12/2009 | Watterson et al. |
| 7,641,614 B2 | 1/2010 | Asada et al. |
| 7,648,463 B1 | 1/2010 | Elhag et al. |
| 7,656,287 B2 | 2/2010 | Albert et al. |
| 7,668,588 B2 | 2/2010 | Kovacs |
| 7,670,295 B2 | 3/2010 | Sackner et al. |
| 7,674,230 B2 | 3/2010 | Reisfeld |
| 7,674,231 B2 | 3/2010 | McCombie et al. |
| 7,678,061 B2 | 3/2010 | Lee et al. |
| 7,684,954 B2 | 3/2010 | Shahabdeen et al. |
| 7,689,437 B1 | 3/2010 | Teller et al. |
| 7,698,101 B2 | 4/2010 | Alten et al. |
| 7,698,830 B2 | 4/2010 | Townsend et al. |
| 7,698,941 B2 | 4/2010 | Sasaki et al. |
| 7,715,984 B2 | 5/2010 | Ramakrishnan et al. |
| 7,725,147 B2 | 5/2010 | Li et al. |
| 7,782,189 B2 | 8/2010 | Spoonhower et al. |
| 7,827,011 B2 | 11/2010 | DeVaul et al. |
| 7,976,480 B2 | 7/2011 | Grajales et al. |
| 7,983,933 B2 | 7/2011 | Karkanias et al. |
| 8,047,998 B2 | 11/2011 | Kolluri et al. |
| 8,082,160 B2 | 12/2011 | Collins, Jr. et al. |
| 8,137,270 B2 * | 3/2012 | Keenan et al. ................ 600/301 |
| 8,167,800 B2 | 5/2012 | Ouchi et al. |
| 2001/0004234 A1 | 6/2001 | Petelenz et al. |
| 2001/0013826 A1 | 8/2001 | Ahmed et al. |
| 2001/0045395 A1 | 11/2001 | Kitaevich et al. |
| 2002/0013517 A1 | 1/2002 | West et al. |
| 2002/0032386 A1 | 3/2002 | Sackner et al. |
| 2002/0072859 A1 | 6/2002 | Kajimoto et al. |
| 2002/0151805 A1 | 10/2002 | Sugo et al. |
| 2002/0156354 A1 | 10/2002 | Larson |
| 2002/0170193 A1 | 11/2002 | Townsend et al. |
| 2002/0193671 A1 | 12/2002 | Ciurczak et al. |
| 2002/0193692 A1 | 12/2002 | Inukai et al. |
| 2002/0198679 A1 | 12/2002 | Victor et al. |
| 2003/0004420 A1 | 1/2003 | Narimatsu |
| 2003/0097046 A1 | 5/2003 | Sakamaki et al. |
| 2003/0130590 A1 | 7/2003 | Bui et al. |
| 2003/0135099 A1 | 7/2003 | Al-Ali |
| 2003/0153836 A1 | 8/2003 | Gagnadre et al. |
| 2003/0158699 A1 | 8/2003 | Townsend et al. |
| 2003/0167012 A1 | 9/2003 | Friedman et al. |
| 2003/0171662 A1 | 9/2003 | O'Connor et al. |
| 2003/0181815 A1 | 9/2003 | Ebner et al. |
| 2003/0208335 A1 | 11/2003 | Unuma et al. |
| 2004/0019288 A1 | 1/2004 | Kinast |
| 2004/0030261 A1 | 2/2004 | Rantala |
| 2004/0034293 A1 | 2/2004 | Kimball |
| 2004/0034294 A1 | 2/2004 | Kimball et al. |
| 2004/0054821 A1 | 3/2004 | Warren et al. |
| 2004/0073128 A1 | 4/2004 | Hatlestad et al. |
| 2004/0077934 A1 | 4/2004 | Massad |
| 2004/0111033 A1 | 6/2004 | Oung et al. |
| 2004/0122315 A1 | 6/2004 | Krill |
| 2004/0133079 A1 | 7/2004 | Mazar et al. |
| 2004/0162466 A1 | 8/2004 | Quy |
| 2004/0162493 A1 | 8/2004 | Mills |
| 2004/0193063 A1 | 9/2004 | Kimura et al. |
| 2004/0225207 A1 | 11/2004 | Bae et al. |
| 2004/0267099 A1 | 12/2004 | McMahon et al. |
| 2005/0027205 A1 | 2/2005 | Tarassenko et al. |
| 2005/0043598 A1 | 2/2005 | Goode, Jr. et al. |
| 2005/0059870 A1 | 3/2005 | Aceti |
| 2005/0070773 A1 | 3/2005 | Chin et al. |
| 2005/0113107 A1 | 5/2005 | Meunier |
| 2005/0113703 A1 | 5/2005 | Farringdon et al. |
| 2005/0119586 A1 | 6/2005 | Coyle et al. |
| 2005/0124866 A1 | 6/2005 | Elaz et al. |
| 2005/0124903 A1 | 6/2005 | Roteliuk et al. |
| 2005/0149350 A1 | 7/2005 | Kerr et al. |
| 2005/0171444 A1 | 8/2005 | Ono et al. |
| 2005/0187796 A1 | 8/2005 | Rosenfeld et al. |
| 2005/0206518 A1 | 9/2005 | Welch et al. |
| 2005/0209511 A1 | 9/2005 | Heruth et al. |
| 2005/0228296 A1 | 10/2005 | Banet |
| 2005/0228298 A1 | 10/2005 | Banet et al. |
| 2005/0228301 A1 | 10/2005 | Banet et al. |
| 2005/0234317 A1 | 10/2005 | Kiani |
| 2005/0240087 A1 | 10/2005 | Keenan et al. |
| 2005/0261565 A1 | 11/2005 | Lane et al. |
| 2005/0261593 A1 | 11/2005 | Zhang et al. |
| 2005/0265267 A1 | 12/2005 | Hwang |
| 2005/0283088 A1 | 12/2005 | Bernstein |
| 2006/0036141 A1 | 2/2006 | Kamath et al. |
| 2006/0047215 A1 | 3/2006 | Newman et al. |
| 2006/0074321 A1 | 4/2006 | Kouchi et al. |
| 2006/0074322 A1 | 4/2006 | Nitzan |
| 2006/0122469 A1 | 6/2006 | Martel |
| 2006/0128263 A1 | 6/2006 | Baird |
| 2006/0142648 A1 | 6/2006 | Banet et al. |
| 2006/0155589 A1 | 7/2006 | Lane et al. |
| 2006/0178591 A1 | 8/2006 | Hempfling |
| 2006/0200029 A1 | 9/2006 | Evans et al. |
| 2006/0252999 A1 | 11/2006 | Devaul et al. |
| 2006/0265246 A1 | 11/2006 | Hoag |
| 2006/0270949 A1 | 11/2006 | Mathie et al. |
| 2006/0271404 A1 | 11/2006 | Brown |
| 2006/0281979 A1 | 12/2006 | Kim et al. |
| 2007/0010719 A1 | 1/2007 | Huster et al. |
| 2007/0055163 A1 | 3/2007 | Asada et al. |
| 2007/0066910 A1 | 3/2007 | Inukai et al. |
| 2007/0071643 A1 | 3/2007 | Hall et al. |
| 2007/0094045 A1 | 4/2007 | Cobbs et al. |
| 2007/0118056 A1 | 5/2007 | Wang et al. |
| 2007/0129769 A1 | 6/2007 | Bourget et al. |
| 2007/0142715 A1 | 6/2007 | Banet et al. |
| 2007/0142730 A1 | 6/2007 | Laermer et al. |
| 2007/0156456 A1 | 7/2007 | McGillin et al. |
| 2007/0161912 A1 | 7/2007 | Zhang et al. |
| 2007/0185393 A1 | 8/2007 | Zhou et al. |
| 2007/0188323 A1 | 8/2007 | Sinclair et al. |
| 2007/0193834 A1 | 8/2007 | Pai et al. |
| 2007/0208233 A1 | 9/2007 | Kovacs |
| 2007/0232867 A1 | 10/2007 | Hansmann |
| 2007/0237719 A1 | 10/2007 | Jones et al. |
| 2007/0244376 A1 | 10/2007 | Wang |
| 2007/0250261 A1 | 10/2007 | Soehren |
| 2007/0252853 A1 | 11/2007 | Park et al. |
| 2007/0255116 A1 | 11/2007 | Mehta et al. |
| 2007/0260487 A1 | 11/2007 | Bartfeld et al. |
| 2007/0265533 A1 | 11/2007 | Tran |
| 2007/0265880 A1 | 11/2007 | Bartfeld et al. |
| 2007/0270671 A1 | 11/2007 | Gal |
| 2007/0276261 A1 | 11/2007 | Banet et al. |
| 2007/0282208 A1 | 12/2007 | Jacobs et al. |
| 2007/0287386 A1 | 12/2007 | Agrawal et al. |
| 2007/0293770 A1 | 12/2007 | Bour et al. |
| 2007/0293781 A1 | 12/2007 | Sims et al. |
| 2008/0004500 A1 | 1/2008 | Cazares et al. |
| 2008/0004507 A1 | 1/2008 | Williams, Jr. et al. |
| 2008/0004904 A1 | 1/2008 | Tran |
| 2008/0027341 A1 | 1/2008 | Sackner et al. |
| 2008/0039731 A1 | 2/2008 | McCombie et al. |
| 2008/0077026 A1 | 3/2008 | Banet et al. |
| 2008/0077027 A1 | 3/2008 | Allgeyer |

(56) References Cited

U.S. PATENT DOCUMENTS

| | | |
|---|---|---|
| 2008/0082001 A1 | 4/2008 | Hatlestad et al. |
| 2008/0101160 A1 | 5/2008 | Besson |
| 2008/0103405 A1 | 5/2008 | Banet et al. |
| 2008/0114220 A1 | 5/2008 | Banet et al. |
| 2008/0132106 A1 | 6/2008 | Burnes et al. |
| 2008/0139955 A1 | 6/2008 | Hansmann et al. |
| 2008/0146887 A1 | 6/2008 | Rao et al. |
| 2008/0146892 A1 | 6/2008 | LeBoeuf et al. |
| 2008/0161707 A1 | 7/2008 | Farringdon et al. |
| 2008/0162496 A1 | 7/2008 | Postrel |
| 2008/0167535 A1 | 7/2008 | Stivoric et al. |
| 2008/0171927 A1 | 7/2008 | Yang et al. |
| 2008/0194918 A1 | 8/2008 | Kulik et al. |
| 2008/0195735 A1 | 8/2008 | Hodges et al. |
| 2008/0204254 A1 | 8/2008 | Kazuno |
| 2008/0208013 A1 | 8/2008 | Zhang et al. |
| 2008/0208273 A1 | 8/2008 | Owen et al. |
| 2008/0214963 A1 | 9/2008 | Guillemaud et al. |
| 2008/0221399 A1 | 9/2008 | Zhou et al. |
| 2008/0221404 A1 | 9/2008 | Tso |
| 2008/0262362 A1 | 10/2008 | Kolluri et al. |
| 2008/0275349 A1 | 11/2008 | Halperin et al. |
| 2008/0281168 A1 | 11/2008 | Gibson et al. |
| 2008/0281310 A1 | 11/2008 | Dunning et al. |
| 2008/0287751 A1 | 11/2008 | Stivoric et al. |
| 2008/0294019 A1 | 11/2008 | Tran |
| 2008/0319282 A1 | 12/2008 | Tran |
| 2008/0319327 A1 | 12/2008 | Banet et al. |
| 2009/0018408 A1 | 1/2009 | Ouchi et al. |
| 2009/0018409 A1 | 1/2009 | Banet et al. |
| 2009/0018453 A1 | 1/2009 | Banet et al. |
| 2009/0040041 A1 | 2/2009 | Janetis et al. |
| 2009/0054752 A1 | 2/2009 | Jonnalagadda et al. |
| 2009/0069642 A1 | 3/2009 | Gao et al. |
| 2009/0076363 A1 | 3/2009 | Bly et al. |
| 2009/0076397 A1 | 3/2009 | Libbus et al. |
| 2009/0076398 A1 | 3/2009 | Li et al. |
| 2009/0076405 A1 | 3/2009 | Amurthur et al. |
| 2009/0082681 A1 | 3/2009 | Yokoyama et al. |
| 2009/0112281 A1 | 4/2009 | Miyazawa et al. |
| 2009/0112630 A1 | 4/2009 | Collins, Jr. et al. |
| 2009/0118590 A1 | 5/2009 | Teller et al. |
| 2009/0118626 A1* | 5/2009 | Moon et al. ......... 600/484 |
| 2009/0131759 A1 | 5/2009 | Sims et al. |
| 2009/0187085 A1 | 7/2009 | Pav |
| 2009/0192366 A1 | 7/2009 | Mensinger et al. |
| 2009/0198139 A1 | 8/2009 | Lewicke et al. |
| 2009/0221937 A1 | 9/2009 | Smith et al. |
| 2009/0222119 A1 | 9/2009 | Plahey et al. |
| 2009/0227877 A1 | 9/2009 | Tran |
| 2009/0233770 A1 | 9/2009 | Vincent et al. |
| 2009/0259113 A1 | 10/2009 | Liu et al. |
| 2009/0262074 A1 | 10/2009 | Nasiri et al. |
| 2009/0264712 A1 | 10/2009 | Baldus et al. |
| 2009/0287067 A1 | 11/2009 | Dorogusker et al. |
| 2009/0295541 A1 | 12/2009 | Roof |
| 2009/0306485 A1 | 12/2009 | Bell |
| 2009/0306487 A1 | 12/2009 | Crowe et al. |
| 2009/0306524 A1 | 12/2009 | Muhlsteff et al. |
| 2009/0312973 A1 | 12/2009 | Hatlestad et al. |
| 2009/0318779 A1 | 12/2009 | Tran |
| 2009/0322513 A1 | 12/2009 | Hwang et al. |
| 2010/0010380 A1 | 1/2010 | Panken et al. |
| 2010/0030034 A1* | 2/2010 | Schulhauser et al. ......... 600/301 |
| 2010/0030085 A1 | 2/2010 | Rojas Ojeda et al. |
| 2010/0056881 A1 | 3/2010 | Libbus et al. |
| 2010/0056886 A1 | 3/2010 | Hurtubise et al. |
| 2010/0113948 A1 | 5/2010 | Yang et al. |
| 2010/0125188 A1 | 5/2010 | Schilling et al. |
| 2010/0130811 A1 | 5/2010 | Leuthardt et al. |
| 2010/0160793 A1 | 6/2010 | Lee et al. |
| 2010/0160794 A1 | 6/2010 | Banet et al. |
| 2010/0160795 A1 | 6/2010 | Banet et al. |
| 2010/0160796 A1 | 6/2010 | Banet et al. |
| 2010/0160797 A1 | 6/2010 | Banet et al. |
| 2010/0160798 A1 | 6/2010 | Banet et al. |
| 2010/0168589 A1 | 7/2010 | Banet et al. |
| 2010/0210930 A1 | 8/2010 | Saylor |
| 2010/0217099 A1 | 8/2010 | Leboeuf et al. |
| 2010/0222649 A1 | 9/2010 | Schoenberg |
| 2010/0234693 A1 | 9/2010 | Srinivasan et al. |
| 2010/0234695 A1 | 9/2010 | Morris |
| 2010/0234786 A1 | 9/2010 | Fulkerson et al. |
| 2010/0241011 A1 | 9/2010 | McCombie et al. |
| 2010/0280440 A1 | 11/2010 | Skelton et al. |
| 2010/0298650 A1 | 11/2010 | Moon et al. |
| 2010/0298651 A1 | 11/2010 | Moon et al. |
| 2010/0298652 A1 | 11/2010 | McCombie et al. |
| 2010/0298653 A1 | 11/2010 | McCombie et al. |
| 2010/0298654 A1 | 11/2010 | McCombie et al. |
| 2010/0298655 A1 | 11/2010 | McCombie et al. |
| 2010/0298656 A1 | 11/2010 | McCombie et al. |
| 2010/0298657 A1 | 11/2010 | McCombie et al. |
| 2010/0298658 A1 | 11/2010 | McCombie et al. |
| 2010/0298659 A1 | 11/2010 | McCombie et al. |
| 2010/0298660 A1 | 11/2010 | McCombie et al. |
| 2010/0298661 A1 | 11/2010 | McCombie et al. |
| 2010/0312115 A1 | 12/2010 | Dentinger |
| 2010/0324384 A1 | 12/2010 | Moon et al. |
| 2010/0324385 A1 | 12/2010 | Moon et al. |
| 2010/0324386 A1 | 12/2010 | Moon et al. |
| 2010/0324387 A1 | 12/2010 | Moon et al. |
| 2010/0324388 A1 | 12/2010 | Moon et al. |
| 2010/0324389 A1 | 12/2010 | Moon et al. |
| 2010/0331640 A1 | 12/2010 | Medina |
| 2011/0066006 A1 | 3/2011 | Banet et al. |
| 2011/0066007 A1 | 3/2011 | Banet et al. |
| 2011/0066008 A1 | 3/2011 | Banet et al. |
| 2011/0066009 A1 | 3/2011 | Moon et al. |
| 2011/0066010 A1 | 3/2011 | Moon et al. |
| 2011/0066037 A1 | 3/2011 | Banet et al. |
| 2011/0066038 A1 | 3/2011 | Banet et al. |
| 2011/0066039 A1 | 3/2011 | Banet et al. |
| 2011/0066043 A1 | 3/2011 | Banet et al. |
| 2011/0066044 A1 | 3/2011 | Moon et al. |
| 2011/0066045 A1 | 3/2011 | Moon et al. |
| 2011/0066050 A1 | 3/2011 | Moon et al. |
| 2011/0066051 A1 | 3/2011 | Moon et al. |
| 2011/0066062 A1 | 3/2011 | Banet et al. |
| 2011/0070829 A1 | 3/2011 | Griffin et al. |
| 2011/0076942 A1 | 3/2011 | Taveau et al. |
| 2011/0093281 A1 | 4/2011 | Plummer et al. |
| 2011/0105862 A1 | 5/2011 | Gies et al. |
| 2011/0144456 A1 | 6/2011 | Muhlsteff et al. |
| 2011/0152632 A1 | 6/2011 | Le Neel et al. |
| 2011/0178375 A1 | 7/2011 | Forster |
| 2011/0224498 A1 | 9/2011 | Banet et al. |
| 2011/0224499 A1 | 9/2011 | Banet et al. |
| 2011/0224500 A1 | 9/2011 | Banet et al. |
| 2011/0224506 A1 | 9/2011 | Moon et al. |
| 2011/0224507 A1 | 9/2011 | Banet et al. |
| 2011/0224508 A1 | 9/2011 | Moon |
| 2011/0224556 A1 | 9/2011 | Moon et al. |
| 2011/0224557 A1 | 9/2011 | Banet et al. |
| 2011/0224564 A1 | 9/2011 | Moon et al. |
| 2011/0257489 A1 | 10/2011 | Banet et al. |
| 2011/0257551 A1 | 10/2011 | Banet et al. |
| 2011/0257552 A1 | 10/2011 | Banet et al. |
| 2011/0257554 A1 | 10/2011 | Banet et al. |
| 2011/0257555 A1 | 10/2011 | Banet et al. |
| 2011/0275907 A1 | 11/2011 | Inciardi et al. |
| 2012/0065525 A1 | 3/2012 | Douniama et al. |
| 2012/0123232 A1 | 5/2012 | Najarian et al. |

FOREIGN PATENT DOCUMENTS

| | | |
|---|---|---|
| WO | 9932030 A1 | 7/1999 |
| WO | 2006005169 A1 | 1/2006 |
| WO | 2007024777 A2 | 3/2007 |
| WO | 2007143535 A2 | 12/2007 |
| WO | 2008037820 A1 | 4/2008 |
| WO | 2008110788 A1 | 9/2008 |
| WO | 2010135516 A2 | 11/2010 |
| WO | 2010135518 A1 | 11/2010 |

(56) References Cited

FOREIGN PATENT DOCUMENTS

| WO | 2010148205 A1 | 12/2010 |
|---|---|---|
| WO | 2011032132 A2 | 3/2011 |
| WO | 2011034881 A1 | 3/2011 |
| WO | 2011082341 A1 | 7/2011 |
| WO | 2011112782 A1 | 9/2011 |
| WO | 2011133582 A1 | 10/2011 |

OTHER PUBLICATIONS

Comparison of Impedance and Inductance Ventilation Sensors on Adults During Breathing, Motion and Simulated Airway Obstruction, Cohen et al. IEEE Transactions on Biomedical Engineering, vol. 44, Jul. 1997 (Cohen).*
International Search Report and Written Opinion dated Jul. 22, 2011 issued in PCT/US2011/027843.
International Search Report and Written Opinion dated Jul. 20, 2011 issued in PCT/US2011/033100.
Non-Final Office Action issued by the US Patent and Trademark Office on May 26, 2011 in U.S. Appl. No. 12/469,151.
Response to Non-Final Office Action submitted Nov. 25, 2011 in U.S. Appl. No. 12/469,151.
Notice of Allowance issued by the US Patent and Trademark Office on Feb. 1, 2012 in U.S. Appl. No. 12/469,151.
Non-Final Office Action issued by the US Patent and Trademark Office on Aug. 4, 2011 in U.S. Appl. No. 12/469,182.
Response to Non-Final Office Action submitted Nov. 25, 2011 in U.S. Appl. No. 12/469,182.
Notice of Allowance issued by the US Patent and Trademark Office on Dec. 28, 2011 in U.S. Appl. No. 12/469,182.
International Search Report and Written Opinion dated Oct. 15, 2010 issued in PCT/US2010/035550.
Non-Final Office Action issued by the US Patent and Trademark Office on Apr. 12, 2012 in U.S. Appl. No. 12/559,429.
Non-Final Office Action issued by the US Patent and Trademark Office on Apr. 12, 2012 in U.S. Appl. No. 12/559,430.
Non-Final Office Action issued by the US Patent and Trademark Office on Apr. 24, 2012 in U.S. Appl. No. 12/559,435.
Non-Final Office Action issued by the US Patent and Trademark Office on Apr. 25, 2012 in U.S. Appl. No. 12/762,733.
Non-Final Office Action issued by the US Patent and Trademark Office on Apr. 27, 2012 in U.S. Appl. No. 12/762,822.
Non-Final Office Action issued by the US Patent and Trademark Office on Mar. 27, 2012 in U.S. Appl. No. 12/559,422.
Mathie, Monitoring and Interpreting Human Movement Patterns using a Triaxial Accelerometer. Faculty of Engineering. The University of New South Wales. PhD Dissertation. Aug. 2003: part1 pp. 1-256.
Mathie, Monitoring and Interpreting Human Movement Patterns using a Triaxial Accelerometer. Faculty of Engineering. The University of New South Wales. PhD Dissertation. Aug. 2003: part2 pp. 256-512.
International Search Report and Written Opinion dated Apr. 27, 2012 as reported in PCT/US2011/067441.
Non-Final Office Action issued by the US Patent and Trademark Office on May 7, 2012 in U.S. Appl. No. 12/469,115.
Non-Final Office Action issued by the US Patent and Trademark Office on May 9, 2012 in U.S. Appl. No. 12/762,836.
Non-Final Office Action issued by the US Patent and Trademark Office on May 10, 2012 in U.S. Appl. No. 12/559,419.
Jackson, Digital Filter Design and Synthesis Using High-Level Modeling Tools. Virginia Polytechnic Institute and State University Thesis. Dec. 1999.
Kim et al., Two Algorithms for Detecting Respiratory Rate from ECG Signal. IFMBE Proceedings 2007;14(6) JC27:4069-4071.
O'Haver, Peak Finding and Measurement, Version 1.6 Oct. 26, 2006. http://web.archive.org/web/20090205162604/http://terpconnect.umd.edu/-toh/spectrum/PeakFindingandMeasurement.htm.

Reinvuo et al., Measurement of Respiratory Rate with High-Resolution Accelerometer and EMFit Pressure Sensor. Proceedings of the 2006 IEEE Sensors Applications Symposium Feb. 7-9, 2006:192-195.
Non-Final Office Action issued by the US Patent and Trademark Office on May 11, 2012 in U.S. Appl. No. 12/762,846.
Non-Final Office Action issued by the US Patent and Trademark Office on May 11, 2012 in U.S. Appl. No. 12/762,874.
Non-Final Office Action issued by the US Patent and Trademark Office on Jun. 11, 2012 in U.S. Appl. No. 12/469,222.
Non-Final Office Action issued by the US Patent and Trademark Office on Jun. 8, 2012 in U.S. Appl. No. 12/650,383.
Non-Final Office Action issued by the US Patent and Trademark Office on Jun. 8, 2012 in U.S. Appl. No. 12/650,392.
Non-Final Office Action issued by the US Patent and Trademark Office on Jun. 20, 2012 in U.S. Appl. No. 121762,751.
International Search Report and Written Opinion dated Jun. 29, 2012 issued in PCT/US2012/025640.
Non-Final Office Action issued by the US Patent and Trademark Office on Jul. 5, 2012 in U.S. Appl. No. 12/560,138.
"Signal Strength." Oct. 6, 2008. http://web.archive.org/web/20081006200523/http://!en.wikipedia.org/wiki/Signal_strength.
Non-Final Office Action issued by the US Patent and Trademark Office on May 24, 2012 in U.S. Appl. No. 12/560,111.
Restriction Requirement issued by the US Patent and Trademark Office on Apr. 24, 2012 in U.S. Appl. No. 12/469,107.
Response to Restriction Requirement submitted Jun. 14, 2012 in U.S. Appl. No. 12/469,107.
International Search Report and Written Opinion issued Jul. 20, 2011 in PCT/US2011/033100.
Allen et al., Classification of a known sequence of motions and postures from accelerometry data using adapted Gaussian mixture models. Physiol. Meas. 2006;27:935-951.
Asada et al., Active Noise Cancellation Using MEMS Accelerometers for Motion-Tolerant Wearable Bio-Sensors. Proceedings of the 26th Annual International Conference of the IEEE EMBS. San Francisco, CA, USA. Sep. 1-5, 2004:2157-2160.
Bowers et al., Respiratory Rate Derived from Principal Component Analysis of Single Lead Electrocardiogram. Computers in Cardiology Conference Proceedings Sep. 2008;35:437-440.
Bussmann et al., Measuring daily behavior using ambulatory accelerometry: The Activity Monitor. Behav Res Methods Instrum Comput. Aug. 2003;33(3):349-356.
Cretikos et al., The Objective Medical Emergency Team Activation Criteria: a case-control study. Resuscitation Apr. 2007;73(1):62-72.
Espina et al., Wireless Body Sensor Network for Continuous Cuffless Blood Pressure Monitoring. Proceedings of the 3rd IEEE-EMBS. International Summer School and Symposium on Medical Devices and Biosensors. MIT, Boston, USA, Sep. 4-6, 2006:11-15.
Fieselmann et al., Respiratory rate predicts cardiopulmonary arrest for internal medicine patients. J Gen Intern Med Jul. 1993;8(7):354-360.
Goldhill et al., A physiologically-based early warning score for ward patients: the association between score and outcome. Anaesthesia Jun. 2005;60(6):547-553.
Hung et al., Estimation of Respiratory Waveform Using an Accelerometer. 5th IEEE International Symposium on Biomedical Imaging: From Nano to Macro, May 14-17, 2008:1493-1496.
Jin, A Respiration Monitoring System Based on a Tri-Axial Accelerometer and an Air-Coupled Microphone. Technische Universiteit Eindhoven, University of Technology. Master's Graduation Paper, Electrical Engineering Aug. 25, 2009.
Karantonis et al., Implementation of a Real-Time Human Movement Classifier Using a Triaxial Accelerometer for Ambulatory Monitoring. IEEE Transactions on Information Technology in Biomedicine. Jan. 2006;10(1):156-167.
Khambete et al., Movement artefact rejection in impedance pneumography using six strategically placed electrodes. Physiol. Meas. 2000;21:79-88.
Khan et al., Accelerometer Signal-based Human Activity Recognition Using Augmented Autoregressive Model Coefficients and Arti-

(56) References Cited

OTHER PUBLICATIONS ficial w Neural Nets. 30th Annual International Conference of the IEEE Engineering in Medicine and Biology Society. Aug. 20-24, 2008:5172-5175.
Mason, Signal Processing Methods for Non-Invasive Respiration Monitoring. Department of Engineering Science, University of Oxford 2002.
Mathie et al., Classification of basic daily movements using a triaxial accelerometer. Med Biol Eng Comput. Sep. 2004;42(5):679-687.
Otto et al., System Architecture of a Wireless Body Area Sensor Network for Ubiquitous Health Monitoring. Journal of Mobile Multimedia Jan. 10, 2006;1(4):307-326.
Park et al., an improved algorithm for respiration signal extraction from electrocardiogram measured by conductive textile electrodes using instantaneous frequency estimation. Med Bio Eng Comput 2008;46:147-158.
PDF-Pro for iPhone & iPod touch User Manual. ePapyrus Jul. 2009;1:1-25 http://epapyrus.com/en/files/PDFPro%.
Seo et al., Performance Improvement of Pulse Oximetry-Based Respiration Detection by Selective Mode Bandpass Filtering. Ergonomics and Health Aspects of Work with Computers Lecture Notes in Computer Science, 2007;4566:300-308.
Soh et al., An investigation of respiration while wearing back belts. Applied Ergonomics 1997; 28(3):189-192.
Subbe et al., Effect of introducing the Modified Early Warning score on clinical outcomes, cardiopulmonary arrests and intensive care utilization in acute medical admissions. Anaesthesia Aug. 2003;58(8):797-802.
Vuorela et al., Two portable long-term measurement devices for ECG and bioimpedance. Second International Conference on Pervasive Computing Technologies for Healthcare . . . Jan. 30-Feb. 1, 2008: 169-172.
Wolf et al., Development of a Fall Detector and Classifier based on a Triaxial Accelerometer Demo Board. 2007:210-213.
Non-Final Office Action issued by the US Patent and Trademark Office on Apr. 30, 2012 in U.S. Appl. No. 12/762,790.
Non-Final Office Action issued by the US Patent and Trademark Office on Mar. 30, 2012 in U.S. Appl. No. 12/469,236.
Non-Final Office Action issued by the US Patent and Trademark Office on Apr. 3, 2012 in U.S. Appl. No. 12/469,094.
Restriction Requirement issued by the US Patent and Trademark Office on Feb. 2, 2012 in U.S. Appl. No. 12/469,222.
Non-Final Office Action issued by the US Patent and Trademark Office on Mar. 27, 2012 in U.S. Appl. No. 12/559,426.
Non-Final Office Action issued by the US Patent and Trademark Office on Apr. 3, 2012 in U.S. Appl. No. 12/559,039.
Non-Final Office Action issued by the US Patent and Trademark Office on Dec. 29, 2011 in U.S. Appl. No. 12/559,080.
Response to Non-Final Office Action submitted Mar. 19, 2012 in U.S. Appl. No. 12/559,080.
Notice of Allowance issued by the US Patent and Trademark Office on Apr. 2, 2012 in U.S. Appl. No. 12/559,080.
Non-Final Office Action issued by the US Patent and Trademark Office on Dec. 15, 2011 in U.S. Appl. No. 12/560,077.
Non-Final Office Action issued by the US Patent and Trademark Office on Mar. 8, 2012 in U.S. Appl. No. 12/560,093.
Restriction Requirement issued by the US Patent and Trademark Office on Dec. 14, 2012 in U.S. Appl. No. 12/560,093.
Response to Restriction Requirement submitted Feb. 15, 2012 in U.S. Appl. No. 12/560,093.
Non-Final Office Action issued by the US Patent and Trademark Office on Mar. 1, 2012 in U.S. Appl. No. 12/560,104.
Restriction Requirement issued by the US Patent and Trademark Office on Jan. 19, 2012 in U.S. Appl. No. 12/469,115.
Response to Restriction Requirement submitted Feb. 15, 2012 in U.S. Appl. No. 12/469,115.
Restriction Requirement issued by the US Patent and Trademark Office on Nov. 14, 2011 in U.S. Appl. No. 12/469,127.
Response to Restriction Requirement submitted Feb. 15, 2012 in U.S. Appl. No. 12/469,127.
Non-Final Office Action issued by the US Patent and Trademark Office on Mar. 9, 2012 in U.S. Appl. No. 12/469,127.
Non-Final Office Action issued by the US Patent and Trademark Office on Apr. 3, 2012 in U.S. Appl. No. 12/469,137.
International Preliminary Report on Patentability dated Dec. 1, 2011 issued in PCT/US2010/035554.
International Search Report and Written Opinion dated Sep. 23, 2010 issued in PCT/US2010/035554.
International Preliminary Report on Patentability dated Jan. 5, 2012 issued in PCT/US2010/039000.
International Search Report and Written Opinion dated Sep. 7, 2010 issued in PCT/US2010/039000.
International Search Report and Written Opinion dated Nov. 3, 2010 issued in PCT/US2010/048729.
International Search Report and Written Opinion dated Nov. 5, 2010 issued in PCT/US2010/048866.
International Search Report and Written Opinion dated Mar. 3, 2011 issued in PCT/US2010/062564.
Non-Final Office Action issued by the US Patent and Trademark Office on Jul. 18, 2012 in U.S. Appl. No. 12/650,389.
Chan et al., Noninvasive and Cuffless Measurements of Blood Pressure for Telemedicine. Proceedings of the 23rd Annual International Conference of the IEEE Engineering in Medicine and Biology Society 2001:3 pages.
Fung, Advisory System for Administration of Phenylephrine Following Spinal Anesthesia for Cesarean Section. Master's Thesis. University of British Columbia 2002: 119 pages.
Liu et al., The Changes in Pulse Transit Time at Specific Cuff Pressures during Inflation and Deflation. Proceedings of the 28th IEEE EMBS Annual International Conference New York City, USA, Aug. 30-Sep. 3, 2006:6404-6405.
Nitzan et al., Effects of External Pressure on Arteries Distal to the Cuff During Sphygmomanometry. IEEE Transactions on Biomedical Engineering, Jun. 2005;52(6):1120-1127.
USB 2.0 Specification Engineering Change Notice. Oct. 20, 2000.
Yan and Zhang, A Novel Calibration Method for Noninvasive Blood Pressure Measurement Using Pulse Transit Time. Proceedings of the 4th IEEE-EMBS International Summer School and Symposium on Medical Devices and Biosensors St Catharine's College, Cambridge, UK, Aug. 19-22, 2007.
Zislin et al., Ways of Improving the Accuracy of Arterial Pressure Oscillometry. Biomedical Engineering 2005;39(4):174-178.
International Search Report and Written Opinion dated May 29, 2012 issued in PCT/US2012/025648.
Non-Final Office Action issued by the US Patent and Trademark Office on Aug. 3, 2012 in U.S. Appl. No. 12/762,925.
Non-Final Office Action issued by the US Patent and Trademark Office on Aug. 3, 2012 in U.S. Appl. No. 12/762,963.
Non-Final Office Action issued by the US Patent and Trademark Office on Aug. 20, 2012 in U.S. Appl. No. 12/762,777.
Non-Final Office Action issued by the US Patent and Trademark Office on Aug. 21, 2012 in U.S. Appl. No. 12/469,107.
Non-Final Office Action issued by the US Patent and Trademark Office on Aug. 24, 2012 in U.S. Appl. No. 12/762,936.
Non Final Office Action issued by the United States Patent and Trademark Office in 12/559,413 on Nov. 9, 2012.
Response to Office Action issued in 12/762,846 dated Nov. 13, 2012.
Response to Office Action issued in 12/762,874 dated Nov. 13, 2012.
Response to Office Action issued in 12/560,111 dated Nov. 26, 2012.
Response to Office Action issued in 11/930,881 dated Nov. 26, 2012.
Final Rejection issued in 12/559,419 on Nov. 16, 2012.
Non Final Office Action issued by the United States Patent and Trademark Office in 12/559,408 on Nov. 23, 2012.
Response to Office Action issued in 12/138,199 dated Nov. 29, 2012.
Response to Office Action issued in 12/650,383 dated Dec. 7, 2012.
Response to Office Action issued in 12/650,392 dated Dec. 7, 2012.
Final Rejection issued by the United States Patent and Trademark Office in 12/559,435 on Dec. 12, 2012.
Final Rejection issued by the United States Patent and Trademark Office in 12/560,111 on Dec. 12, 2012.
Clifford et al., Measuring Tilt with Low-g Accelerometers. Freescale Semiconductor, Inc., 2005:8 pages.

(56) References Cited

OTHER PUBLICATIONS

McKneely et al., Plug-and-Play and Network-Capable Medical Instrumentation and Database with a Complete Healthcare Technology Suite: MediCAN. Joint Workshop on High Confidence Medical Devices, Software, and Systems and Medical Device Plug-and-Play Interoperability. 2007:122-129.

Montgomery et al., Lifeguard—A Personal Physiological Monitor for Extreme Environments. Conf Proc IEEE Eng Med Biol Soc. 2004;3:2192-2195.

Thongpithoonrat et al., Networking and Plug-and-Play of Bedside Medical Instruments. Conf Proc IEEE Eng Med Biol Soc. 2008;2008:1514-1517.

Yang et al., Research on Multi-Parameter Physiological Monitor Based on CAN Bus. IFMBE Proceed. 2008;19:417-419.

Zeltwanger, Controller Area Network and CANopen in Medical Equipment. Bus Briefing: Med Dev Manuf Technol. 2002:34-37.

Zitzmann and Schumann, Interoperable Medical Devices Due to Standardized CANopen Interfaces. Joint Workshop on High Confidence Medical Devices, Software, and Systems and Medical Device Plug-and-Play Interoperability. 2007:97-103.

Non Final Office Action issued by the United States Patent and Trademark Office in 13/432,976 on Dec. 14, 2012.

Final Rejection issued by the United States Patent and Trademark Office in 12/762,733 on Dec. 20, 2012.

Final Rejection issued by the United States Patent and Trademark Office in 12/762,846 on Dec. 20, 2012.

Final Rejection issued by the United States Patent and Trademark Office in 12/650,392 on Jan. 3, 2013.

Final Rejection issued by the United States Patent and Trademark Office in 12/487,283 on Jan. 3, 2013.

Non Final Office Action issued by the United States Patent and Trademark Office in 13/292,923 on Jan. 14, 2013.

Notice of Allowance issued by the United States Patent and Trademark Office in 11/470,708 on Jan. 18, 2013.

International Search Report and Written Opinion issued in PCT/US2012/064302 on Jan. 15, 2013.

Non-Final Office Action issued by the US Patent and Trademark Office on Aug. 30, 2012 in U.S. Appl. No. 12/469,202.

Non-Final Office Action issued by the US Patent and Trademark Office on Aug. 31, 2012 in U.S. Appl. No. 12/469,213.

Non-Final Office Action issued by the US Patent and Trademark Office on Sep. 14, 2012 in U.S. Appl. No. 12/650,374.

Drinnan et al., Relation between heart rate and pulse transit time during paced respiration. Physiol. Meas. Aug. 2001;22(3):425-432.

Flash et al., The Coordination of Arm Movements: An Experimentally Confirmed Mathematical Model. J Neurosci. Jul. 1985;5(7):1688-1703.

Ma and Zhang, A Correlation Study on the Variabilities in Pulse Transit Time, Blood Pressure, and Heart Rate Recorded Simultaneously from Healthy Subjects. Conf Proc IEEE Eng Med Biol Soc. 2005;1:996-999.

Non-Final Office Action issued by the US Patent and Trademark Office on Sep. 17, 2012 in U.S. Appl. No. 12/469,192.

Gallagher, Comparison of Radial and Femoral Arterial Blood Pressure in Children after Cardiopulmonary Bypass. J Clin Monit. Jul. 1985;1(3):168-171.

Park et al., Direct Blood Pressure Measurements in Brachial and Femoral Arteries in Children. Circulation Feb. 1970; 41(2)231-237.

Talkowski, Quantifying Physical Activity in Community Dwelling Older Adults Using Accelerometry. University of Pittsburgh (Dissertation) 2008:1-91.

Non-Final Office Action issued by the US Patent and Trademark Office on Sep. 17, 2012 in U.S. Appl. No. 12/650,354.

Non-Final Office Action issued by the US Patent and Trademark Office on Sep. 21, 2012 in U.S. Appl. No. 12/469,115.

Non-Final Office Action issued by the US Patent and Trademark Office on Sep. 26, 2012 in U.S. Appl. No. 12/560,104.

Packet Definition. The Linux Information Project Jan. 8, 2006 http://www.linfo.org/packet.html.

RS-232. Wikipedia Dec. 5, 2008 http:I/web.archive.org/web/20081205160754/http:/len.wikipedia.org/wiki/RS-232.

Response to Non-Final Office Action issued in U.S. Appl. No. 12/469,236 dated Sep. 27, 2012.

Response to Non-Final Office Action issued in U.S. Appl. No. 12/487,283 dated Sep. 27, 2012.

Non-Final Office Action issued by the US Patent and Trademark Office on Sep. 28, 2012 in U.S. Appl. No. 12/560,087.

Response to Non-Final Office Action issued in U.S. Appl. No. 12/762,836 dated Oct. 9, 2012.

Non-Final Office Action issued by the US Patent and Trademark Office on Oct. 9, 2012 in U.S. Appl. No. 12/762,726.

Response to Non-Final Office Action issued in U.S. Appl. No. 12/559,429 dated Oct. 12, 2012.

Response to Non-Final Office Action issued in U.S. Appl. No. 12/559,430 dated Oct. 12, 2012.

Final Office Action issued by the US Patent and Trademark Office on Oct. 22, 2012 in U.S. Appl. No. 12/762,822.

Response to Non-Final Office Action issued in U.S. Appl. No. 12/559,435 dated Oct. 23, 2012.

Final Office Action issued by the US Patent and Trademark Office on Oct. 24, 2012 in U.S. Appl. No. 12/599,429.

Final Office Action issued by the US Patent and Trademark Office on Oct. 24, 2012 in U.S. Appl. No. 12/599,430.

Non-Final Office Action issued by the US Patent and Trademark Office on Oct. 23, 2012 in U.S. Appl. No. 12/762,944.

Response to Non-Final Office Action issued in U.S. Appl. No. 12/762,733 dated Oct. 25, 2012.

Final Office Action issued by the US Patent and Trademark Office on Oct. 25, 2012 in U.S. Appl. No. 12/599,426.

Alves et al., CAN Protocol: A Laboratory Prototype for Fieldbus Applications. XIX IMEKO World Congress Fundamental and Applied Metrology Sep. 6-11, 2009, Lisbon, Portugal. 4 pages :454-457 ISBN 978-963-88410-0-1.

Benefits of Digital Sensors. Gems Sensors. Feb. 14, 2008. http://web.archive.org/web/20080214122230/http://www.sensorland.com/HowPage054.html.

Final Office Action issued by the US Patent and Trademark Office on Oct. 25, 2012 in U.S. Appl. No. 12/762,790.

Final Office Action issued by the US Patent and Trademark Office on Oct. 26, 2012 in U.S. Appl. No. 12/762,836.

Non-Final Office Action issued by the US Patent and Trademark Office on Oct. 30, 2012 in U.S. Appl. No. 12/559,386.

Non-Final Office Action issued by the US Patent and Trademark Office on Nov. 6, 2012 in U.S. Appl. No. 12/559,379.

Non-Final Office Action issued by the US Patent and Trademark Office on Nov. 6, 2012 in U.S. Appl. No. 12/650,370.

Poon and Zhang, Cuff-Less and Noninvasive Measurements of Arterial Blood Pressure by Pulse Transit Time. Conf Proc IEEE Eng Med Biol Soc. 2005;6:5877-5880.

Non-Final Office Action issued by the US Patent and Trademark Office on Nov. 7, 2012 in U.S. Appl. No. 12/559,392.

Non-Final Office Action issued by the US Patent and Trademark Office on Oct. 24, 2012 in U.S. Appl. No. 12/559,403.

Supplemental European Search Report issued in EP 10778376 dated Jan. 31, 2013.

Final Office Action issued by the United States Patent and Trademark Office in U.S. Appl. No. 12/559,039 dated Feb. 11, 2013.

Reddan et al., Intradialytic Blood Volume Monitoring in Ambulatory Hemodialysis Patients: A Randomized Trial. J Am Soc Nephrol. Jul. 2005;16(7):2162-2169.

Final Office Action issued by the United States Patent and Trademark Office in U.S. Appl. No. 12/469,222 dated Feb. 13, 2013.

Non Final Office Action issued by the United States Patent and Trademark Office in U.S. Appl. No. 12/650,383 dated Feb. 15, 2013.

Non Final Office Action issued by the United States Patent and Trademark Office in U.S. Appl. No. 13/346,408 dated Feb. 25, 2013.

(56) References Cited

OTHER PUBLICATIONS

Final Office Action issued by the United States Patent and Trademark Office in U.S. Appl. No. 12/650,389 dated Mar. 14, 2013.
Klabunde, Mean Arterial Pressure. Cardiovascular Physiology Concepts. Mar. 8, 2007.http://web.archive.org/web/20070308182914/http://www.cvphysiology.com/Blood %20Pressure/BP006.htm.
Final Office Action issued by the United States Patent and Trademark Office in U.S. Appl. No. 12/762,874 dated Mar. 14, 2013.
Non Final Office Action issued by the United States Patent and Trademark Office in U.S. Appl. No. 13/196,326 dated Mar. 22, 2013.
De Scalzi et al., Relationship Between Systolic Time Intervals and Arterial Blood Pressure. Clin Cardiol. 1986;9:545-549.
Ahlstrom et al., Noninvasive investigation of blood pressure changes using the pulse wave transit time: a novel approach in the monitoring of hemodialysis patients. J Artif Organs. 2005;8(3):192-197.
Final Office Action issued by the United States Patent and Trademark Office in U.S. Appl. No. 12/762,751 dated Mar. 29, 2013.

\* cited by examiner

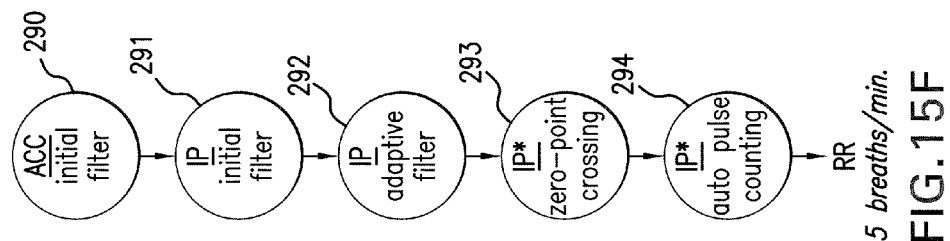
FIG. 15F
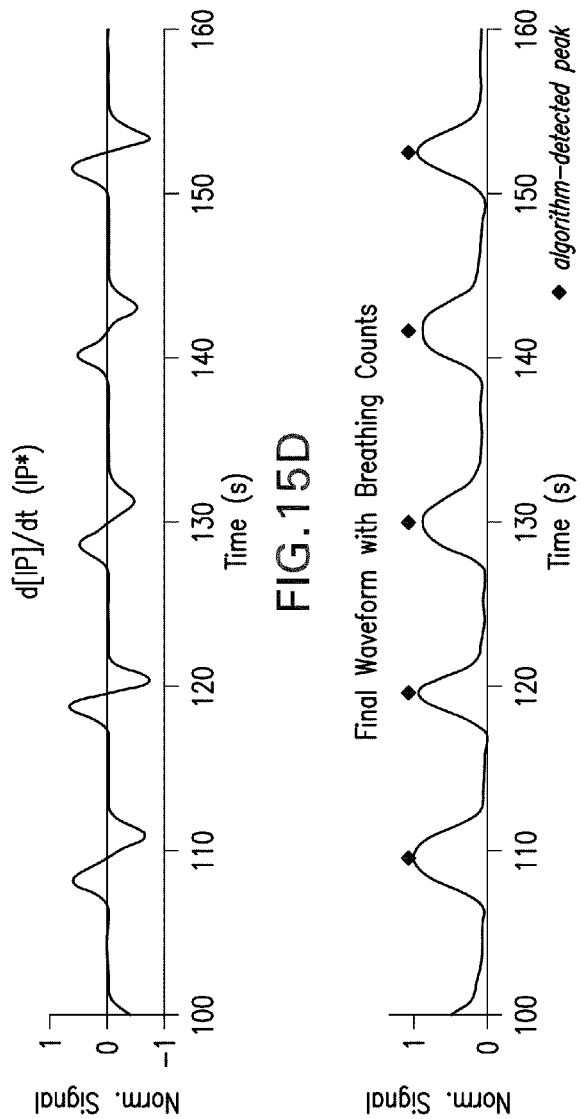
FIG. 15D
FIG. 15E

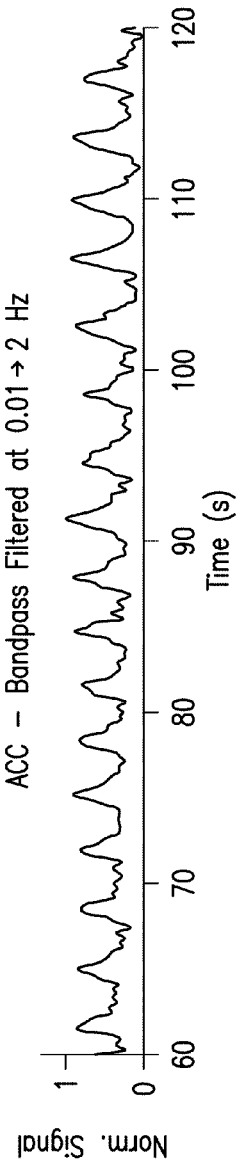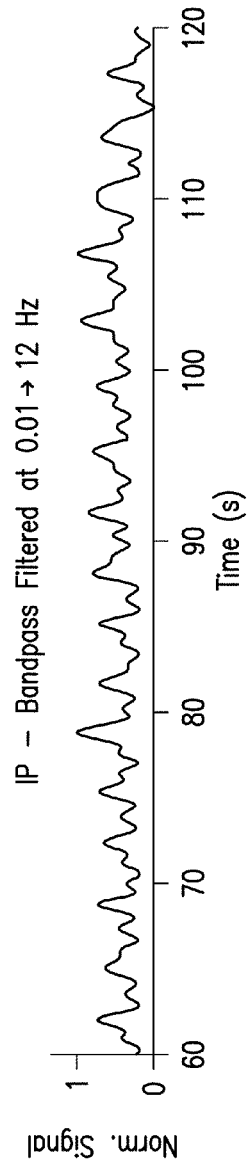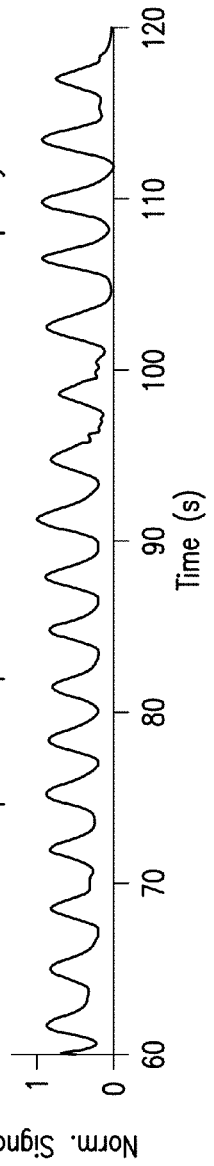

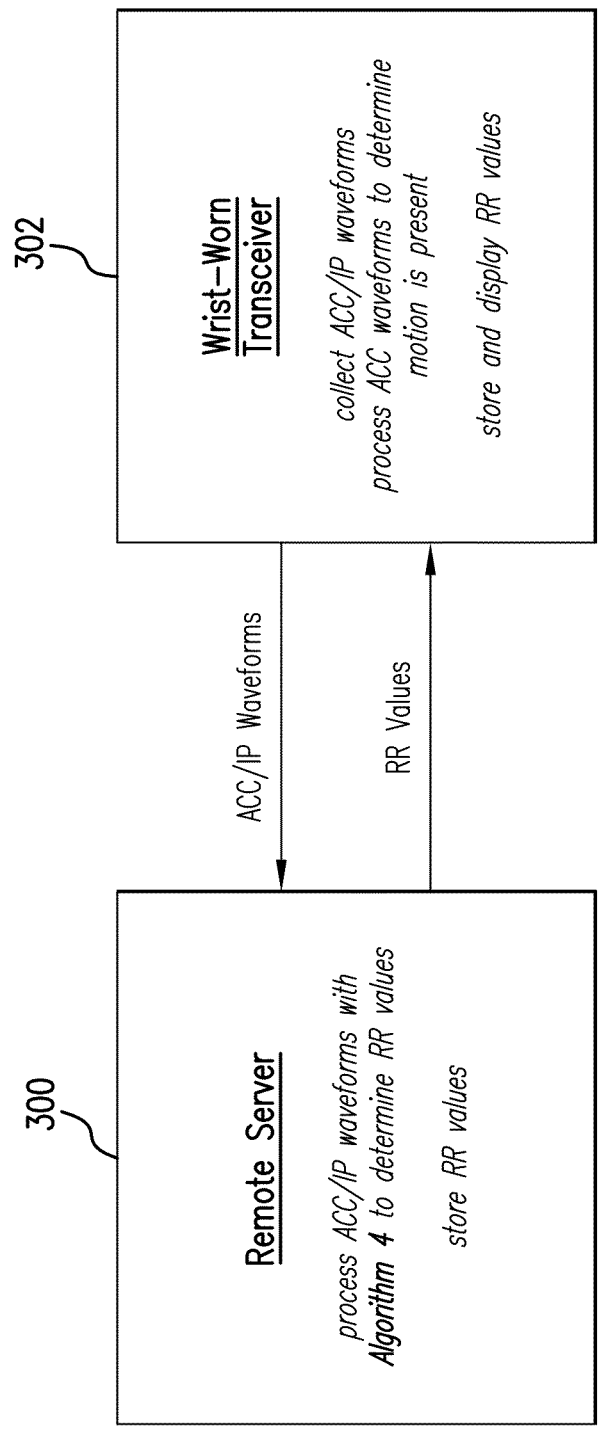

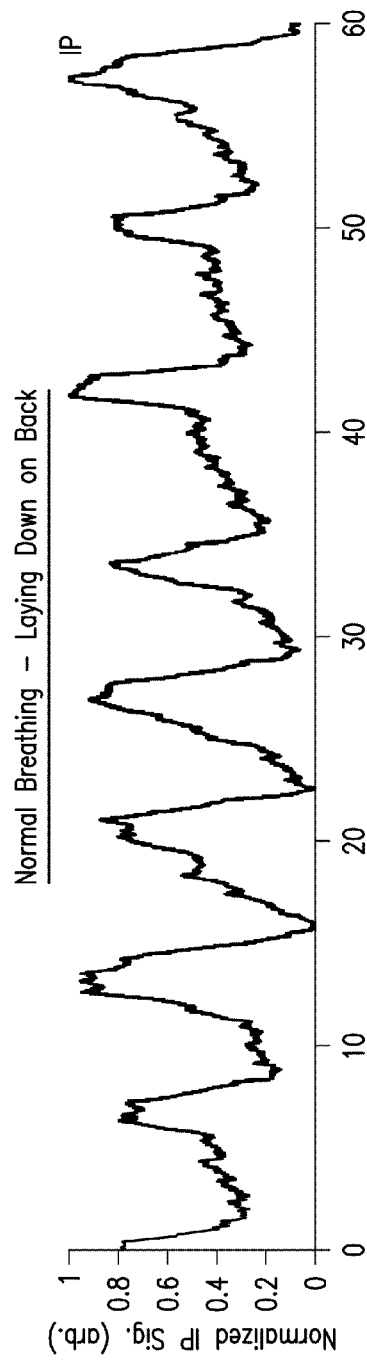
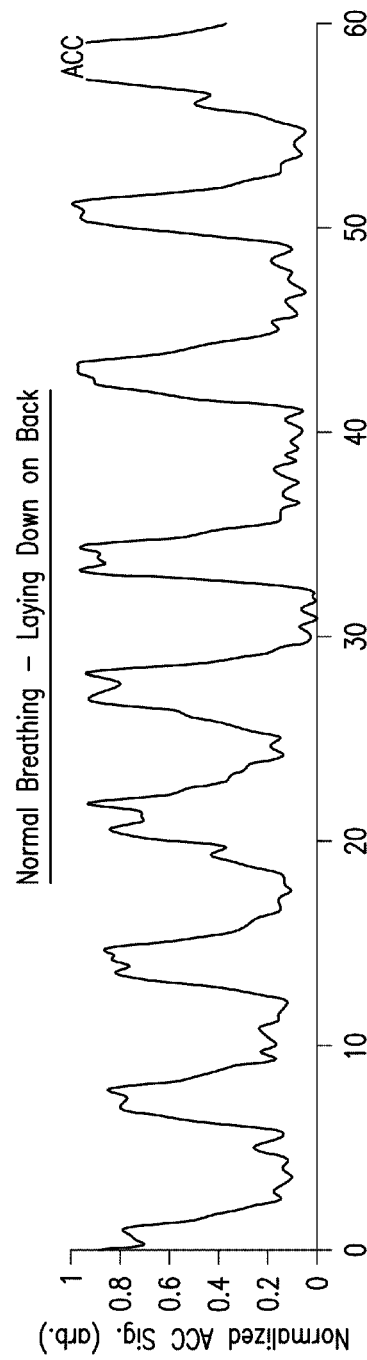
FIG.22A
FIG.22B

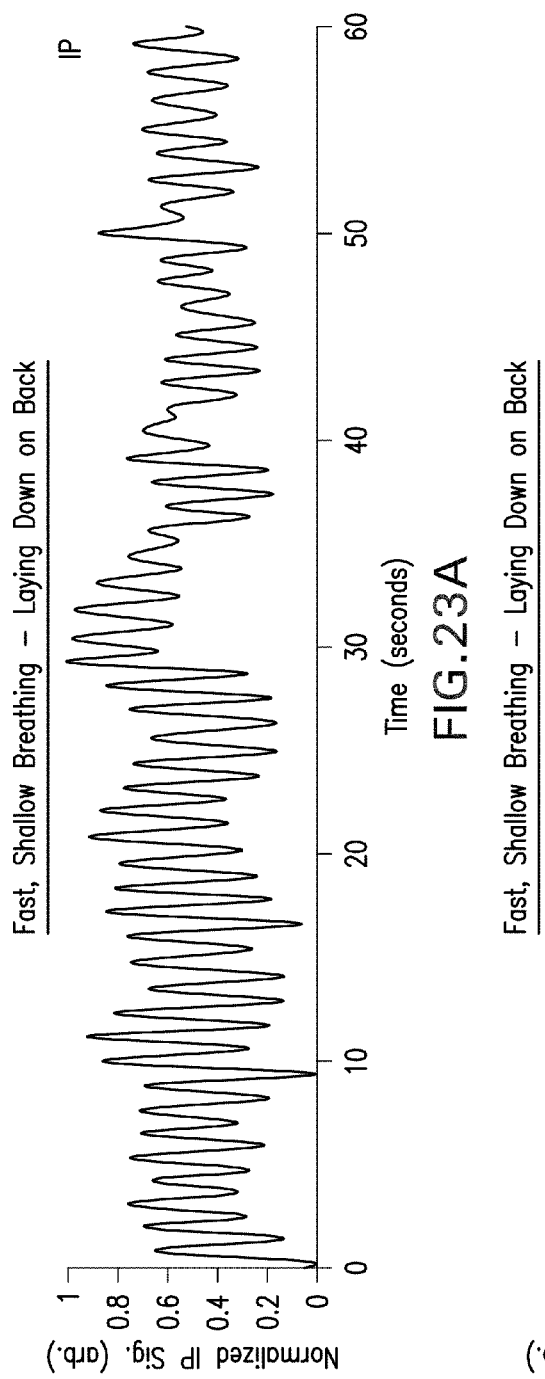
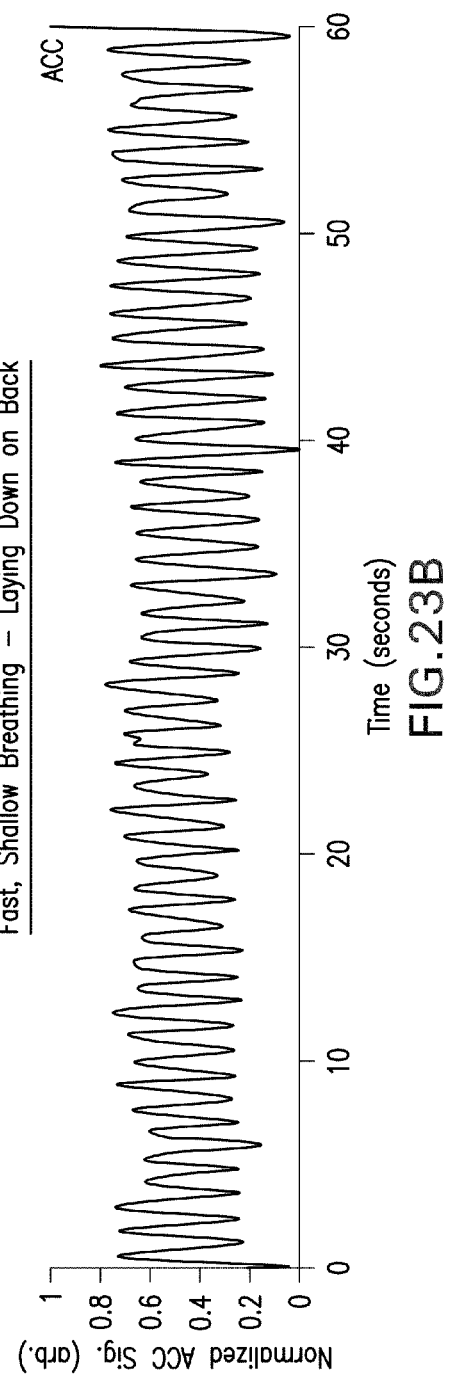
FIG. 23A
FIG. 23B

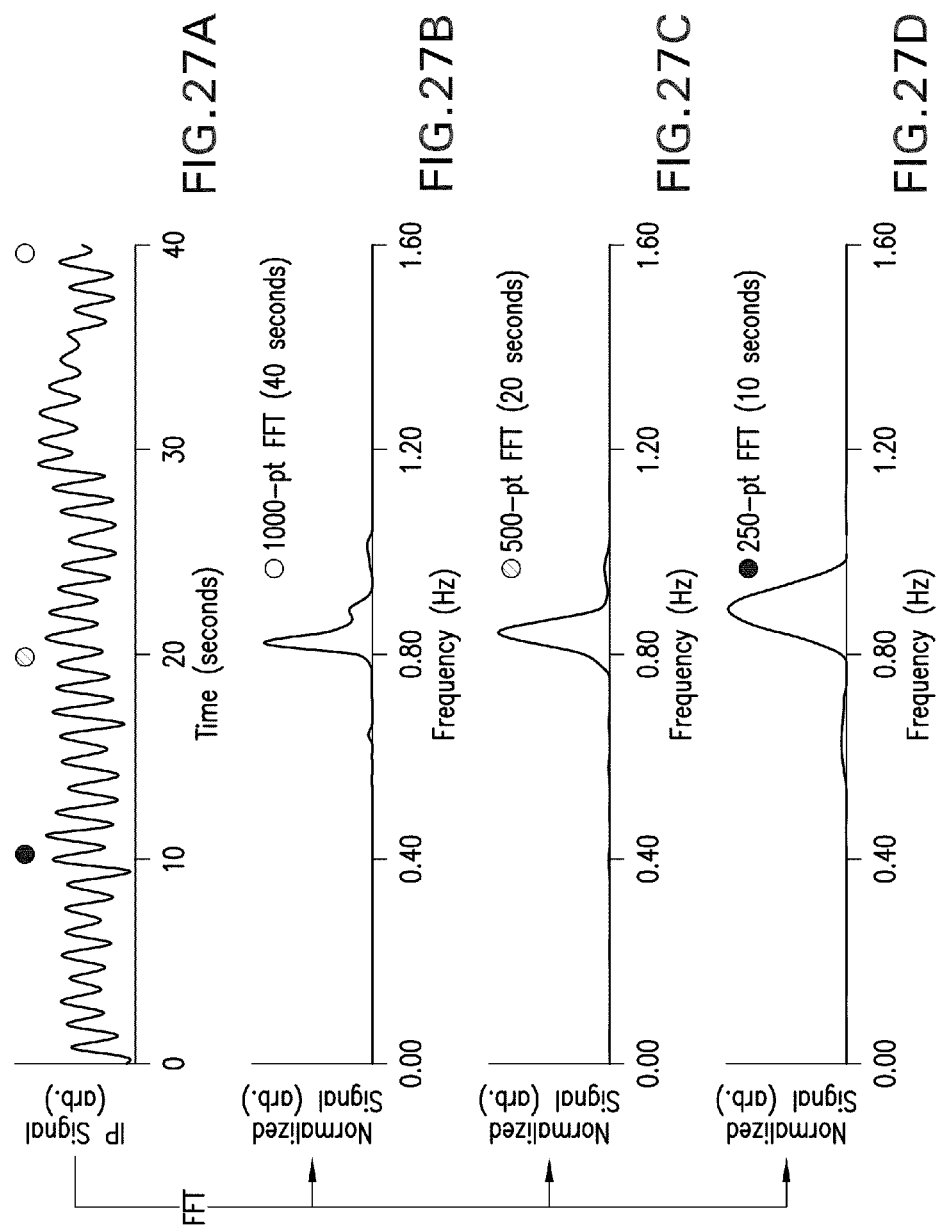

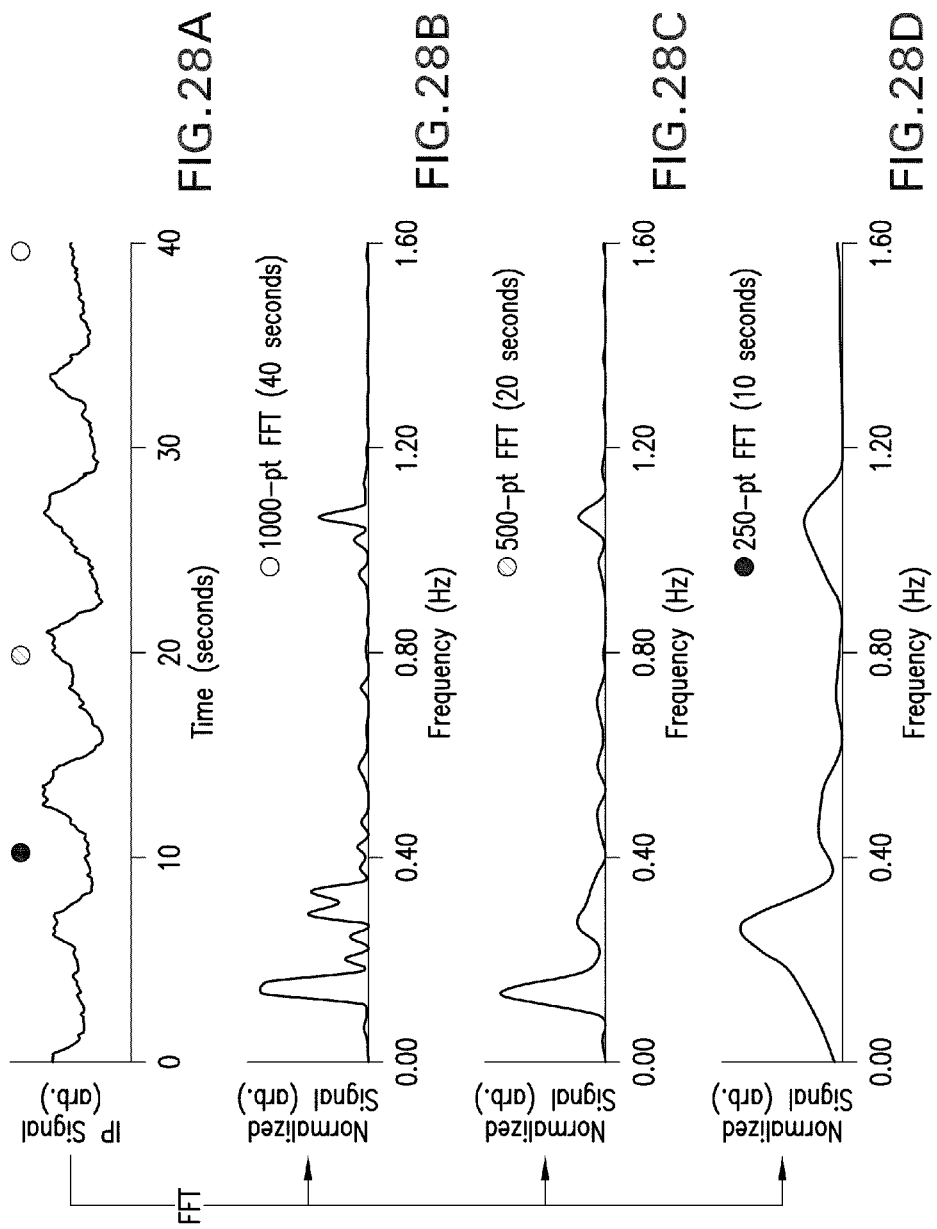

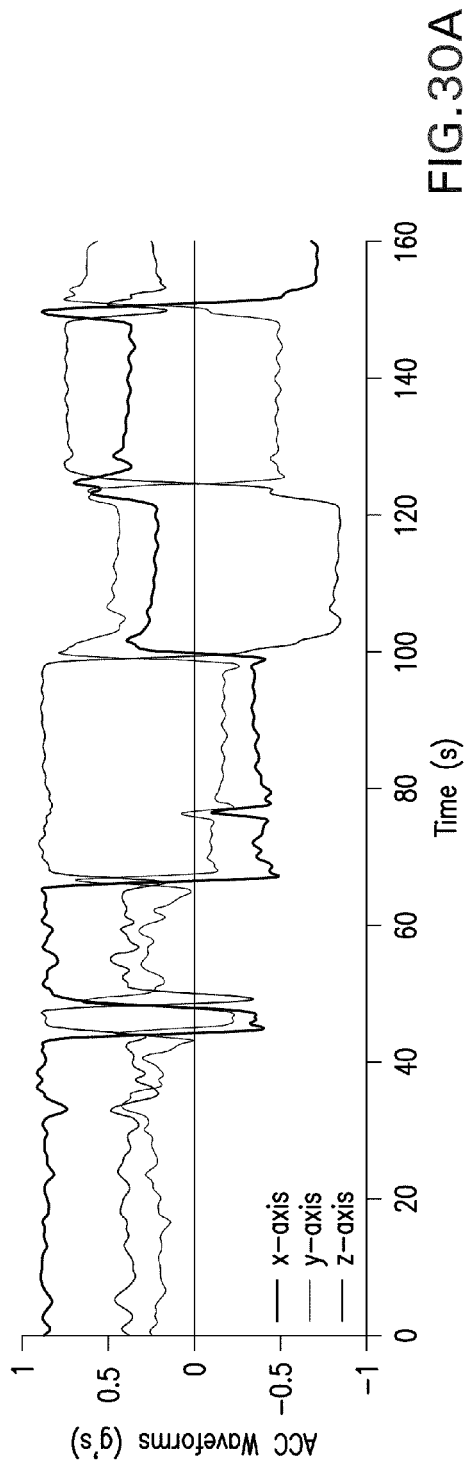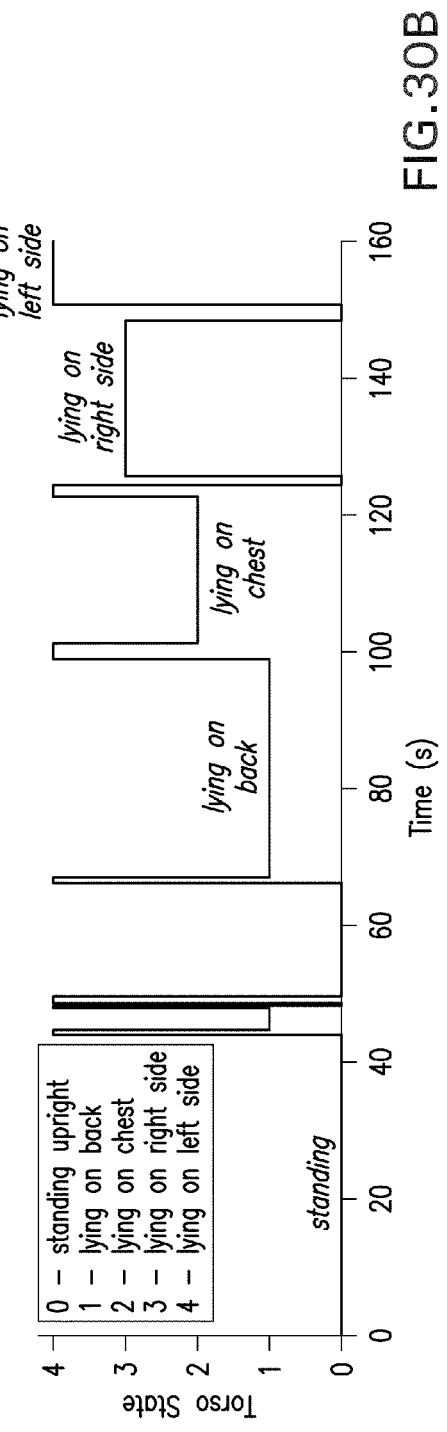
FIG. 30A
FIG. 30B

BODY-WORN MONITOR FOR MEASURING RESPIRATORY RATE

BACKGROUND OF THE INVENTION

1. Field of the Invention

The present invention relates to medical devices for monitoring vital signs, e.g., respiratory rate (RR).

2. Description of the Related Art

RR is a vital sign typically measured in hospitals using either an indirect, electrode-based technique called 'impedance pneumography' (IP), a direct optical technique called 'end-tidal CO2' (et-CO2), or simply through manual counting of breaths by a medical professional. IP is typically performed in lower-acuity areas of the hospital, and uses the same electrodes which measure an electrocardiogram (ECG) and corresponding heart rate (HR). These electrodes are typically deployed in a conventional 'Einthoven's triangle' configuration on the patient's torso. During IP, one of the electrodes supplies a low-amperage (~4 mA) current that is typically modulated at a high frequency (~50-100 kHz). Current passes through the patient's thoracic cavity, which is characterized by a variable, time-dependent capacitance that varies with each breath. A second electrode detects current which is modulated by the changing capacitance. Ultimately this yields an analog signal that is processed with a series of amplifiers and filters to detect the time-dependent capacitance change and, with subsequent analysis, the patient's RR.

In et-CO2, a device called a capnometer features a small plastic tube that inserts in the patient's mouth. With each breath the tube collects expelled CO2. A beam of infrared radiation emitted from an integrated light source passes through the CO2 and is absorbed in a time-dependent manner that varies with the breathing rate. A photodetector and series of processing electronics analyze the transmitted signal to determine RR. et-CO2 systems are typically used in high-acuity areas of the hospital, such as the intensive care unit (ICU), where patients often need ventilators to assist them in breathing.

In yet another technique, RR can be measured from the envelope of a time-dependent optical waveform called a photoplethysmogram (PPG) that is measured from the patient's index finger during a conventional measurement of the patient's oxygen saturation (SpO2). Breathing changes the oxygen content in the patient's blood and, subsequently, its optical absorption properties. Such changes cause a slight, low-frequency variation in the PPG that can be detected with a pulse oximeter's optical system, which typically operates at both red and infrared wavelengths.

Not surprisingly, RR is an important predictor of a decompensating patient. For example, a study in 1993 concluded that a RR greater than 27 breaths/minute was the most important predictor of cardiac arrests in hospital wards (Fieselmann et al., 'RR predicts cardiopulmonary arrest for internal medicine patients', *J Gen Intern Med* 1993; 8: 354-360). Subbe et al. found that, in unstable patients, relative changes in RR were much greater than changes in heart rate or systolic blood pressure; RR was therefore likely to be a better means of discriminating between stable patients and patients at risk (Subbe et al., 'Effect of introducing the Modified Early Warning score on clinical outcomes, cardio-pulmonary arrests and intensive care utilization in acute medical admissions', *Anaesthesia* 2003; 58: 797-802). Goldhill et al. reported that 21% of ward patients with a RR of 25-29 breaths/minute assessed by a critical care outreach service died in hospital (Goldhill et al., 'A physiologically-based early warning score for ward patients: the association between score and outcome', *Anaesthesia* 2005; 60: 547-553). Those with a higher RR had even higher mortality rates. In another study, just over half of all patients suffering a serious adverse event on the general wards (e.g. a cardiac arrest or ICU admission) had a RR greater than 24 breaths/minute. These patients could have been identified as high risk up to 24 hours before the event with a specificity of over 95% (Cretikos et al., 'The Objective Medical Emergency Team Activation Criteria: a case-control study', *Resuscitation* 2007; 73: 62-72). Medical references such as these clearly indicate that an accurate, easy-to-use device for measuring RR is an important component for patient monitoring within the hospital.

Despite its importance and the large number of available monitoring techniques, RR is notoriously difficult to measure, particularly when a patient is moving. During periods of motion, non-invasive techniques based on IP and PPG signals are usually overwhelmed by artifacts, and thus completely ineffective. This makes it difficult or impossible to measure RR from an ambulatory patient. Measurements based on et-CO2 are typically less susceptible to motion, but require a plastic tube inserted in the patient's mouth, which is uncomfortable and typically impractical for ambulatory patients.

SUMMARY OF THE INVENTION

This invention provides a technique for measuring RR using multiple input signals, including IP and accelerometer waveforms (ACC). After being measured with a body-worn system, an algorithm collectively analyzes these waveforms to determine RR from an ambulatory patient using combinations of simple peak counting, Fourier Transforms (FFT) and adaptive filtering. The patient's degree of motion determines which of these algorithms is implemented: simple peak counting is preferably used when the patient is undergoing no motion, while the FFT-based algorithm is used when motion is extreme. Adaptive filtering is typically used during periods of moderate motion. The algorithms are typically performed using a microprocessor, computer code and memory located in a wrist-worn transceiver, a sensor module located directly on the patient's chest, or on a remote server located, e.g., in a hospital. Calculations may be performed in a distributed manner, meaning portions of them can be performed with a first microprocessor (e.g., the server in the hospital), resulting in parameters that are then sent to a second microprocessor (e.g., in the wrist-worn transceiver) for final processing. Such a distributed model can reduce the computational burden on microprocessors within the body-worn monitor, thereby conserving power and extending battery life.

The accelerometer is typically mounted on the patient's torso (most typically the chest or belly), and measures small, breathing-induced movements to generate the time-dependent ACC waveform. The ACC waveform is also highly sensitive to the patient's motion and position, and thus the ACC waveform can be processed to determine parameters such as degree of motion, posture, and activity level. With the FFT-based algorithms, time-domain ACC and IP waveforms are mathematically transformed to the frequency domain and processed to generate a power spectrum. Further processing of this signal yields frequency components corresponding to both respiratory events and motion. The ACC waveform yields well-defined frequency components that are highly sensitive to motion. These signals can be collectively processed and used to filter out motion artifacts from the transformed IP waveform. The resulting power spectrum is then further processed with a smoothing function, yielding a set of frequency-domain peaks from which RR can be accurately calculated.

The multi-component algorithm also processes both IP and ACC waveforms to determine parameters for an adaptive filtering calculation. Once the parameters are determined, this filter is typically implemented with a finite impulse response (FIR) function. Ultimately this yields a customized filtering function which then processes the IP waveform to generate a relatively noise-free waveform with well-defined pulses corresponding to RR. Each pulse can then be further processed and counted to determine an accurate RR value, even during periods of motion.

The body-worn monitor measures IP and ACC waveforms as described above, along with PPG and ECG waveforms, using a series of sensors integrated into a comfortable, low-profile system that communicates wirelessly with a remote computer in the hospital. The body-worn monitor typically features three accelerometers, each configured to measure a unique signal along its x, y, and z axes, to yield a total of nine ACC waveforms. Typically the accelerometers are embedded in the monitor's cabling or processing unit, and are deployed on the patient's torso, upper arm, and lower arm. Each ACC waveform can be additionally processed to determine the patient's posture, degree of motion, and activity level. These parameters serve as valuable information that can ultimately reduce occurrences of 'false positive' alarms/alerts in the hospital. For example, if processing of additional ACC waveforms indicates a patient is walking, then their RR rate, which may be affected by walking-induced artifacts, can be ignored by an alarm/alert engine associated with the body-worn monitor. The assumption in this case is that a walking patient is likely relatively healthy, regardless of their RR value. Perhaps more importantly, with a conventional monitoring device a walking patient may yield a noisy IP signal that is then processed to determine an artificially high RR, which then triggers a false alarm. Such a situation can be avoided with an independent measurement of motion, such as that described herein. Other heuristic rules based on analysis of ACC waveforms may also be deployed according to this invention.

Sensors attached to the wrist and bicep each measure signals that are collectively analyzed to estimate the patient's arm height; this can be used to improve accuracy of a continuous blood pressure measurement (cNIBP), as described below, that measures systolic (SYS), diastolic (DIA), and mean (MAP) arterial blood pressures. And the sensor attached to the patient's chest measures signals that are analyzed to determine posture and activity level, which can affect measurements for RR, SpO2, cNIBP, and other vital signs. Algorithms for processing information from the accelerometers for these purposes are described in detail in the following patent applications, the contents of which are fully incorporated herein by reference: BODY-WORN MONITOR FEATURING ALARM SYSTEM THAT PROCESSES A PATIENT'S MOTION AND VITAL SIGNS (U.S. Ser. No. 12/469,182; filed May 20, 2009) and BODY-WORN VITAL SIGN MONITOR WITH SYSTEM FOR DETECTING AND ANALYZING MOTION (U.S. Ser. No. 12/469,094; filed May 20, 2009). As described therein, knowledge of a patient's motion, activity level, and posture can greatly enhance the accuracy of alarms/alerts generated by the body-worn monitor.

The body-worn monitor features systems for continuously monitoring patients in a hospital environment, and as the patient transfers from different areas in the hospital, and ultimately to the home. Both SpO2 and cNIBP rely on accurate measurement of PPG and ACC waveforms, along with an ECG, from patients that are both moving and at rest. cNIBP is typically measured with the 'Composite Technique', which is described in detail in the co-pending patent applications entitled: VITAL SIGN MONITOR FOR MEASURING BLOOD PRESSURE USING OPTICAL, ELECTRICAL, AND PRESSURE WAVEFORMS (U.S. Ser. No. 12/138,194; filed Jun. 12, 2008) and BODY-WORN SYSTEM FOR MEASURING CONTINUOUS, NON-INVASIVE BLOOD PRESSURE (CNIBP) (U.S. Ser. No. 12/650,354; filed Nov. 15, 2009), the contents of which are fully incorporated herein by reference.

As described in these applications, the Composite Technique (or, alternatively, the 'Hybrid Technique', as referred to therein) typically uses a single PPG waveform from the SpO2 measurement (typically generated with infrared radiation), along with the ECG waveform, to calculate a parameter called 'pulse transit time' (PTT) which strongly correlates to blood pressure. Specifically, the ECG waveform features a sharply peaked QRS complex that indicates depolarization of the heart's left ventricle, and, informally, provides a time-dependent marker of a heart beat. PTT is the time separating the peak of the QRS complex and the onset, or 'foot', of the PPG waveforms. The QRS complex, along with the foot of each pulse in the PPG, can be used to more accurately extract AC signals using a mathematical technique described in detail below. In other embodiments both the red and infrared PPG waveforms are collectively processed to enhance the accuracy of the cNIBP measurement.

The electrical system for measuring IP and ACC waveforms is featured in a sensor module that connects to an end of a cable that terminates in the wrist-worn transceiver, and is mounted directly on the patient's chest. The sensor module measures high-fidelity digital waveforms which pass through the cable to a small-scale, low-power circuit mounted on a circuit board that fits within the transceiver. There, an algorithm processes the two waveforms using the multi-component algorithm to determine RR. The transceiver additionally includes a touchpanel display, barcode reader, and wireless systems for ancillary applications described, for example, in the above-referenced applications, the contents of which have been previously incorporated herein by reference.

In one aspect, the invention features a system for measuring RR from a patient. The system includes an IP sensor, connected to at least two electrodes, and a processing system that receives and processes signals from the electrodes to measure an IP signal. The electrodes can connect to the IP sensor through either wired or wireless means. A motion sensor (e.g. an accelerometer) measures at least one motion signal (e.g. an ACC waveform) describing movement of a portion of the patient's body to which it is attached. The processing system receives the IP and motion signals, and processes them to determine, respectfully, frequency-domain IP and motion spectra. Both spectra are then collectively processed to remove motion components from the IP spectrum and determine RR. For example, during the processing, an algorithm determines motion frequency components from the frequency-domain motion spectrum, and then using a digital filter removes these, or parameters calculated therefrom, from the IP spectrum.

In embodiments, a single sensor module, adapted to be worn on the patient's torso, encloses both the IP sensor and the motion sensor. The sensor module typically includes at least one analog-to-digital converter configured to digitize the IP signal; this component may be integrated directly into a single-chip circuit (e.g. an application-specific integrated circuit, or ASIC), or in a circuit consisting of a collection of discrete components (e.g. individual resistors and capacitors). The sensor module can also include at least one analog-to-digital converter configured to digitize the motion signal.

Similarly, this component can be integrated directly into the accelerometer circuitry. Digitizing the IP and motion signals before transmitting them to the processing system has several advantages, as described in detail below.

In other embodiments, the sensor module includes a temperature sensor for measuring the patient's skin temperature, and an ECG circuit (corresponding to a three, five, or twelve-lead ECG) for measuring an ECG waveform. In embodiments, the sensor module simply rests on the patient's chest during a measurement, or can be connected with a small piece of medical tape. Alternatively, the housing features a connector that connects directly to an ECG electrode worn on the patient's torso.

The processing system is typically worn on the patient's wrist. Alternatively, this system can be within the sensor module, or within a remote computer server (located, e.g., in a hospital's IT system). Typically a wireless transceiver (e.g. a transceiver based on 802.11 or 802.15.4 transmission protocols) is included in the system, typically within the processing module. Such a transceiver, for example, can wirelessly transmit IP and ACC waveforms to a remote processing system for further analysis. In this case, the processing system is further configured to wireless transmit a RR value back to a second processor worn on the patient's body, where it can then be displayed (using, e.g., a conventional display).

Accelerometers used within the system typically generate a unique ACC waveform corresponding to each axis of a coordinate system. In embodiments the system can include three accelerometers, each worn on a different portion of the patient's body. Waveforms generated by the accelerometers can then be processed as described in detail below to determine the patient's posture.

In another aspect, the invention features an algorithm, typically implemented using compiled computer code, a computer memory, and a microprocessor, that processes IP and ACC waveforms by calculating their power spectra by way of a Fourier transform (e.g. a fast Fourier transform, of FFT). The algorithm then determines motion components from the frequency-dependent ACC spectrum, and using a digital filter removes these, or components calculated therefrom, from the frequency-dependent IP spectrum. This yields a processed, frequency-dependent IP spectrum which can then be analyzed as described in detail below to estimate RR, even when large amounts of motion-induced noise are evident on the IP signal.

In embodiments, power spectra for both the IP and ACC waveforms are calculated from a complex FFT that includes both real and imaginary components. In other embodiments, alternative mathematical transforms, such as a Laplace transform, can be used in place of the FFT.

To determine a digital filter from the ACC power spectrum, the algorithm typically includes a method for first finding a peak corresponding to one or more frequencies related to the patient's motion. A bandpass filter, characterized by a passband which filters out these (and related) frequencies, is then generated and used to process the IP spectrum. Alternatively, these frequencies can simply be divided or subtracted from the IP spectrum. In all cases, this yields a processed IP spectrum which is then further analyzed to determine a frequency corresponding to RR. Analysis can include smoothing, averaging, or related methodologies uses to extract a single frequency, corresponding to RR, from a collection of frequencies. In embodiments, the algorithm can also include a component that generates an alarm if the patient's RR is greater than a first pre-determined threshold, or less than a second pre-determined threshold. The alarm can be generated by considering both the patient's RR and posture.

In another aspect, the invention features a multi-component algorithm for determining RR. The multi-component algorithm first determines a motion parameter from the ACC waveform. The motion parameter indicates the patient's degree of motion, activity level, or posture. Based on the motion parameter, the multi-component algorithm then selects one of the following algorithms to process one or both of the ACC and IP waveforms to determine RR: i) a first algorithm featuring counting breathing-induced pulses in the IP waveform; and ii) a second algorithm featuring collectively processing both the ACC and IP waveform to determine a digital adaptive filter, and then processing one of these waveforms with the adaptive filter to determine RR; and iii) a third algorithm featuring mathematically transforming both the ACC and IP waveforms into frequency-domain spectra, and then collectively processing the spectra to determine RR. Typically the first, second, and third algorithms are deployed, respectively, when the motion parameter indicates the patient's motion is non-existent, minimal, or large. For example, the first algorithm is typically deployed when the patient is resting; the second algorithm deployed when the patient is moving about somewhat; and the third algorithm deployed when the patient is standing up, and possibly walking or even running.

In another aspect, the multi-component algorithm is deployed on one or more microprocessors associated with the system. For example, to conserve battery life of the body-worn monitor, numerically intensive calculations (such as the FFT or those used to generate the digital filter) can be performed on a remote server; intermediate or final parameters associated with these calculations can then be wirelessly transmitted back to the body-worn monitor for further processing or display. In another embodiment, portions of the multi-component algorithm can be carried out by microprocessors located in both the wrist-worn transceiver and chest-worn sensor module. The microprocessors can communicate through serial or wireless interfaces. This latter approach will have little impact on battery life, but can reduce processing time by simultaneously performing different portions of the calculation.

In another aspect, the invention provides a method for measuring RR from a patient using an algorithm based on a digital adaptive filter. In this approach, the body-worn monitor measures both IP and ACC waveforms as described above. The waveforms are then collectively processed to determine a set of coefficients associated with the adaptive filter. Once calculated, the coefficients are stored in a computer memory. At a later point in time, the monitor measures a second set of IP and ACC waveforms, and analyzes these to determine a motion parameter. When the motion parameter exceeds a pre-determined threshold, the algorithm processes the set of coefficients and the latest IP waveform to determine a processed IP waveform, and then analyzes this to determine RR.

In embodiments, the digital adaptive filter is calculated from an impulse response function, which in turn is calculated from either a FIR function or an autoregressive moving average model. The order of the adaptive filter calculated from the impulse response function is typically between 20 and 30, while the order of the filter calculated from the autoregressive moving average model is typically between 1 and 5. A specific mathematic approach for calculating the digital adaptive filter is described below with reference to Eqs. 1-16. As described above, the coefficients can be calculated using a microprocessor located on the wrist-worn transceiver, sensor module, or a remote server.

In yet another aspect, the invention provides a system for measuring RR featuring a sensor module configured to be worn on the patient's torso. The sensor module includes sensors for measuring both IP and ACC waveforms, and a serial transceiver configured to transmit the digital signals through a cable to a wrist-worn processing system. This system features a connector that receives the cable, and a processor that receives digital signals from the cable and collectively processes them with a multi-component algorithm to determine RR. In embodiments, the sensor module digitally filters the IP and ACC waveforms before they pass through the cable. The cable can also include one or more embedded accelerometers, and is configured to attach to the patient's arm.

In all embodiments, the wrist-worn transceiver can include a display configured to render the patient's RR and other vital signs, along with a touchpanel interface. A wireless transceiver within the wrist-worn transceiver can transmit information to a remote computer using conventional protocols such as 802.11, 802.15.4, and cellular (e.g. CDMA or GSM). The remote computer, for example, can be connected to a hospital network. It can also be a portable computer, such as a tablet computer, personal digital assistant, or cellular phone.

Many advantages are associated with this invention. In general, it provides an accurate measurement of RR, along with an independent measurement of a patient's posture, activity level, and motion. These parameters can be collectively analyzed to monitor a hospitalized patient and improve true positive alarms while reducing the occurrence of false positive alarms. Additionally, the measurement of RR is performed with a body-worn monitor that is comfortable, lightweight, and low-profile, making it particularly well suited for ambulatory patients. Such a monitor could continuously monitor a patient as, for example, they transition from the emergency department to the ICU, and ultimately to the home after hospitalization.

Still other embodiments are found in the following detailed description of the invention and in the claims.

BRIEF DESCRIPTION OF THE DRAWINGS

FIGS. 15A-E show graphs of an ACC waveform filtered initially with a 0.01→2 Hz bandpass filter (FIG. 15A; top), an IP waveform filtered initially with a 0.01→12 Hz bandpass (FIG. 15B), an IP waveform adaptively filtered with a bandpass filter ranging from 0.01 Hz to 1.5 times the breathing rate calculated from the ACC waveform in FIG. 15A (FIG. 15C), a first derivative of the filtered IP waveform in FIG. 15C (FIG. 15D), and the adaptively filtered IP waveform in FIG. 15C along with markers indicating slow, deep breaths as determined from the algorithm shown by the flow chart in FIG. 14 (FIG. 15E; bottom);

FIG. 15F is a flow chart showing the algorithmic steps used to process the waveforms shown in FIGS. 15A-E;

FIGS. 16A-E show graphs of an ACC waveform filtered initially with a 0.01→2 Hz bandpass filter (FIG. 16A; top), an IP waveform filtered initially with a 0.01→12 Hz bandpass (FIG. 16B), an IP waveform adaptively filtered with a bandpass filter ranging from 0.01 Hz to 1.5 times the breathing rate calculated from the ACC waveform in FIG. 16A (FIG. 16C), a first derivative of the filtered IP waveform in FIG. 16C (FIG. 16D), and the adaptively filtered IP waveform in FIG. 16C along with markers indicating fast, deep breaths as determined from the algorithm shown by the flow chart in FIG. 14 (FIG. 16E; bottom);

FIG. 16F is a flow chart showing the algorithmic steps used to process the waveforms shown in FIGS. 16A-E;

FIG. 18 shows a schematic drawing of Algorithm 4 used in the multi-component algorithm of FIG. 6 to calculate RR;

FIGS. 22A-C show, respectively, a time-domain IP waveform measured from a stationary patient laying down on their back and breathing normally (FIG. 22A), a time-domain ACC waveform measured simultaneously from the same patient (FIG. 22B), and frequency-domain power spectra of both the time-domain IP waveform of FIG. 22A and ACC waveform of FIG. 22B (FIG. 22C);

FIGS. 23A-C show, respectively, a time-domain IP waveform measured from a stationary patient laying down on their back and breathing rapidly (FIG. 23A), a time-domain ACC waveform measured simultaneously from the same patient (FIG. 23B), and frequency-domain power spectra of both the time-domain IP waveform of FIG. 23A and ACC waveform of FIG. 23B (FIG. 23C);

FIG. 27A shows a time-domain IP waveform measured from a rapidly breathing stationary patient;

FIGS. 27B-D show frequency-domain power spectra calculated from the time-domain IP waveform of FIG. 27A using, respectively, a 1000-point FFT, a 500-point FFT, and a 250-point FFT;

FIG. 28A shows a time-domain IP waveform measured from a slowly breathing stationary patient;

FIGS. 28B-D show frequency-domain power spectra calculated from the time-domain IP waveform of FIG. 28A using, respectively, a 1000-point FFT, a 500-point FFT, and a 250-point FFT;

FIG. 30A shows a graph of time-dependent ACC waveforms measured from a patient's chest during different postures; and FIG. 30B shows a graph of time-dependent postures determined by processing the ACC waveforms of FIG. 30A with an algorithm and coordinate axis shown in FIG. 29.

DETAILED DESCRIPTION OF THE INVENTION

Sensor Configuration

Figure 1:
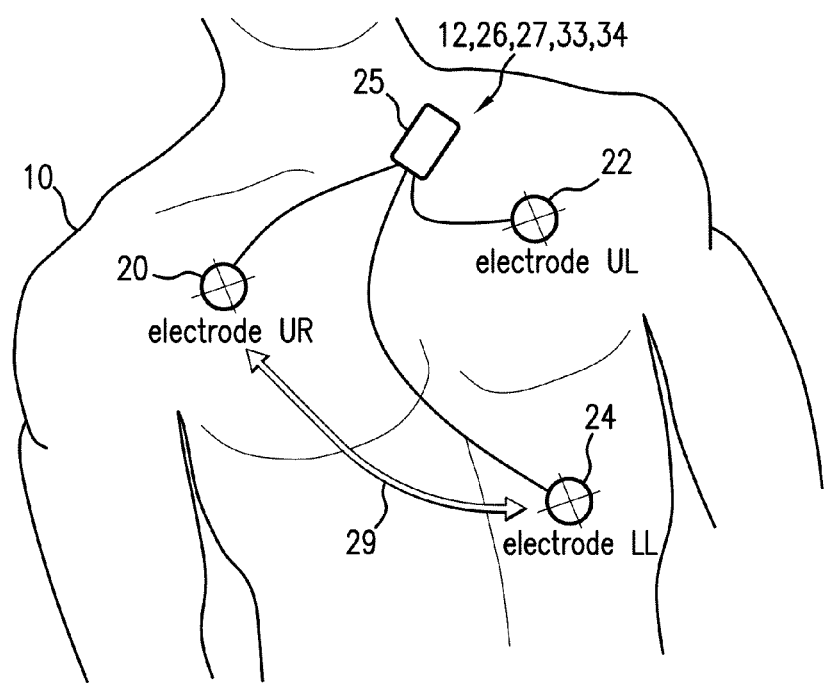
FIG. 1 shows a schematic view of a patient wearing a sensor module on their chest that connects to three electrodes arranged in an Einthoven's triangle configuration and measures both ACC and IP waveforms.
Figure 2:
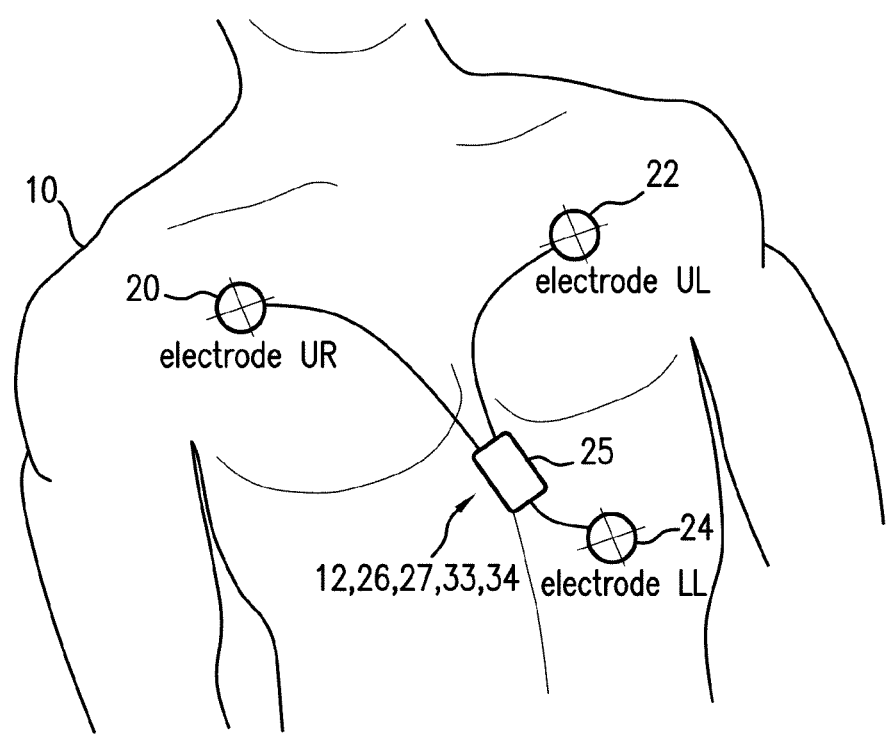
FIG. 2 shows a schematic view of a patient wearing a sensor module on their belly that connects to three electrodes arranged in an Einthoven's triangle configuration and measures both ACC and IP waveforms.
Figure 3:
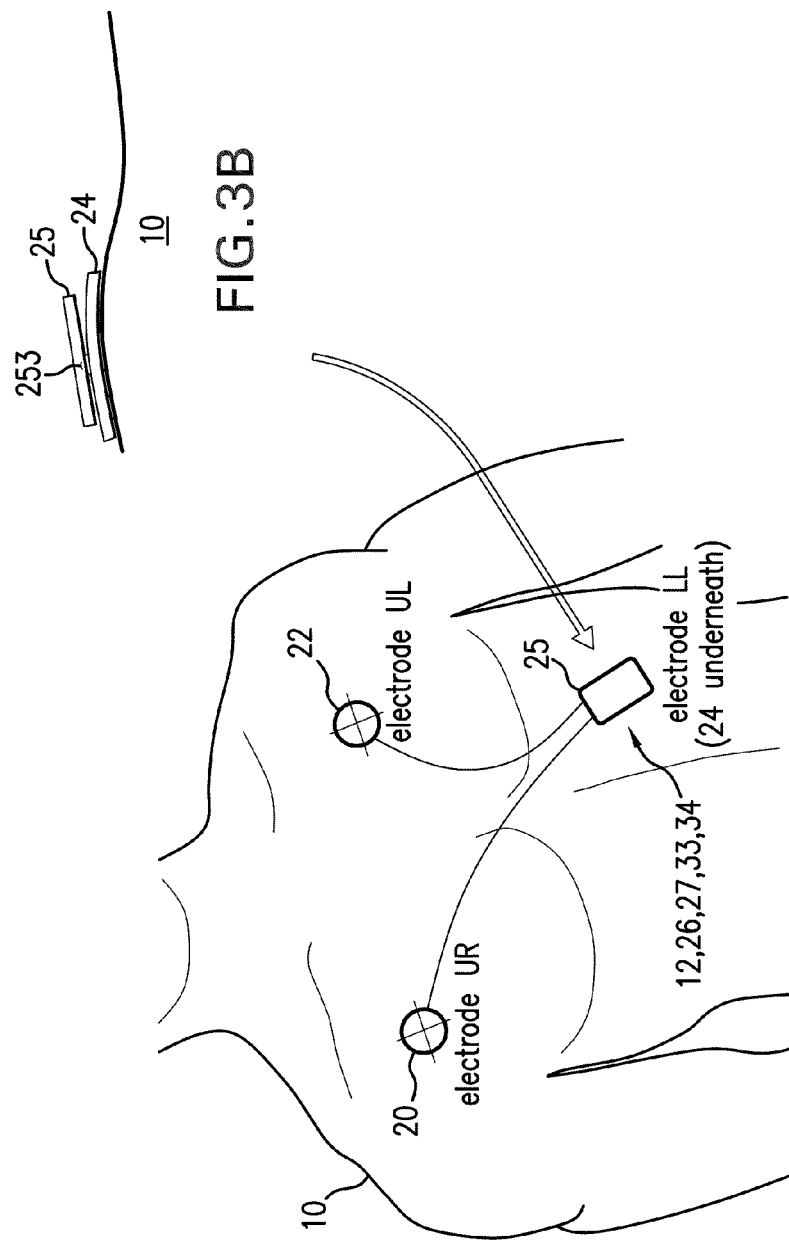
FIG. 3A is a schematic view of a patient wearing an alternate embodiment of the invention featuring a sensor module for measuring IP and ACC waveforms that connects directly through an electrode to the patient's belly.
FIG. 3B is a schematic, cross-sectional view of the sensor module of FIG. 3A connected to the patient's belly with the electrode.

Referring to FIGS. 1 and 2, a sensor module 25 featuring an IP circuit 27 and accelerometer 12 is mounted on the chest of a patient 10 to simultaneously measure IP and ACC waveforms. A multi-component algorithm, featuring specific algorithms based on simple peak counting, FFT analysis, and adaptive filters processes these waveforms to accurately measure RR even when the patient 10 is moving. During a measurement, both the IP 27 and an ECG circuit 26 within the sensor module connect to a trio of electrodes 20, 22, 24 typically positioned on the patient's torso in an Einthoven's triangle configuration. Each electrode 20, 22, 24 measures a unique analog signal that passes through a shielded cable to the ECG circuit 26. This component typically includes a differential amplifier and a series of analog filters with passbands that pass the high and low-frequency components that contribute to the ECG waveform, but filter out components associated with electrical and mechanical noise. To determine RR, the IP circuit 27 generates a low-amperage current (typically 1-4 mA) that is modulated at a high frequency (typically 50-100 kHz). The current typically passes through electrode LL ('lower left') 24, which is located on the lower left-hand side of the patient's torso. It then propagates through the patient's chest, as indicated by the arrow 29, where a respiration-induced capacitance change modulates it according to the RR. Electrode UR ('upper right') 20 detects the resultant analog signal, which is then processed with a separate differential amplifier and series of analog filters within the IP circuit to determine an analog IP waveform featuring a low-frequency series of pulses corresponding to RR. Typically the analog filters in the IP circuit 27 are chosen to filter out high-frequency components that contribute to the ECG QRS complex.

The accelerometer 12 mounted within the sensor module 25 measures ACC waveforms that are modulated by the patient's general motion and posture, along with small respiratory-induced motions of the patient's torso. The accelerometer 12 simultaneously measures acceleration (e.g. motion) along x, y, and z axes of a local coordinate system, such as that shown in FIG. 29. As shown in this figure, and described in more detail below, the accelerometer 12 is preferably aligned so the z axis points into the patient's torso. Within the accelerometer 12 is an internal analog-to-digital converter that generates a digital ACC waveform corresponding to each axis.

Also within the sensor module 25 is a microprocessor 33 and analog-to-digital converter (not shown in the figure) that digitize the IP and ACC waveforms, and sends them through a serial protocol (e.g. the control area network, or CAN protocol) to the wrist-worn transceiver for further processing. There, IP and ACC waveforms are processed with the multi-component algorithm to determine the patient's RR. Alternatively, the algorithms can be performed in part with a remote server, or with the microprocessor 33 mounted within the sensor module. Additional properties such as the patient's posture, degree of motion, and activity level are determined from these same digital ACC waveforms. The axis within the accelerometer's coordinate system that is aligned along the patient's torso (and thus orthogonal to their respiration-induced torso movement) is typically more sensitive to events not related to respiration, e.g. walking and falling.

In a preferred embodiment, digital accelerometers manufactured by Analog Devices (e.g. the ADXL345 component) are used in the configuration shown in FIG. 1. These sensors detect acceleration over a range of +/−2 g (or, alternatively, up to +/−8 g) with a small-scale, low-power circuit.

Many patient's are classified as 'belly breathers', meaning during respiration their belly undergoes larger movements than their chest. A relative minority of patients are 'chest breathers', indicating that it is the chest that undergoes the larger movements. For this reason it is preferred that RR is determined using an ACC waveform detected along the z-axis with an accelerometer positioned on the patient's belly. In alternate configurations, a separate accelerometer mounted on the chest can be used in its place or to augment data collected with the belly-mounted sensor. Typically, ACC waveforms along multiple axes (e.g. the x and y-axes) are also modulated by breathing patterns, and can thus be used to estimate RR. In still other configurations multiple signals from one or more accelerometers are collectively processed to determine a single 'effective' ACC waveform representing, e.g., an average of multiple ACC waveforms. This waveform is then processed as described herein to determine the patient's RR.

In other embodiments, the sensor module 25 includes a temperature sensor 34, such as a conventional thermocouple, that measures the skin temperature of the patient's chest. This temperature is typically a few degrees lower than conventional core temperature, usually measured with a thermometer inserted in the patient's throat or rectum. Despite this discrepancy, skin temperature measured with the temperature sensor 34 can be monitored continuously and can therefore be used along with RR and other vital signs to predict patient decompensation.

In a preferred embodiment, both the ECG and IP waveforms are generated with a single ASIC, or alternatively with a circuit composed of a series of discrete elements which are known in the art. The ASIC has an advantage in that it is a single chip and is included in a circuit that typically contains fewer electrical components, is relatively small, and is typically very power efficient. In either embodiment, the ECG circuit typically includes an internal analog-to-digital converter that digitizes both waveforms before transmission to the wrist-worn transceiver for further processing.

Transmission of digital IP, ECG, and ACC waveforms, along with processed RR values, has several advantages over transmission of analog waveforms. First, a single transmission line in the monitor's cabling can transmit multiple digital waveforms, each generated by different sensors. This includes multiple ECG waveforms (corresponding, e.g., to vectors associated with three, five, and twelve-lead ECG systems) from the ECG circuit 26, the IP waveform from the IP circuit 27, and ACC waveforms associated with the x, y, and z axes of accelerometers 10, 12 attached to the patient's chest. Limiting the transmission line to a single cable reduces the number of wires attached to the patient, thereby decreasing the weight and cable-related clutter of the body-worn monitor. Second, cable motion induced by an ambulatory patient can change the electrical properties (e.g. electrical impendence) of its internal wires. This, in turn, can add noise to an analog signal and ultimately the vital sign calculated from it. A digital signal, in contrast, is relatively immune to such motion-induced artifacts. More sophisticated ECG circuits can plug into the wrist-worn transceiver to replace the three-lead system shown in FIGS. 1 and 2. These ECG circuits, for example, can include, e.g., five and twelve leads.

Figure 4:
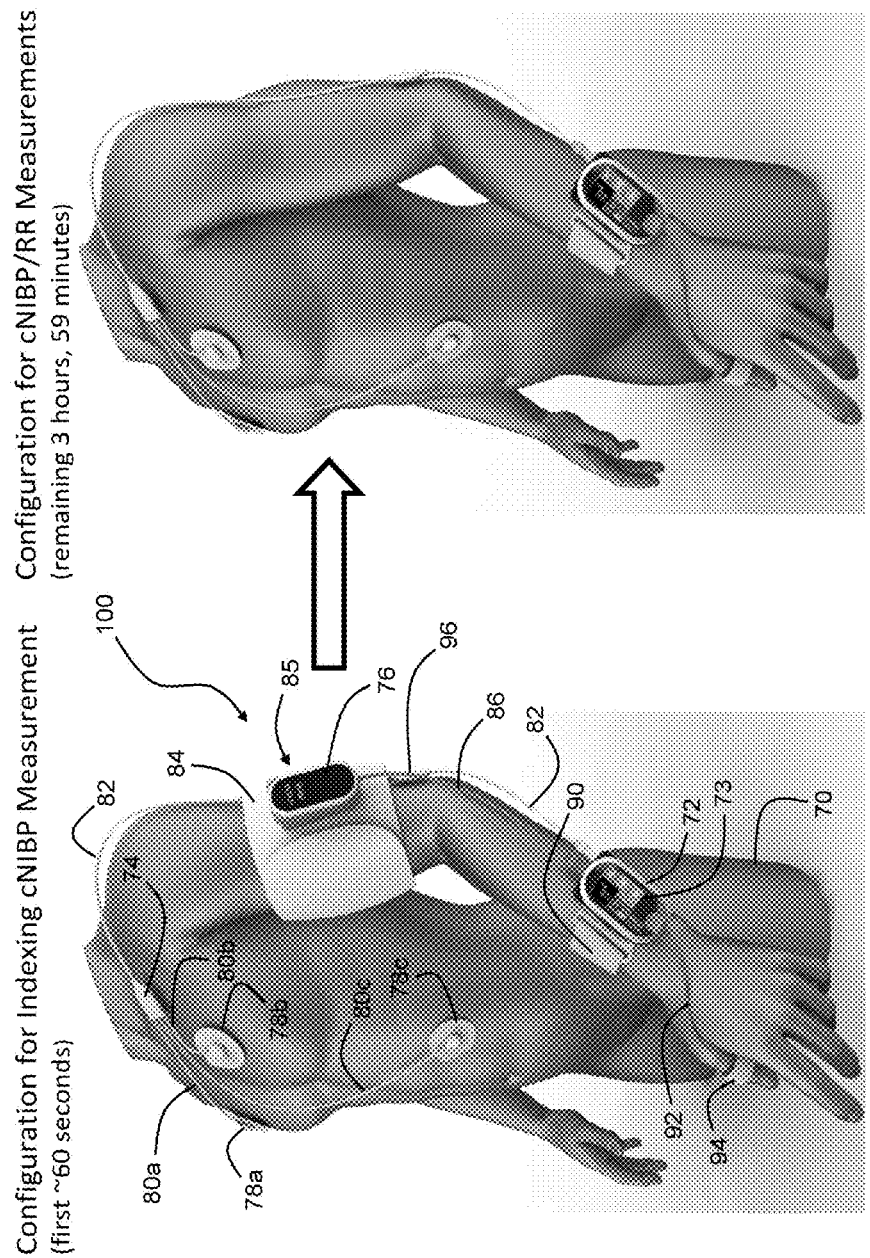
FIGS. 4A and 4B show, respectively, a three-dimensional image of the body-worn monitor of the invention attached to a patient during and after an initial indexing measurement.

Digital data streams are typically transmitted to the wrist-worn transceiver using a serial protocol, such as the CAN protocol, USB protocol, or RS-232 protocol. CAN is the preferred protocol for the body-worn monitor described in FIGS. 4A, 4B.

Multi-Component Algorithm for Determining RR

Figure 5:
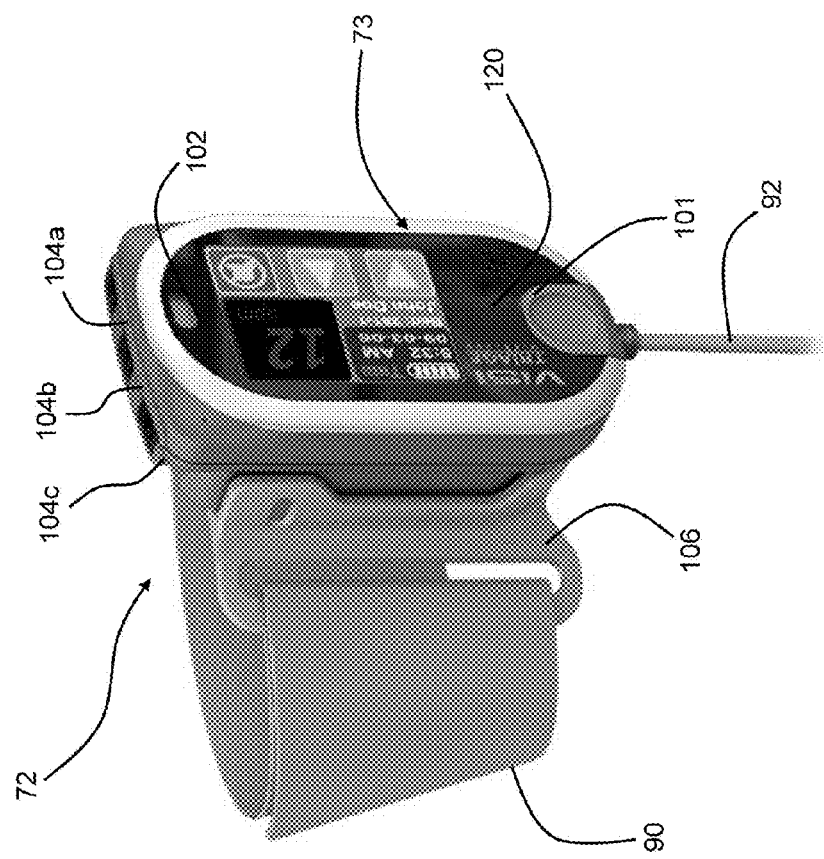
FIG. 5 shows a three-dimensional image of the wrist-worn transceiver used with the body-worn monitor from FIGS. 4A and 4B.
Figure 6:
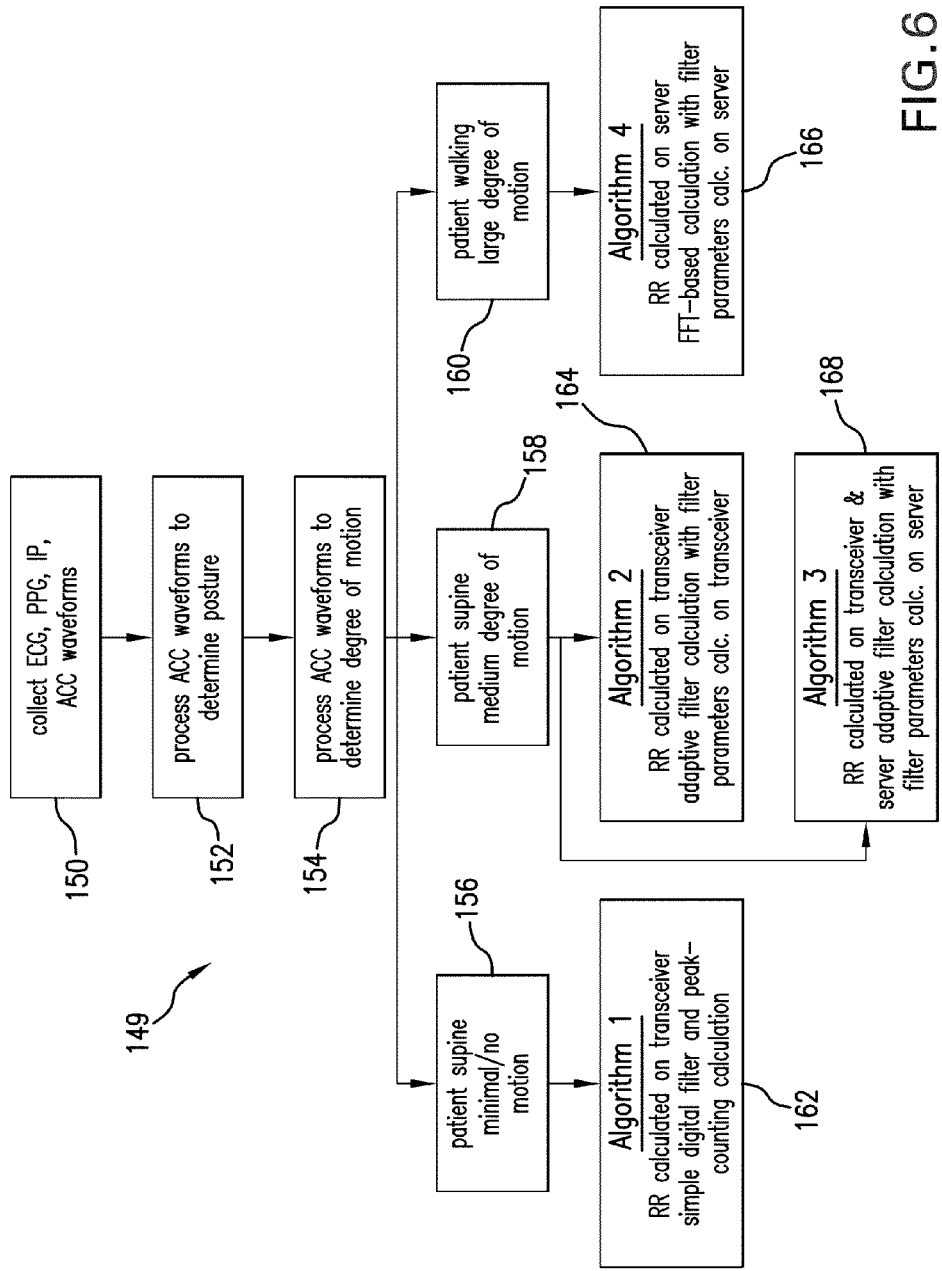
FIG. 6 shows a schematic view of a multi-component algorithm used to collectively process ACC and IP waveforms to measure RR according to the invention.

FIG. 6 shows an overview of a multi-component algorithm 149, implemented with the body-worn monitor shown in FIGS. 4A, 4B, and 5 and an accompanying server, which determines a patient's RR according to the invention. The algorithm features the following components for determining RR from a hospitalized patient undergoing different levels of motion:

Algorithm 1—simple peak-counting calculation implemented on the wrist-worn transceiver; used when patient motion is minimal or non-existent Algorithm 2—adaptive filtering calculation with filtering parameters calculated on the wrist-worn transceiver; used when some patient motion is evident Algorithm 3—adaptive filtering calculation with filtering parameters calculated on the server and then transmitted to the wrist-worn transceiver; used when some patient motion is evident Algorithm 4—FFT-based calculation with active noise cancellation, performed on the server with processed data transmitted to the wrist-worn transceiver; used when large amounts of patient motion is evident Each of these algorithms, along with both respiratory and motion data to support them, are described in more detail below.

Algorithms 1-4—Simultaneous Determination of Motion and Respiratory Signals

Figure 29:
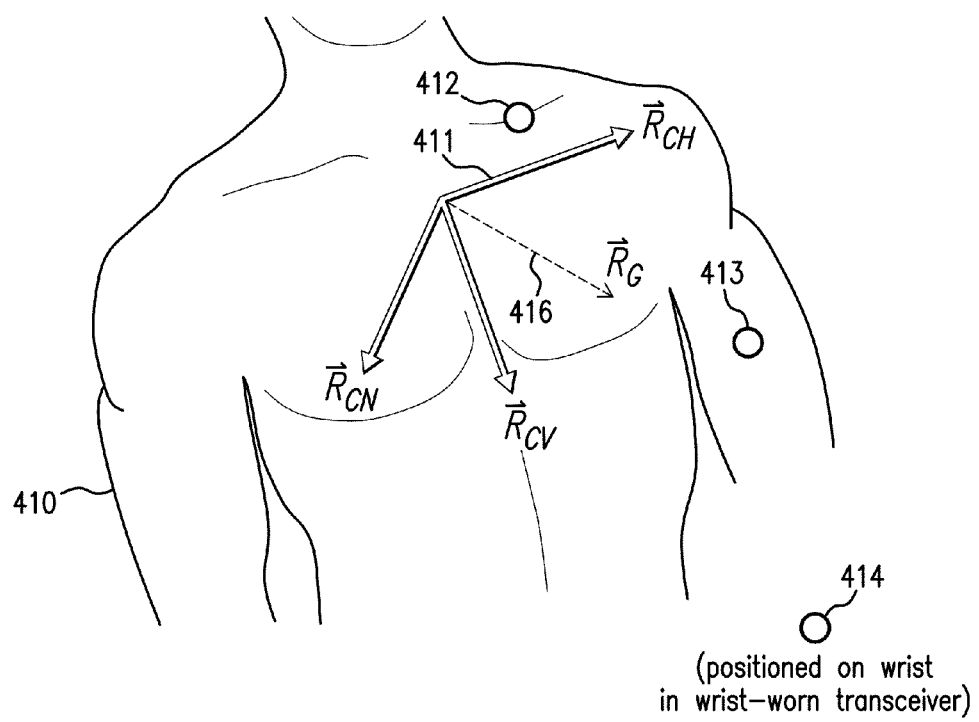
FIG. 29 shows a schematic view of the patient of FIG. 1 and a coordinate axis used with an algorithm and ACC waveforms to determine the patient's posture.

Referring again to FIG. 6, before Algorithms 1-4 are implemented, the body-worn monitor collects ECP, PPG, IP, and ACC waveforms (step 150) from the patient, as described above with references to FIGS. 1-5. A patient's degree of motion (step 152) and their posture (step 154) are determined by processing the ACC waveforms using algorithms described in detail in the following pending patent applications, the contents of which have been previously incorporated herein by reference: BODY-WORN MONITOR FEATURING ALARM SYSTEM THAT PROCESSES A PATIENT'S MOTION AND VITAL SIGNS (U.S. Ser. No. 12/469,182; filed May 20, 2009) and BODY-WORN VITAL SIGN MONITOR WITH SYSTEM FOR DETECTING AND ANALYZING MOTION (U.S. Ser. No. 12/469,094; filed May 20, 2009). FIGS. 29 and 30, below, further indicate how processing of ACC waveforms yields both posture, degree of motion, and activity level.

The multi-component algorithm 149 processes these motion-related properties to determine which of the four above-described algorithms to implement. The selected algorithm then simultaneously processes ECG and ACC waveforms to determine RR. As described above, motion can significantly complicate determination of RR, as these two signals often occur at similar frequencies (typically 0.1-2 Hz), and feature signal components (e.g. 'pulses' due to breathing and walking) that look similar and themselves are composed of common frequency components. In addition to RR, the body-worn monitor calculates cNIBP using the ECG and PPG waveforms, and SpO2 from PPG waveforms generated simultaneously with both red and infrared light sources, as described above. HR is calculated from the ECG waveform using methods known in the art.

Both high-level and detailed aspects of Algorithms 1-4 are described below.

Algorithm 1—Peak Counting

Algorithm 1 (step 162) is implemented after determining that the patient is supine and undergoing minimal or no motion (step 156). Here, it is assumed that the IP waveform used to determine RR is not significantly corrupted by motion, and thus RR can be calculated with relatively simple means. Put another way, in this case there is minimal coupling between the ACC and IP waveforms; collective processing of these waveforms to remove motion-related artifacts, as is done with Algorithms 2-4, is therefore not required. Algorithm 1 typically yields a highly accurate RR, and because of its simplicity requires relatively few computational cycles. This in turn reduces power consumption and prolongs battery lifetime on the wrist-worn transceiver.

Figure 7:
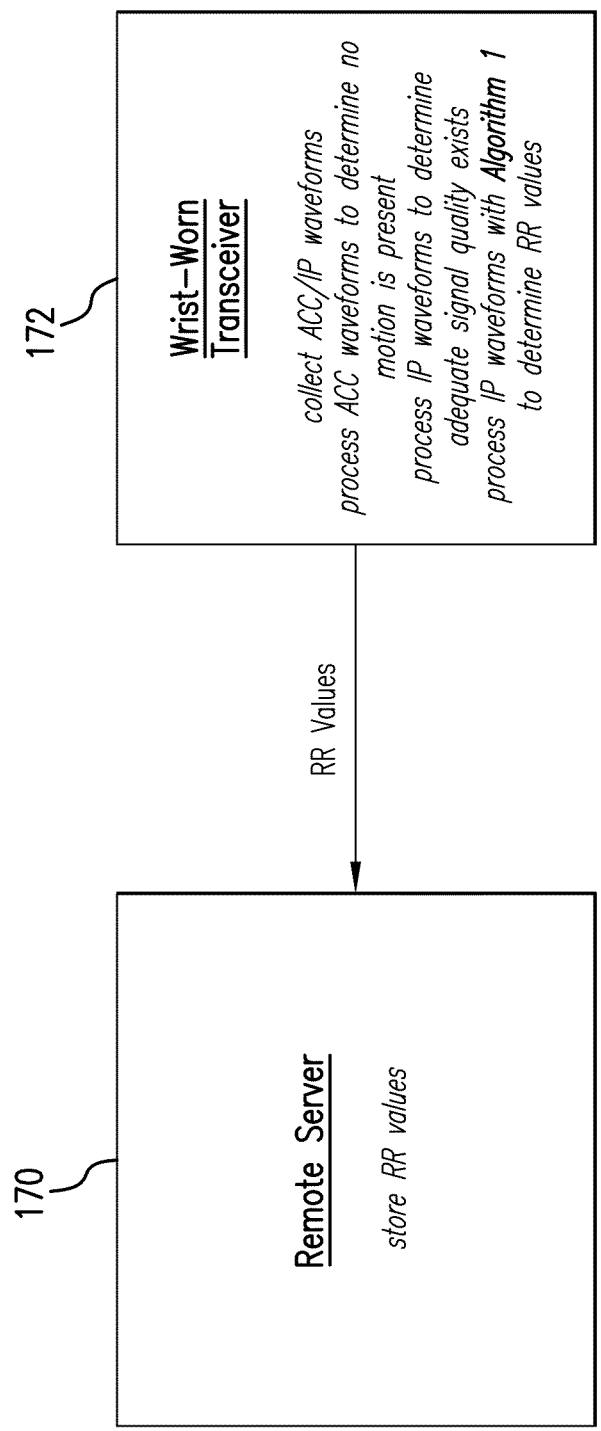
FIG. 7 shows a schematic drawing of Algorithm 1 used in the multi-component algorithm of FIG. 6.
Figure 8:
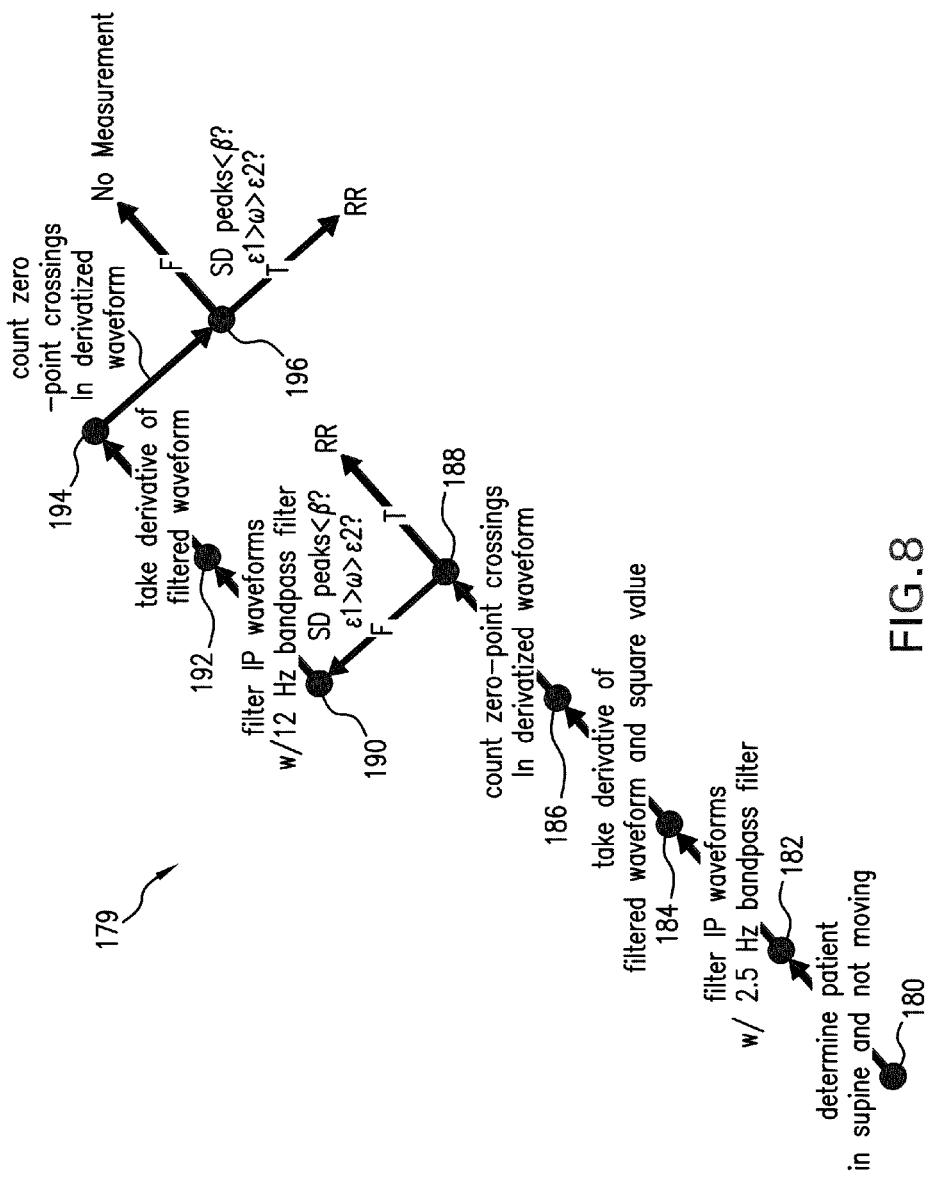
FIG. 8 shows a schematic drawing of computation steps used in Algorithm 1 to calculate RR.

FIG. 7 shows a high-level diagram describing Algorithm 1. In this case, all calculations are performed with a microprocessor on the wrist-worn transceiver 172 to yield final values for RR. Once determined, a wireless system on the transceiver sends these values to a remote server 170 for further processing, display, storage, and incorporation into a hospital's medical records system. The wrist-worn transceiver 172 additionally displays RR values on the transceiver's touch-panel display so that they can be viewed at the patient's bedside. FIG. 8 shows the specific details of this calculation. It begins by confirming that the patient is supine and not moving (step 180), which as described above is accomplished by processing ACC signals generated by the three 3-axis accelerometers integrated in the body-worn monitor. The IP waveform is then digitally filtered with a 2.5 Hz digital band-pass filter to remove extraneous noise (typically from electrical and mechanical sources) that complicates processing of the waveform. In typical applications, the digital filter features a second-order infinite impulse response (IIR). In order to remove any phase distortion, the IIR filter is executed in both the forward and reverse directions. The reverse filtering step doubles the effective order of the filter, and cancels out any phase distortion introduced by the forward filtering operation. The reverse filtering step is implemented by executing the standard IIR difference equation, performing a time-reversal on the outputted data, and then executing the same IIR difference equation. While effective in removing phase distortion, such additional steps require an extra difference computation which cannot be performed in real-time on a stream of data. This, in turn, increases power consumption in the wrist-worn transceiver, and thus shortens battery life.

Figure 9:
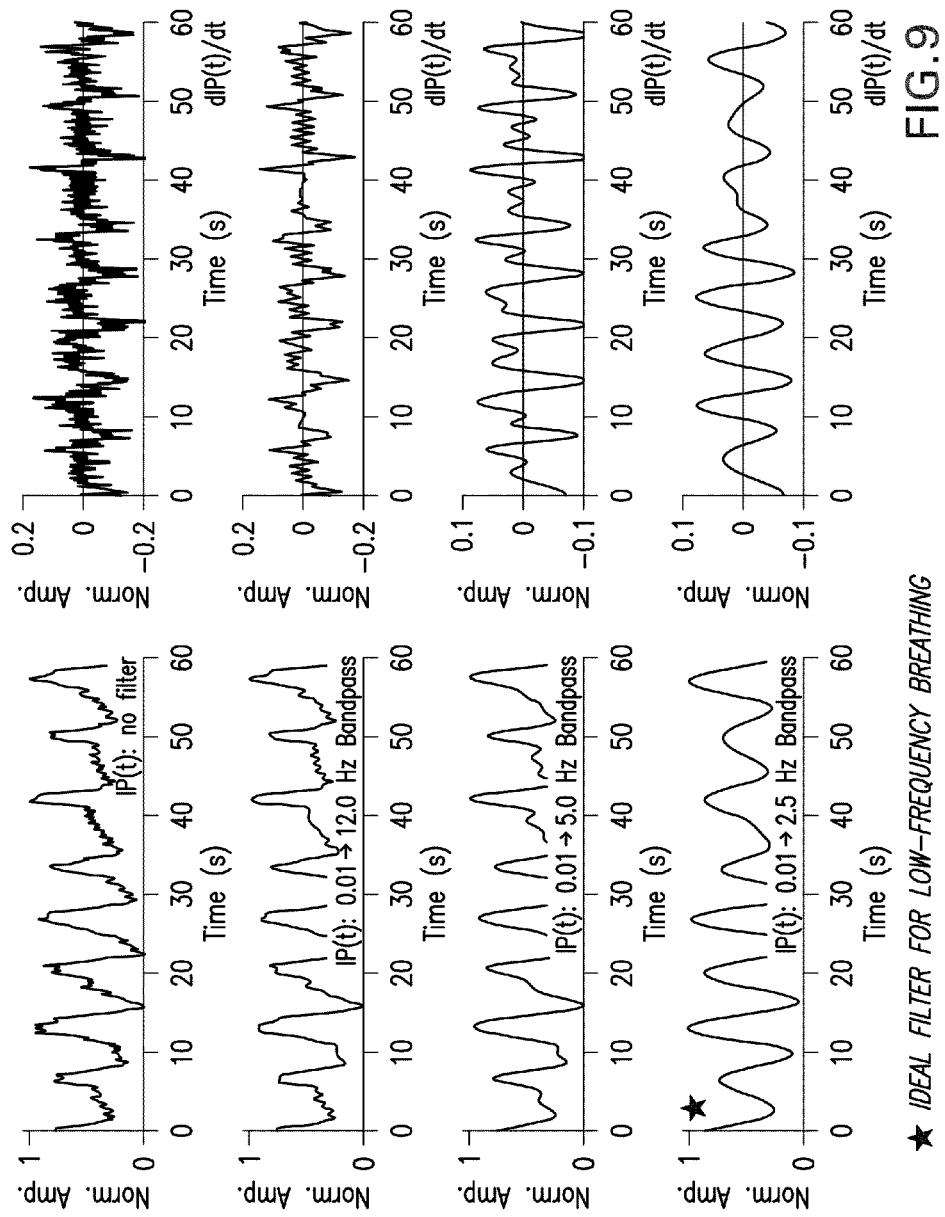
FIG. 9 shows a series of time-dependent IP waveforms (left-hand side) and their corresponding mathematical derivatives (right-hand side) measured from a slowly breathing patient and processed with digital filters featuring gradually decreasing passbands.

FIG. 9 shows how filtering raw IP waveforms with different passbands ultimately affects the signal-to-noise ratio of these signals and their corresponding derivatives. Ultimately, it is these derivatives that are processed to determine RR.

Referring again to FIG. 8, the digitally filtered IP waveform is then derivatized and squared using Algorithm 1 (step 184), yielding a signal similar to that shown in the right-hand side of FIG. 9. Taking a derivative removes any low-frequency baseline components from the IP waveform, and additionally generates a clear, well-defined zero-point crossing corresponding to each peak in the IP signal. Each peak corresponds to each respiration event. The derivative used for this calculation is typically a 5-point derivative, meaning that data point $IPP_{xi+5}$ is subtracted from data point $IPP_{xi}$ to calculate the derivative. When the IP waveform is sampled at 50 Hz, which is preferred, this means data points separated by 0.1 seconds are used for the derivative. Such a method for taking a derivative is preferred over that using directly sequential data points, i.e. a derivative where data point $IPP_{xi+1}$ is subtracted from data point $IPP_x$ (i.e. the data points are separated by 0.02 seconds for data collection rates of 50 Hz). A 5-point derivative typically yields a relatively strong signal featuring a high signal-to-noise ratio and minimal phase distortion. Additionally, as shown in FIG. 9, the passband of the digital filter has a significant impact on the derivatized signal, and features an optimal value that is closely coupled to the actual value of RR. For example, for the signals shown in FIG. 9 (corresponding to roughly 8 breaths/minute), the ideal high-frequency cutoff for the passband is near 2.5 Hz, as indicated in the figure with a star. This yields a signal where the respiratory-induced peaks can be easily processed by counting the zero-point crossing with a counting algorithm (step 186). Once determined, this initial guess at RR, along with the derivatized signal used to determine it, is compared to a series of pre-determined metrics to estimate the accuracy of the determination (step 188). In particular, the number of peaks determined during a pre-determined time period (e.g. 20 seconds) is then compared over three consecutive periods. The standard deviation (SD in FIG. 8) of the counts within these periods is then calculated using standard means, and then compared to a pre-determined value ($\beta$) to ensure that the RR is relatively constant during the measurement period. A low standard deviation, for example, would indicate that the RR is relatively constant for the three consecutive 20-second periods, which in turns indicates that the measurement is likely accurate. In contrast, a high standard deviation indicates that the RR is either changing rapidly or characterized by a waveform having a low signal-to-noise ratio, which in turn indicates that the measurement is likely inaccurate. In typical cases, $\beta$ has a value between 0-2 breaths/minute. The actual value of RR ($\omega$ in FIG. 8) is then compared to pre-determined threshold values ($\epsilon 1$ and $\epsilon 2$) to estimate if it is realistic. For example, $\epsilon 1$ represents an upper level of RR, and is typically 60 breaths/minute. At this level a patient may be hyperventilating. $\epsilon 2$ represents a lower level of RR, and is typically about 5 breaths/minute. Below this and a patient may be undergoing respiratory failure.

Figure 10:
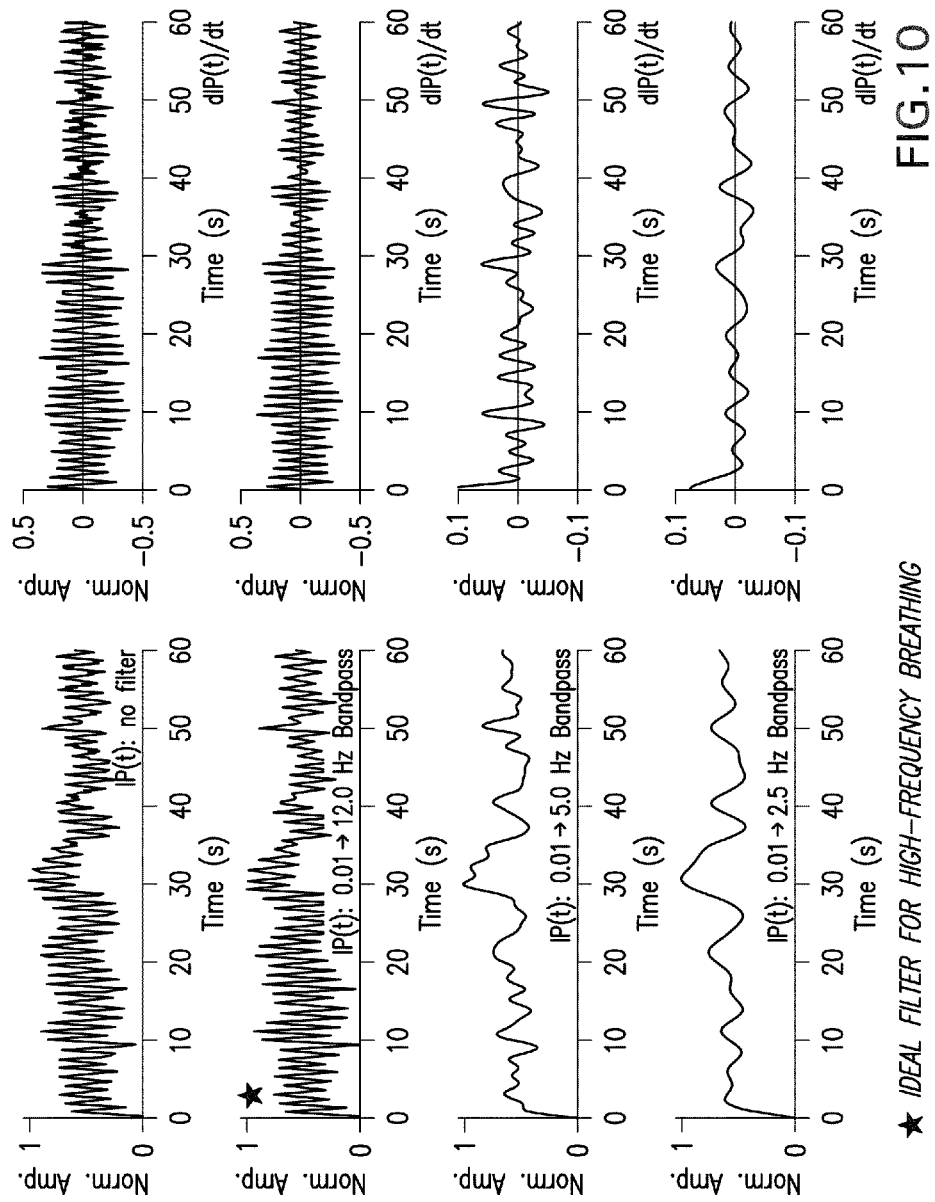
FIG. 10 shows a series of time-dependent IP waveforms (left-hand side) and their corresponding mathematical derivatives (right-hand side) measured from a rapidly breathing patient and processed with digital filters featuring gradually decreasing passbands.

If the RR value calculated during steps 180-186 meets the criteria defined in step 188, it is considered to be valid, or 'true' (T in FIG. 8), and is reported by the body-worn monitor. In contrast, if the RR value fails the criteria defined in step 188, it is assumed to be 'false' (F in FIG. 8), and further processing is performed. In particular, the raw IP waveform is processed again with a digital bandpass filter characterized by a different passband (step 190) which is typically 12 Hz. The second filter may yield a waveform featuring high-frequency components that are removed by the first filter. After this filtering step the calculations originally performed during steps 184, 186, 188 are repeated. FIG. 10 indicates the merits of processing the raw IP waveform with a digital filter having an increase passband. In this case, the patient is undergoing a high RR (roughly 60 breaths/minute), with each sharp pulse in the IP waveform composed of a large and far-ranging collection of frequency components. Thus, filtering this waveform with the 2.5 Hz digital filter described in step 182 and shown in the lower portion of FIG. 10 yields a filtered IP waveform wherein the breathing-induced pulses are depleted. Taking the derivative of this signal yields the waveform shown in the lower right-hand portion of FIG. 10. The waveform lacks the information to properly determine RR. In contrast, as indicated in FIG. 10 by a star, digitally filtering the raw IP waveform with a 12 Hz passband yields a relatively noise-free signal from which a derivatized waveform can be determined as described above (step 192). From this waveform, zero-point crossings, each corresponding to an individual breath, can be easily counted as used to estimate a value of RR (step 194). This value is then compared to the same pre-determined values ($\beta$, $\epsilon 1$, $\epsilon 2$) used during step 188 to estimate the validity of the calculated RR (step 196). If determined to be accurate, this value is reported by the body-worn monitor as described above; if not, the algorithm determines that an accurate measurement cannot be made, a series of dashes (e.g. '---') are rendered by the monitor, and the process is repeated.

Algorithms 2 and 3—Adaptive Filtering

Both Algorithms 2 and 3 describe methods for determining RR from ACC and IP waveforms using a technique called 'adaptive filtering'. The general premise of adaptive filtering, as used in this application, is that motion-induced frequency components in the ACC waveform are determined and then filtered from the simultaneously measured IP waveform. This yields a clean, relatively uncorrupted waveform from which RR can be accurately determined. In Algorithm 2, the coefficients for adaptive filtering are determined from the ACC waveform by processing performed on the wrist-worn transceiver. This may be computationally 'expensive', and thus increase power consumption, but has the added benefit that all calculations can be done in the absence of a remote server. In Algorithm 3, both IP and ACC waveforms are transmitted to the remote server following a measurement, and the coefficients for adaptive filtering are calculated on this platform. Afterwards, they are sent back to the wrist-worn transceiver, where the calculation is completed. Alternatively, the waveforms are fully processed on the remote server with adaptive filtering, and values of RR are transmitted back to the wrist-worn transceiver. In both cases, once received, the values of RR are displayed and availed for any follow-on alarming/alerting applications.

Figure 11:
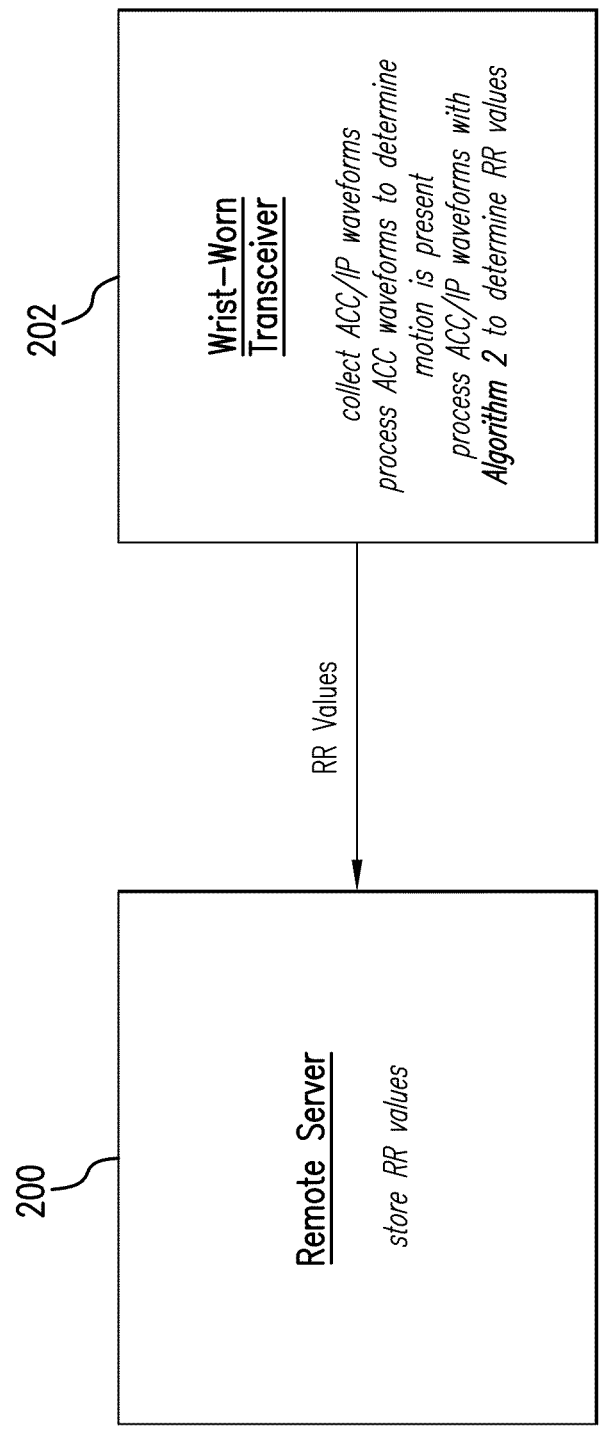
FIG. 11 shows a schematic drawing of Algorithm 2 used in the multi-component algorithm of FIG. 6 to calculate RR.

FIG. 11 provides a high-level overview of Algorithm 2, which features a wrist-worn transceiver 202 that collects ACC and IP waveforms, processes the IP waveforms to determine that motion is present, and then collectively processes the ACC and IP waveforms with an adaptive filter algorithm to determine RR. Once calculated, this parameter is wirelessly transmitted to a remote server 200 for storage and further processing. During Algorithm 3, shown schematically in FIG. 12, the wrist-worn transceiver 212 collects ACC and IP waveforms, and wirelessly transmits these to the remote server 210 for processing. The remote server determines adaptive filter parameters as described in detail below, and then wirelessly transmits these back to the transceiver 212, which uses them to digitally filter the IP waveform to determine RR in the presence of motion. Once determined, the value of RR is transmitted from the transceiver 212 to the server 210 for storage and follow-on analysis.

Figure 12:
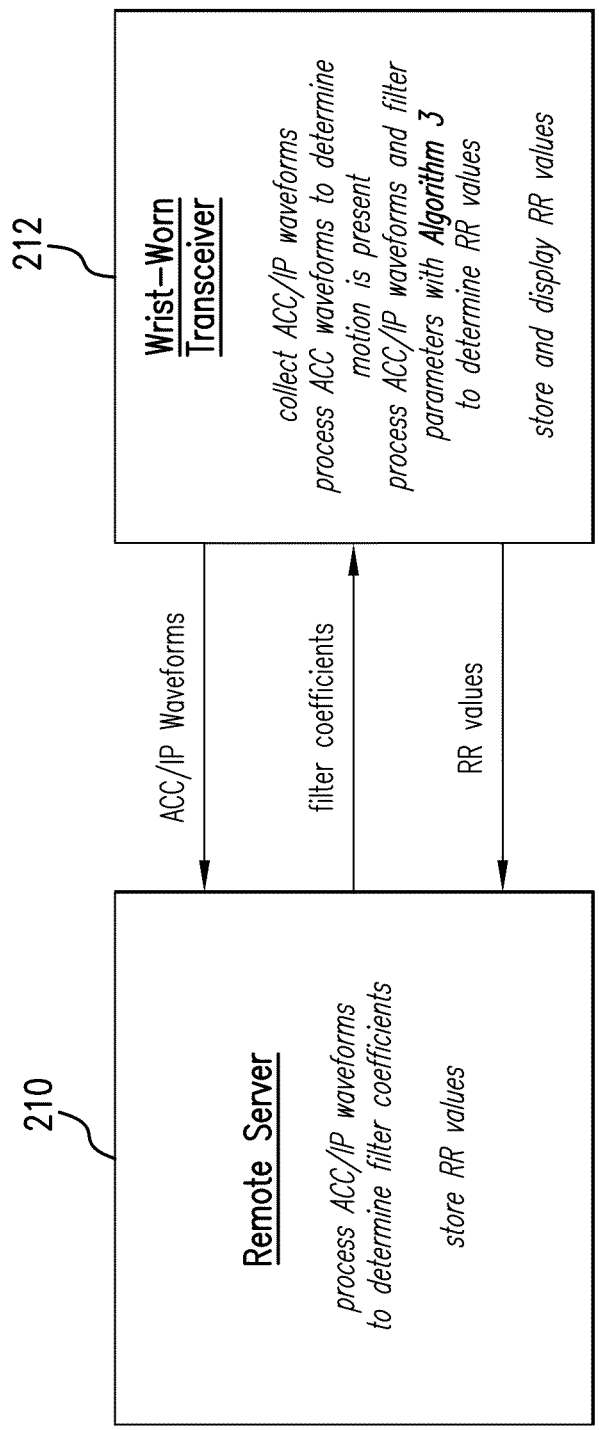
FIG. 12 shows a schematic drawing of Algorithm 3 used in the multi-component algorithm of FIG. 6 to calculate RR.

According to Algorithm 3, the coefficients determined by the remote server 210 can be continuously used by the wrist-worn transceiver 212 for an extended, follow-on period to adaptively filter IP waveforms. This further increases computational efficiency and reduces power consumption on the transceiver. Typically the follow-on period is several minutes, and preferably the motion during this period is similar in type and magnitude to that used when the coefficients were originally calculated. This ensures that motion can be adequately filtered out from the IP waveform. If the type or magnitude of the patient's motion changes, both IP and ACC waveforms are retransmitted from the transceiver 212 to the remote server 210, and the process illustrated in FIG. 12 is repeated.

Figure 13:
FIG. 13 shows a schematic drawing of computation steps used in Algorithms 2 and 3 to calculate RR.

FIG. 13 describes a general algorithm for adaptive filtering which can be used for both Algorithm 2 and/or 3. Both algorithms rely on a 'batch process' technique, which is designed for a linear deterministic system, and uses the ACC waveforms measured from the chest-worn accelerometer (component 12 in FIG. 1) as a reference signal. In alternate embodiments, this approach can be replaced with more sophisticated models, such as those involving recursive methods or non-linear deterministic systems. As described above, both Algorithms 2 and 3 begin with a determination that the patient is moving (e.g. moving their arms or legs), but not walking (step 220). The body-worn monitor then measures ACC and IP waveforms (step 222), and then the adaptive filter coefficients are determined (step 224) on either the wrist-worn transceiver (Algorithm 2) or the remote server (Algorithm 3). Once determined, the coefficients are used to adaptively filter the IP waveform to remove any motion-induced noise (step 226), resulting in a relatively noise-free waveform that is uncorrupted by motion and other noise (e.g. that from electrical and mechanical sources). At this point the waveform is processed in a manner similar to that described with reference to Algorithm 1. Specifically, the waveform is derivatized and squared (step 228) to remove any low-frequency baseline components and generate a zero-point crossing for each respiratory-induced pulse. The algorithm then counts the zero-point crossings (step 230) to determine an initial RR, which is then compared to the pre-determined values ($\beta$, $\epsilon 1$, $\epsilon 2$) described above to estimate if this rate is valid.

Figure 14:
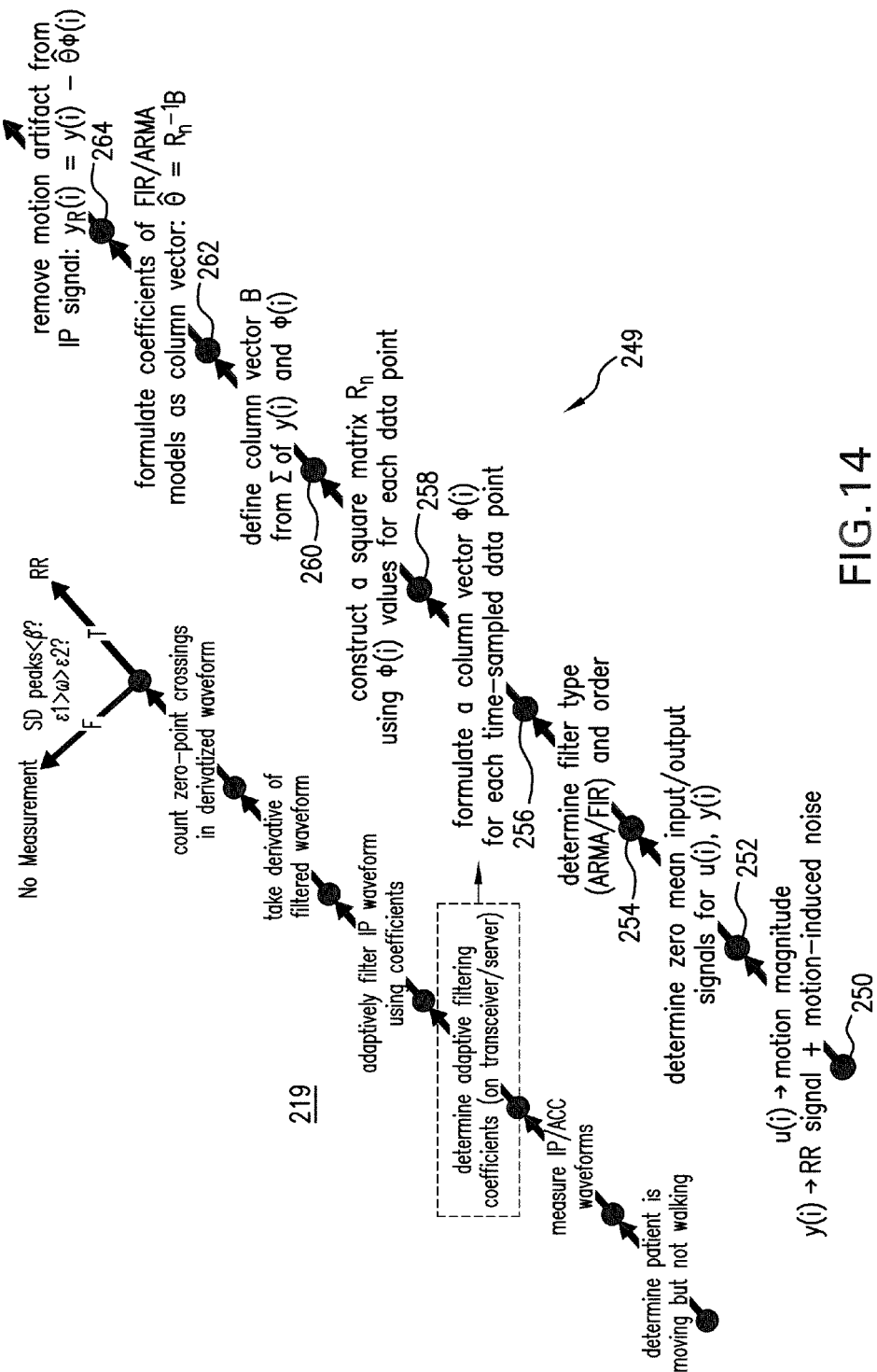
FIG. 14 shows a schematic drawing of a flow chart of computation steps used to calculate coefficients for adaptive filtering which are used in Algorithms 2 and 3 to calculate RR.

FIG. 14 highlights an algorithm 249 for determining the adaptive filtering coefficients, and for performing an adaptive digital filter. Prior to implementing the algorithm, IP and ACC waveforms from the x, y, and z-axes are collected at a frequency of 50 Hz for a period ranging from about 2-3 minutes, resulting in N samples as defined below. During this period it is assumed that the patient is undergoing moderate motion, and that the IP waveform contains a motion artifact.

The noise reference u[i] is defined as the vector length of the chest acceleration, as determined with the accelerometer mounted on the patient's chest, which combines all three axes into a single parameter as given in Eq. 1 below (step 250).

$$u[i] = \sqrt{(acc_{Cx}[i])^2 + (acc_{Cy}[i])^2 + (acc_{Cz}[i])^2} \quad (1)$$

The measured output y[i] is the IP waveform, which contains signals due to both respiration and motion. Note that for this calculation the two waveforms should be sampled at the same rate. If the IP waveform is sampled at a higher frequency than that used for the ACC waveform (e.g. 50 Hz), then this waveform must be converted into a 50 Hz waveform using conventional mathematical techniques, such as decimation or a numerical 'mapping' operation.

At this point zero mean input and output signals for u[i] and y[i] are constructed by subtracting the ensemble signal mean from each signal. This operation, shown below in Eqs. 2 and 3, effectively removes any DC offset (step 252).

$$u[i] = u[i] - \left(\frac{1}{N}\right)\sum_{k=1}^{N} u[k] \quad (2)$$

$$y[i] = y[i] - \left(\frac{1}{N}\right)\sum_{k=1}^{N} y[k] \quad (3)$$

A mathematical model used to define the impulse response function of the adaptive filter must be chosen, with the two primary options being filters based on FIR (finite impulse response) or ARMA (autoregressive moving average) models. Both models are indicated below in Eqs. 4 and 5, but only one should be chosen and implemented during the algorithm (step 254):

FIR Model $$H[z] = b_0 + b_1 z^{-1} + \ldots + b_L z^{-L} \quad (4)$$

ARMA Model $$H[z] = \frac{b_0 + b_1 z^{-1} + \ldots + b_m z^{-m}}{1 + a_1 z^{-1} + \ldots + a_n z^{-p}} \quad (5)$$

At this point the order of the filter is determined. For the FIR model, the order is L; for the ARMA model, the order is m and p. In a preferred embodiment, the orders for L, m, and p are, respectively, 25, 2, and 2; these values may vary depending on the degree of motion and the computational capabilities on the wrist-worn transceiver. A column vector phi $\phi[i]$ is then formulated for each time-sampled data point for both the FIR and ARMA models, as described in Eqs. 6 and 7 below (step 256). In these equations the superscript T represents the matrix transpose.

FIR Model $$\phi[i] = [u[i]u[i-1]u[i-2]u[i-3] \ldots u[i-25]]^T \quad (6)$$

ARMA Model $$\phi[i] = [u[i]u[i-1]u[i-2]-y[i-1]-y[i-2]]^T \quad (7)$$

The square matrix $R_N$ is then constructed using the column vectors defined above, as shown in Eqs. 8 and 9 (step 258):

FIR Model $$R_N = \sum_{i=L+1}^{N} \varphi[i]\varphi^T[i] \quad (8)$$

ARMA Model $$R_N = \sum_{i=p+1}^{N} \varphi[i]\varphi^T[i] \quad (9)$$

The column vector B is then defined from the measured output, y[i] and column vector, $\phi[i]$, as defined below in Eqs. 10 and 11 (step 260):

FIR Model $$B = \sum_{i=L+1}^{N} y[i]\varphi[i] \quad (10)$$

ARMA Model $$B = \sum_{i=p+1}^{N} y[i]\varphi[i] \quad (11)$$

At this point the coefficients of the FIR and ARMA models can be written as a column vector, $\theta$, as given below in Eqs. 12 and 13:

FIR Model $$\theta = [b_0 b_1 b_2 \ldots b_L]^T \quad (12)$$

ARMA Model $$\theta = [b_0 b_1 b_2 a_1 a_2]^T \quad (13)$$

The square matrix and two column vectors obey the relationship given below in Eq. 14 for the adaptive filtering process.

$$R_N \theta = B \quad (14)$$

The adaptive filtering coefficients for each model can be identified from the data using the expression below in Eq. 15, where the accented column vector $\hat{\theta}$ represents the identified coefficients (step 262):

$$\hat{\theta} = R_N^{-1} B \quad (15)$$

Once identified, the filter coefficients can be collectively processed with the IP waveform and used to remove any motion artifacts, leaving only the respiratory component of the signal $y_R[i]$, as shown below in Eq. 16 (step 264):

$$y_R[i] = y[i] - \hat{\theta}\phi[i] \quad (16)$$

As described above, determination of the filter coefficients can be done on either the wrist-worn transceiver (Algorithm 2) or on the remote server (Algorithm 3). Once determined, the coefficients can be used to recover RR in real-time using the algorithm described above. Preferably the filter coefficients are updated when analysis of the ACC waveform indicates that the patient's motion has changed. Such a change can be represented by a change in the magnitude of the motion, a change in posture, or a change in activity state. Alternatively, the filter coefficients can be updated on a periodic basis, e.g. every 5 minutes.

There may be a time difference or delay between motion signals in the ACC waveform, and motion artifacts in the IP waveform. Such a delay, for example, may be due to real phenomena (e.g. a physiological effect) or an artifact associated with the electrical systems that measure the respective waveforms (e.g. a phase delay associated with an amplifier or analog filter that processes these waveforms). In any event, the algorithm should compensate for the delay before performing calculations shown in Eqs. 1-16, above. Such compensation can be performed using a simple time-domain analysis of ACC and IP signals influenced by a well-defined motion (e.g. a step). Alternatively, the compensation can be done during manufacturing using a one-time calibration procedure.

Figure 15A:
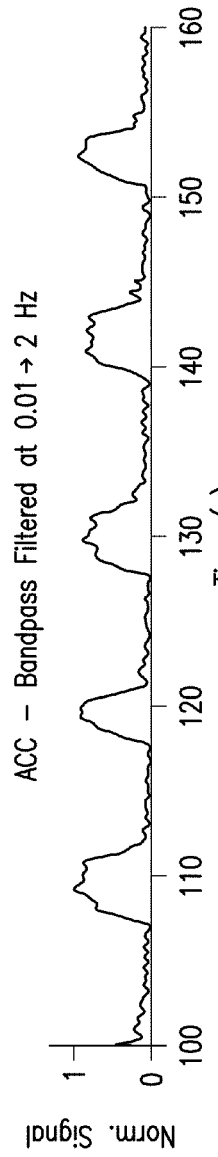
Figure 15B:
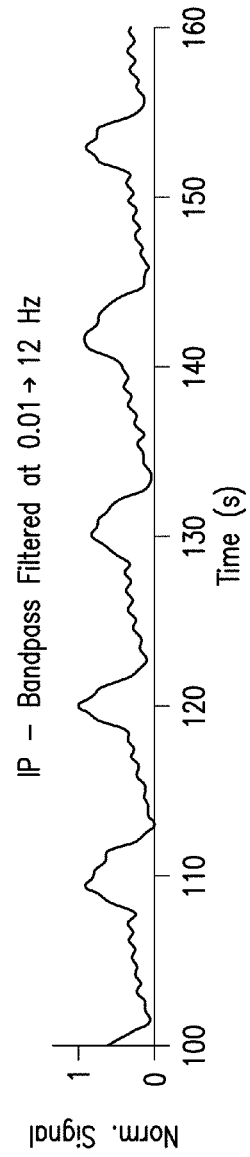
Figure 15C:
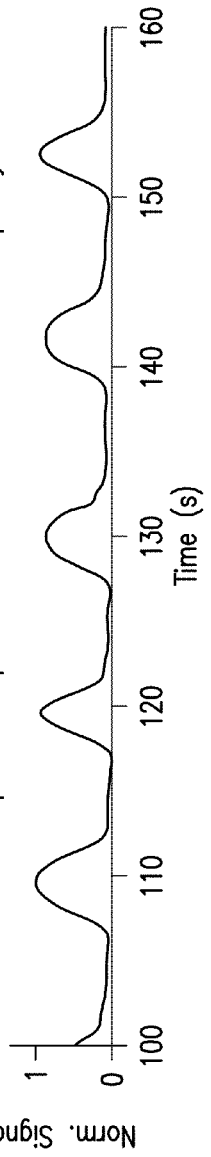

FIGS. 15, 16, and 17 illustrate how the above-described adaptive filtering algorithm can be applied to both ACC and IP waveforms. In each of the figures, the graphs show the ACC waveform filtered with an initial, non-adaptive filter (15A, 16A, 17A; 0.01→2 Hz bandpass), and the IP waveform filtered under similar conditions with a slightly larger bandpass filter (15B, 16B, 17B; 0.01→12 Hz bandpass). Typically the IP waveform is filtered with the larger bandpass so that high-frequency components composing the rising and falling edges of pulses within these waveforms are preserved.

Once filtered, the IP waveform is processed as described above to determine an initial RR. This value may include artifacts due to motion, electrical, and mechanical noise that erroneously increases or decreases the initial RR value. But typically such errors have little impact on the final RR value that results from the adaptive filter. The middle graph (FIGS. 15C, 16C, and 17C) in each figure show the IP waveform processed with the adaptive filter. In all cases this waveform features an improved signal-to-noise ratio compared to data shown in the top graph (15A, 16A, 17A), which is processed with a non-adaptive (and relatively wide) filter. Typically the narrow bandpass on the adaptive filter removes many high-frequency components that contribute the sharp rising and falling edges of pulses in the ACC waveforms. This slightly distorts the waveforms by rounding the pulses, giving the filtered waveform a shape that resembles a conventional sinusoid. Such distortion, however, has basically no affect on the absolute number of pulses in each waveform which are counted to determine RR.

Figures 16D, 16E, 16F:
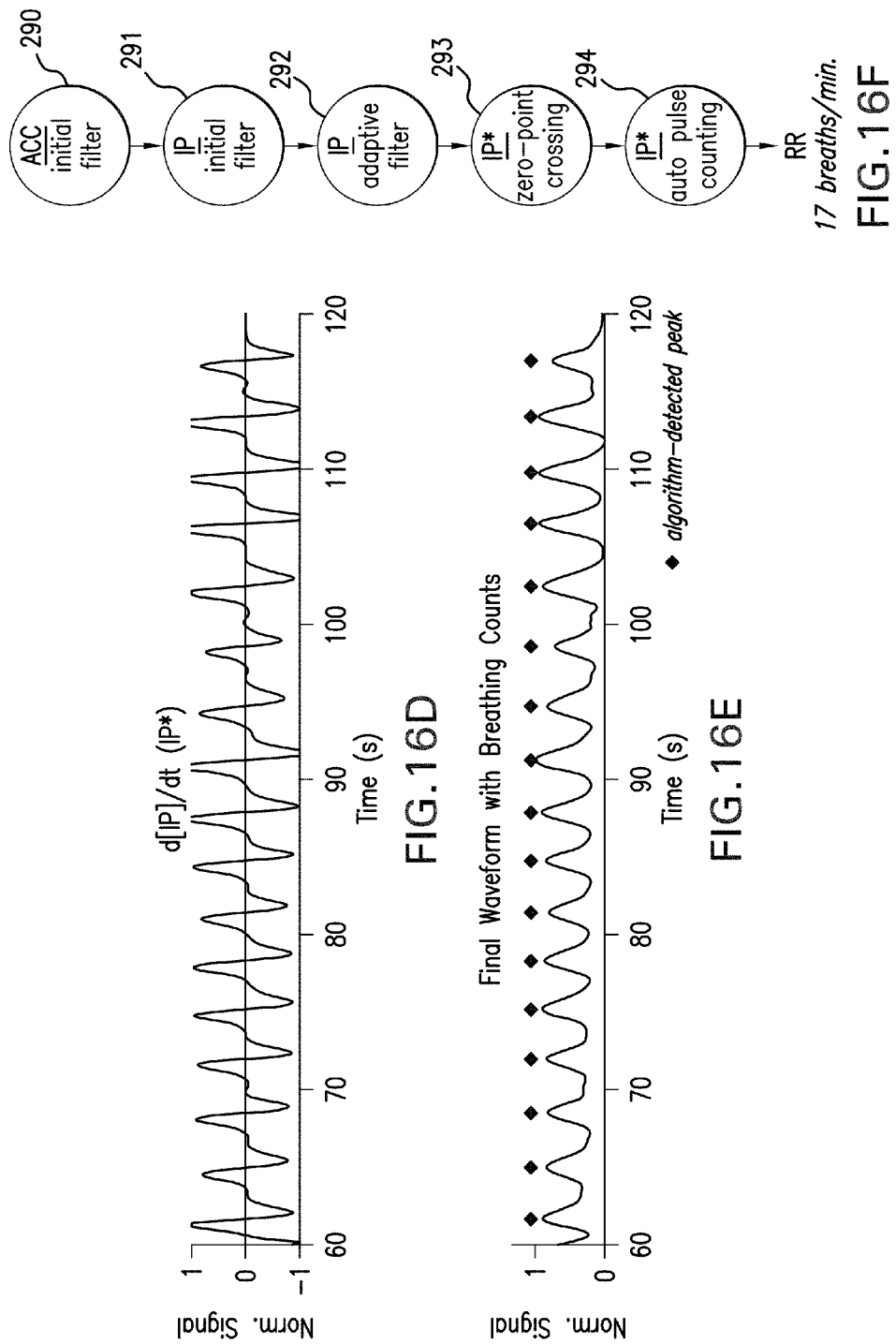
Figure 17A:
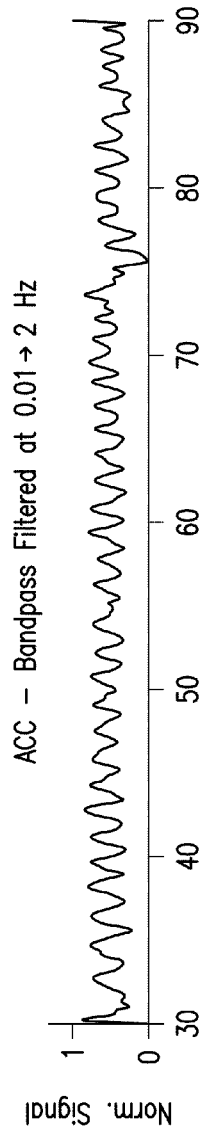
FIGS. 17A-E show graphs of an ACC waveform filtered initially with a 0.01→2 Hz bandpass filter (FIG. 17A; top), an IP waveform filtered initially with a 0.01→12 Hz bandpass (FIG. 17B), an IP waveform adaptively filtered with a bandpass filter ranging from 0.01 Hz to 1.5 times the breathing rate calculated from the ACC waveform in FIG. 17A (FIG. 17C), a first derivative of the filtered IP waveform in FIG. 17C (FIG. 17D), and the adaptively filtered IP waveform in FIG. 17C along with markers indicating very fast, deep breaths as determined from the algorithm shown by the flow chart in FIG. 14 (FIG. 17E; bottom)
Figure 17B:
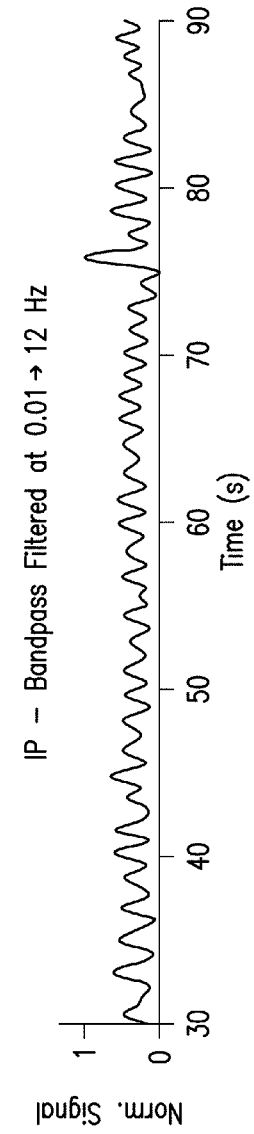
Figure 17C:
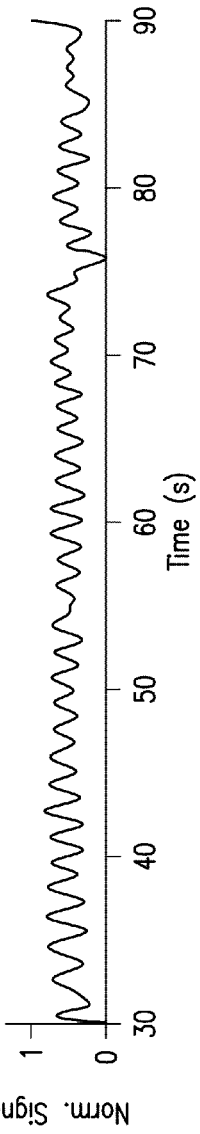
Figure 17F:
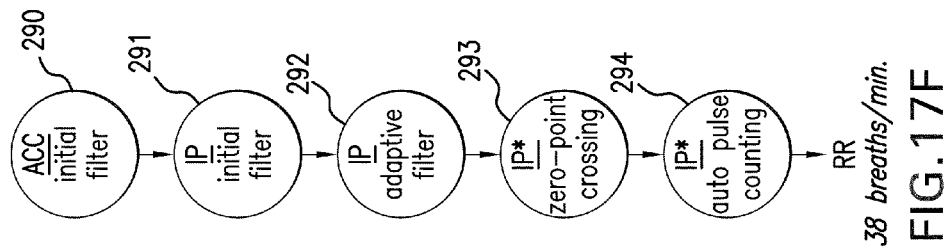
FIG. 17F is a flow chart showing the algorithmic steps used to process the waveforms shown in FIGS. 17A-E.
Figure 17D:
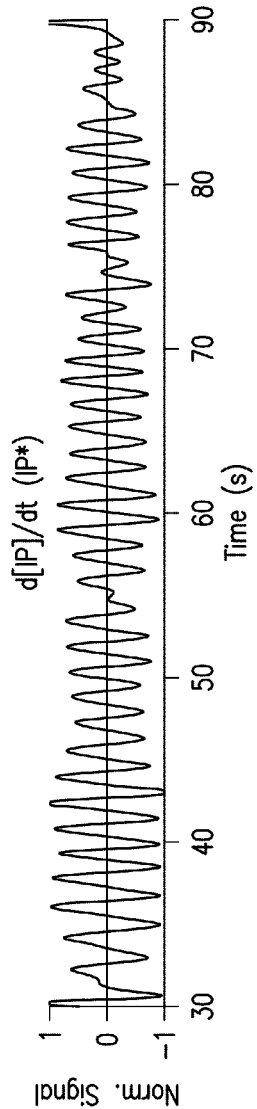
Figure 17E:
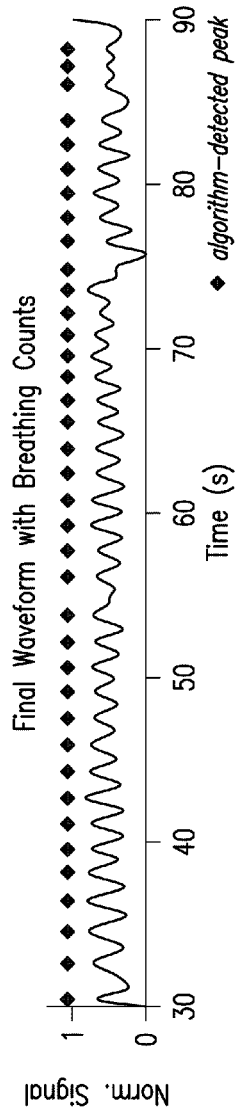

The adaptively filtered IP waveform is then derivatized and graphed in FIGS. 15D, 16D, and 17D. This waveform is then processed with the above-mentioned signal processing techniques, e.g. squaring the derivative and filtering out lobes that fall beneath pre-determined threshold values, to yield an algorithm-determined 'count', indicated in FIGS. 15E, 16E, and 17E as a series of black triangles. The count is plotted along with the adaptively filtered IP waveforms from FIGS. 15C, 16C, and 17C. Exact overlap between each pulse in the waveform and the corresponding count indicates the algorithm is working properly. Data from each of the figures correspond to varying respiratory behavior (5, 17, and 38 breaths/minute in, respectively, FIGS. 15, 16, and 17), and indicate that this technique is effective over a wide range of breathing frequencies. The right-hand side of the figures (FIGS. 15F, 16F, and 17F) show a series of steps 290-294 that indicate the analysis required to generate the corresponding graphs in the figure.

Algorithm 4—Power Spectra Analysis

FIG. 18 shows a high-level overview of Algorithm 4, which is typically used to remove motion-related artifacts having relatively large magnitudes, such as those associated with running and walking, from the IP waveform. Algorithm 4 deconstructs both time-domain ACC and IP waveforms into their frequency-domain components, and then collectively processes these components to remove artifacts due to motion. Typically this algorithm involves collecting the two waveforms on the wrist-worn transceiver 302, and then processing them with the algorithms described above to determine if motion is present. If it is, the waveforms are wirelessly transmitted to the remote server, where they are processed with the algorithm described below to determine and then collectively process their frequency spectra to remove the affects of motion. RR is determined on the server, where it is stored, further processed, and finally sent to the wrist-worn transceiver 302 for purposed related to display and alarming.

Figure 19:
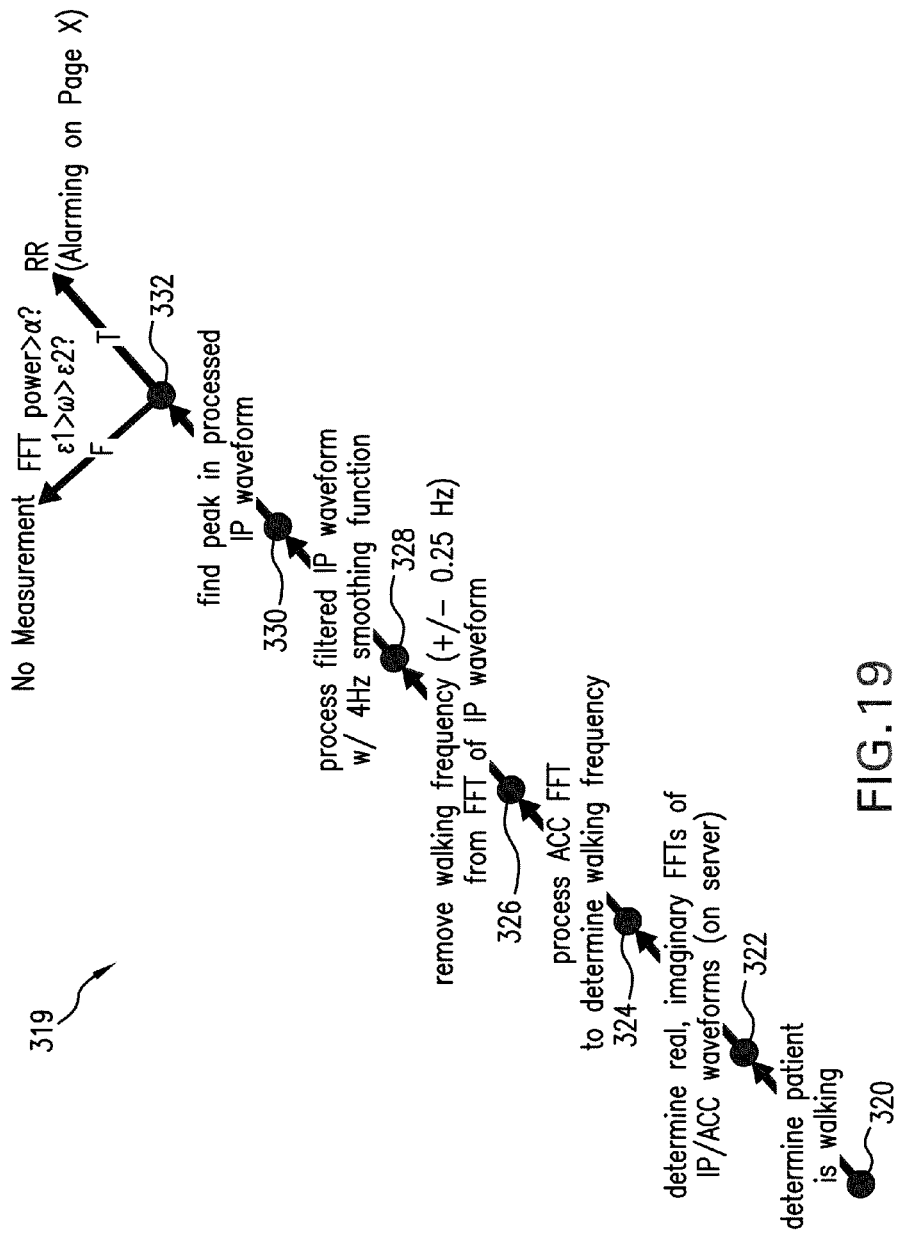
FIG. 19 shows a schematic drawing of computation steps used in Algorithm 4 to calculate RR.

FIG. 19 shows the computational details of Algorithm 4. The algorithm begins by determining if the patient is walking or running (step 320). This is done by processing ACC waveforms according to the techniques described in the above-described patent application, the contents of which are incorporated herein by reference. Once the patient's walking or running state is identified, the ACC and IP waveforms (represented in Eq. 17 by a(t)) are wirelessly transmitted to the remote server, which then determines their frequency-domain power spectra A($\omega$), as defined by Eq. 17 (step 322):

$$A(\omega) = \left[\frac{1}{\sqrt{2\pi}} \int_{-\infty}^{\infty} a(t)e^{-i\omega t}dt\right]^2 \quad (17)$$

A($\omega$) shown above in Eq. 17 represents a power spectra determined from a continuous Fourier Transform. For discrete waveforms featuring an array of discrete values $a_n$, like the ones measured with the body-worn monitor, A($\omega$) can be rewritten as:

$$A(\omega) = \left[\frac{1}{\sqrt{2\pi}} \sum_{n=-\infty}^{n=+\infty} a_n e^{-i\omega t}dt\right]^2 \quad (18)$$

or alternatively as:

$$A(\omega) = \frac{F(\omega)F^*(\omega)}{2\pi} \quad (19)$$

Where F($\omega$) is the discrete Fourier Transform and F*($\omega$) is its complex conjugate. Power spectra determined this way for both IP and ACC waveforms are shown, for example, in FIGS. 20C, 20D, 21C, and 21D.

The power spectra of the ACC waveform is then processed to determine a collection of frequencies corresponding to the patient's motion, which as described above corresponds to walking or running for this particular algorithm (step 324). Typically these motions are characterized by a collection of frequencies that are peaked between 0.5 and 2.0 Hz. Once the peak frequency is identified, a notch filter having a top-hat profile and a bandwidth of 0.5 Hz is constructed to surround it. Typically the primary walking frequency is positioned at the center of the notch filter, which extends 0.25 Hz on both the positive and negative ends. The notch filter is then used to process the power spectra of the IP waveform by only passing components outside of the notch (step 326). The resulting spectra of the IP waveform will now lack the frequency components related to motion. To simplify determination of the central respiratory signal, the IP waveform is then processed with a smoothing filter typically having a bandwidth of 4 Hz (step 328). Alternatively the spectrum can be processed with a rolling average. Both techniques smooth out discrete frequency components, creating a continuous set of peaks which can then be analyzed with conventional peak-finding algorithms (step 330). Examples of peak-finding algorithms include those that find the maximum frequency of each peak in the spectrum.

The frequency of the dominant peak in the filtered IP spectrum corresponds to RR. Once determined, this value and the spectrum it is extracted from can be compared to a series of pre-determined metrics to estimate the accuracy of the resulting RR (step 332). For example, the power (i.e. magnitude or density) of the peak can be compared to the metric $\alpha$ to determine if it is above a noise floor and corresponds to a level describing an actual RR. Additionally, the RR is compared to the $\epsilon 1$ and $\epsilon 2$ metrics described above to determine if the rate is within the boundaries (typically 5-60 breaths/minute) of human respiration. If so, RR is stored, further processed, and sent to the wrist-worn transceiver for display and further processing. If not, a state of 'no measurement' (indicated by dashes '---') is recorded, and the process is then repeated.

FIGS. 20 and 21 show how Algorithm 4 can effectively determine RR for a patient that is running (FIG. 20) and walking (FIG. 21). Time-domain IP and ACC waveforms for the patient, collected by the body-worn monitor, are shown respectively in FIGS. 20A and 20B. In the IP waveform, the slowly varying pulses occurring approximately every 5 seconds correspond to individual breaths, while the sharp peaks in both the ACC and IP waveforms that occur roughly twice each second corresponds to running steps. In this case, motion artifacts from the running motion clearly couple into the IP waveform.

Figure 20A:
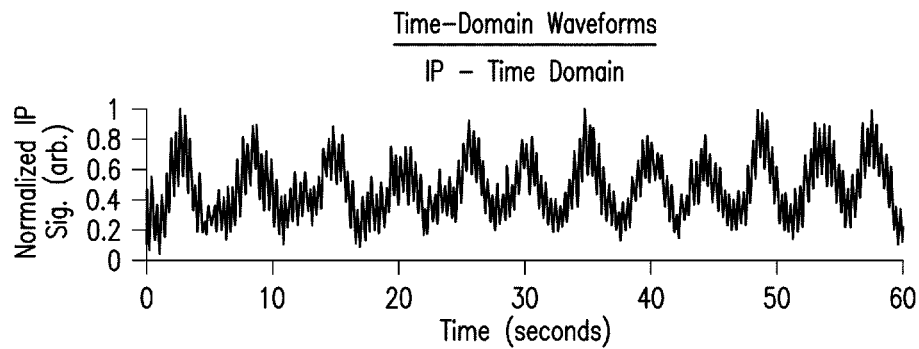
FIGS. 20A-F show, respectively, a time-domain IP waveform measured from a running patient (FIG. 20A), a time-domain ACC waveform simultaneously measured from the same patient (FIG. 20B), a frequency-domain power spectrum of the IP waveform of FIG. 20A (FIG. 20C), a frequency-domain power spectrum of the ACC waveform of FIG. 20B (FIG. 20D), the frequency-domain power spectrum of the IP waveform of FIG. 20C processed with a notch filter (FIG. 20E), and the frequency-domain power spectrum of the IP waveform of FIG. 20E processed with a smoothing filter (FIG. 20F)
Figure 20B:
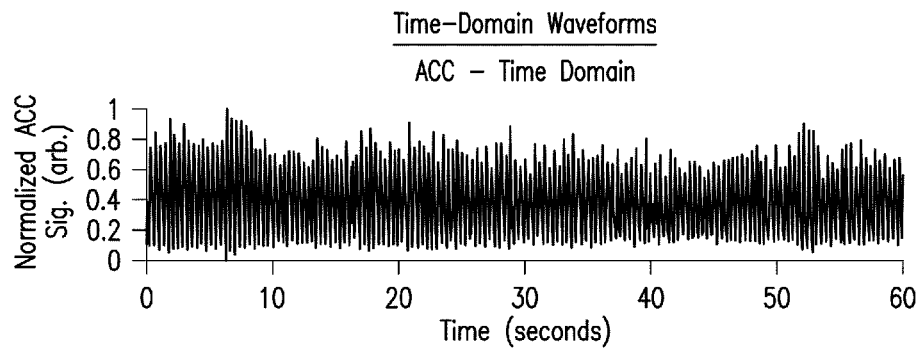
Figure 20C:
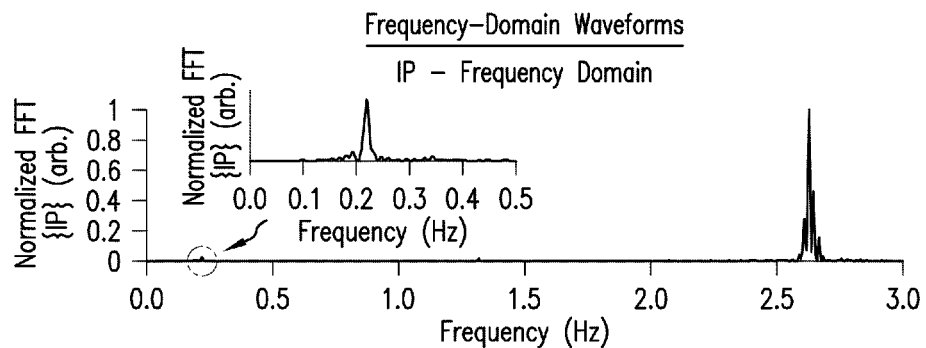
Figure 20D:
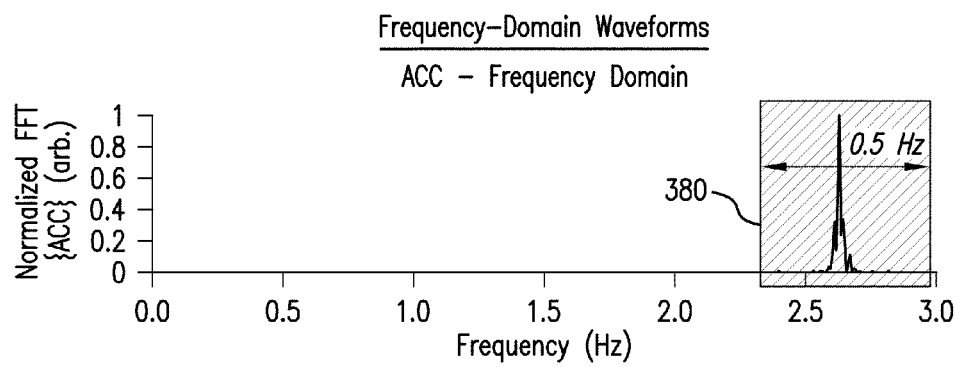
Figure 20E:
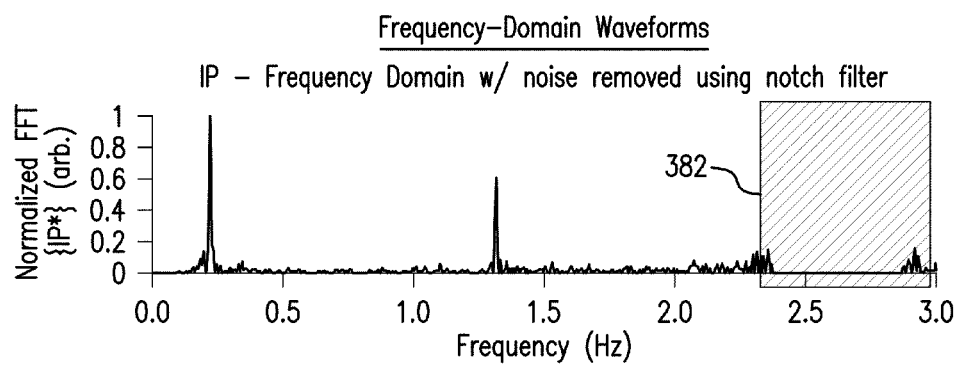

FIGS. 20C and 20D show, respectively, frequency-domain power spectra of both the IP and ACC waveforms. Clearly shown in the power spectra of the IP waveform is a dominant peak near 2.7 Hz corresponding to motion artifacts from the patient's running. A much weaker peak is also evident near 0.2 Hz. The power spectra corresponding to the ACC waveform features only a peak near 2.7 Hz that includes nearly the exact same frequency components as the corresponding peak in the IP waveform. As shown in FIG. 20D, a top-hat shaped notch filter centered at 2.7 Hz with a bandwidth of 0.5 Hz, indicated by the gray area 380, is then applied to the IP waveform. This yields the filtered waveform, shown in FIG. 20E, that lacks the high-frequency peak associated with the motion artifacts, as shown by the gray area 382. The relatively low-frequency peak near 0.2 Hz is now dominant. Further processing of this spectrum with a 4 Hz smoothing function eliminates most of the jagged edges present in FIG. 20E, yielding the continuous power spectrum shown in FIG. 20F. Processing this spectrum with a simple peak-finding algorithm yields the patient's actual RR, which corresponds to about 13 breaths/minute.

FIG. 21 shows a case where the RR and the motion artifact, in this case caused by walking, are relatively close in frequency. Here, the time-domain IP waveform shown in FIG. 21A lacks a strong, periodic respiratory signal, and is strongly corrupted by the walking-induced signals in the ACC waveform, shown in FIG. 21B. Each pulse in the ACC waveform corresponds to a unique step. The corresponding power spectra, shown in FIGS. 21C and 21D, show frequency components corresponding to both the motion artifact (near 0.75 Hz) and the respiratory signal (near 0.25 Hz). Because the respiratory signal lacks a clear, well-defined breathing pattern, the corresponding power spectrum features a range a frequencies between 0.2 and 0.5 Hz.

Figure 21A:
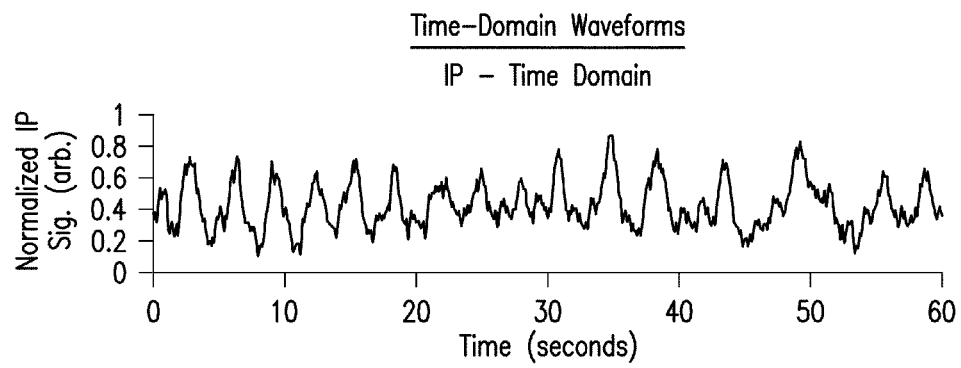
FIGS. 21A-F show, respectively, a time-domain IP waveform measured from a walking patient (FIG. 21A), a time-domain ACC waveform simultaneously measured from the same patient (FIG. 21B), a frequency-domain power spectrum of the IP waveform of FIG. 21A (FIG. 21C), a frequency-domain power spectrum of the ACC waveform of FIG. 21B (FIG. 21D), the frequency-domain power spectrum of the IP waveform of FIG. 21C processed with a notch filter (FIG. 21E), and the frequency-domain power spectrum of the IP waveform of FIG. 21E processed with a smoothing filter (FIG. 21F)
Figure 21B:
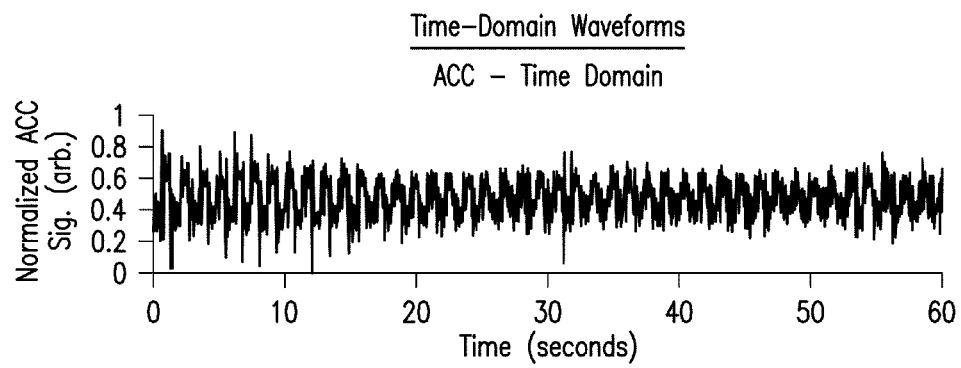
Figure 21C:
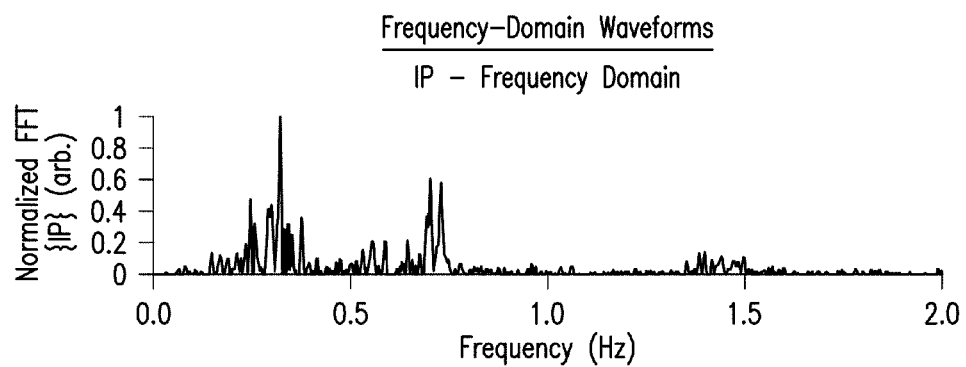
Figure 21D:
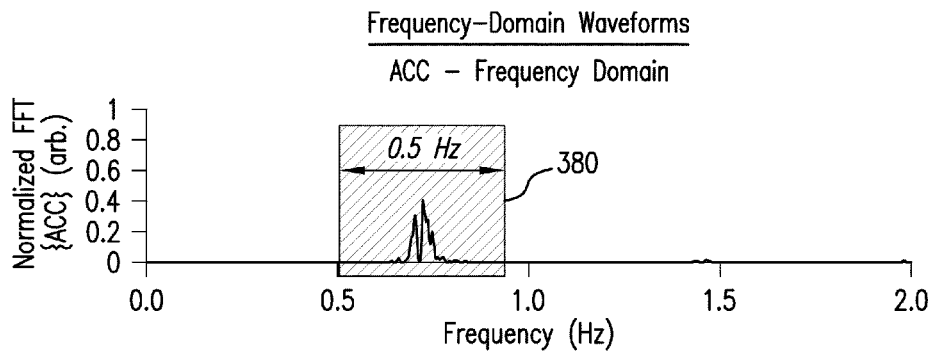
Figure 21E:
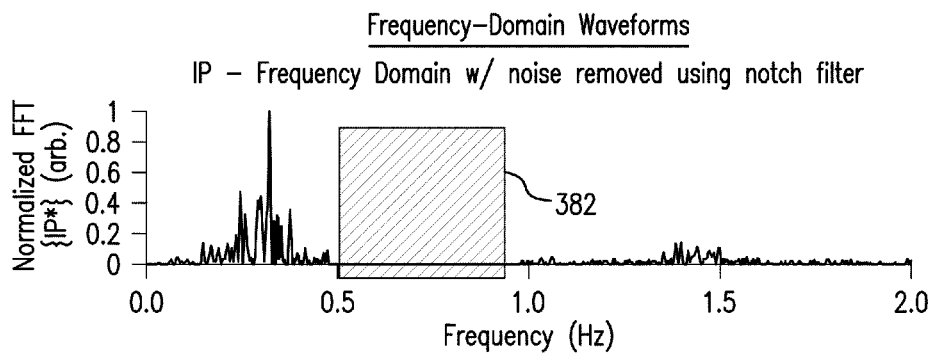

Application of the 0.5 Hz bandwidth notch filter, shown by the gray area 380 in FIG. 21D, removes motion artifacts from the IP waveform, leaving only a range of frequencies between 0.2 and 0.5 Hz. This portion of the spectrum features a large number of sharp peaks which are difficult to isolate with conventional peak-finding algorithms. However application of the 4 Hz smoothing function, as indicated by FIG. 21D, reduces this collection of frequencies to a single, broad peak shown in FIG. 21E that corresponds to the patient breathing at about 18 breaths/minute.

Figure 22C:
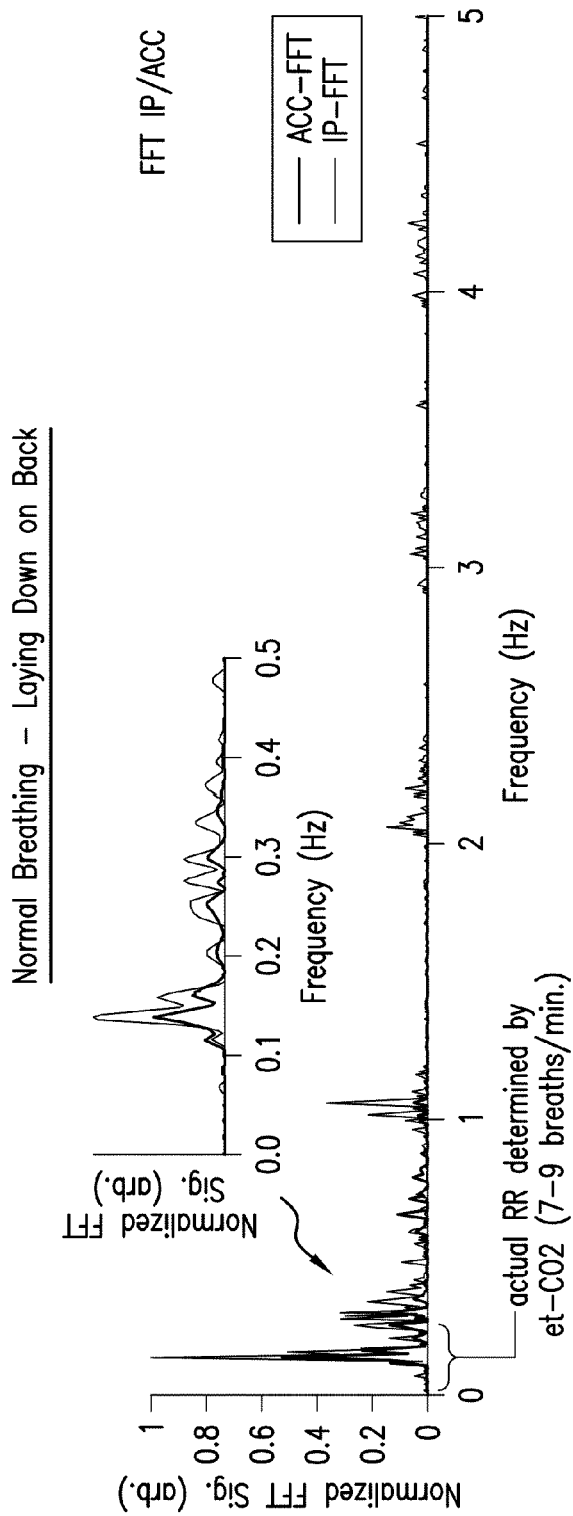
Figure 23C:
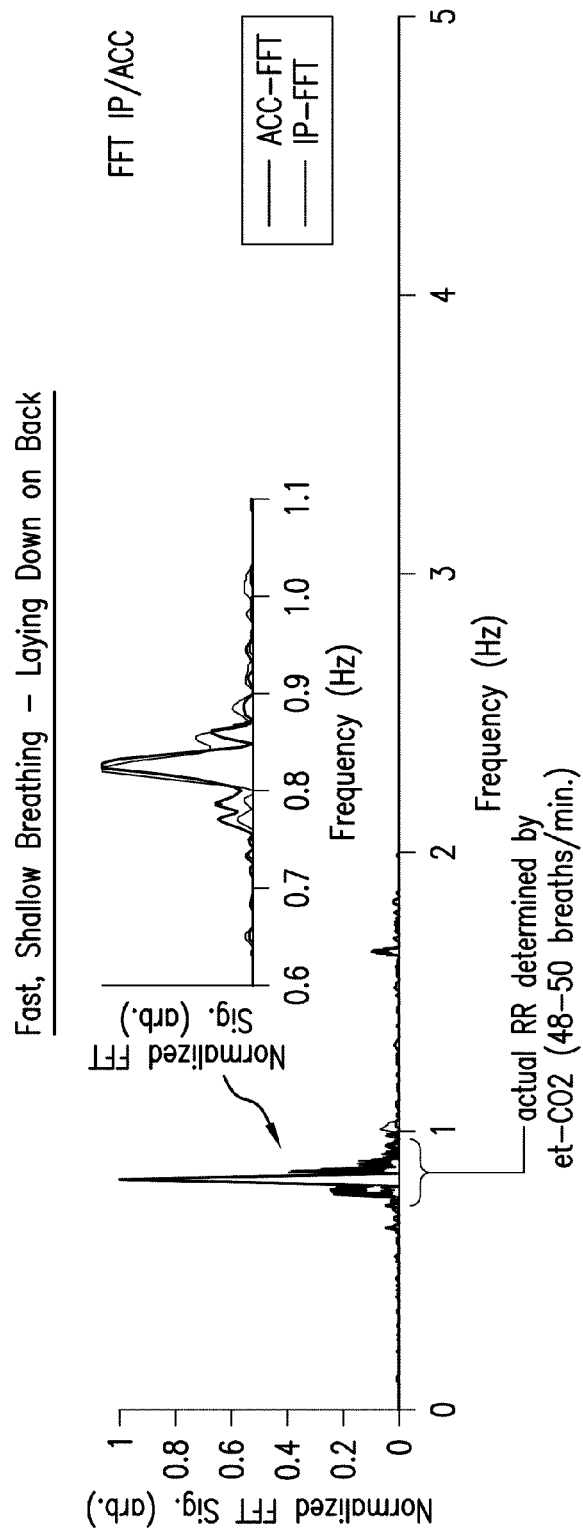
Figures 24A, 24B:
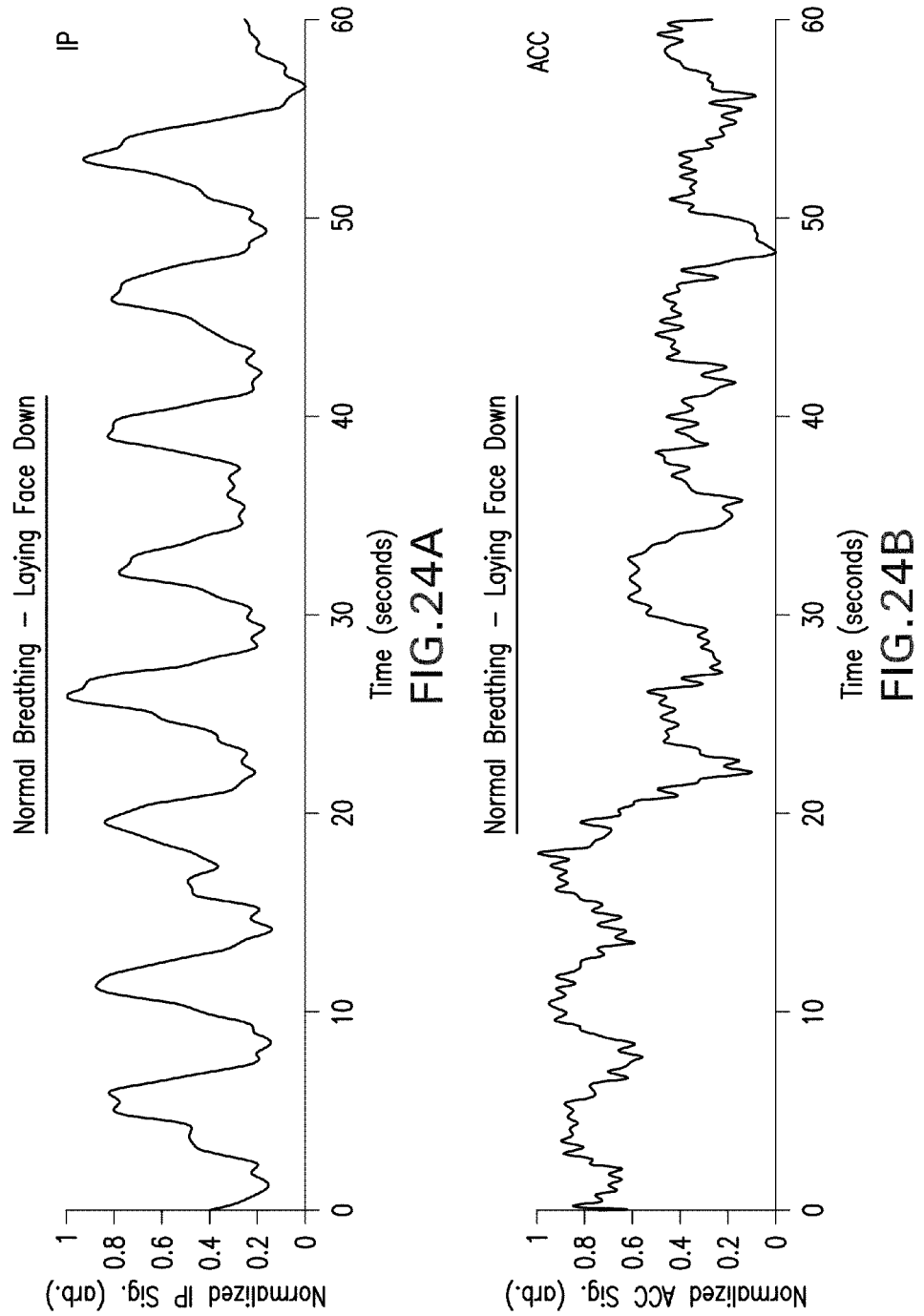
FIGS. 24A-C show, respectively, a time-domain IP waveform measured from a stationary patient laying face down and breathing normally (FIG. 24A), a time-domain ACC waveform measured simultaneously from the same patient (FIG. 24B), and frequency-domain power spectra of both the time-domain IP waveform of FIG. 24A and ACC waveform of FIG. 24B (FIG. 24C)
Figure 24C:
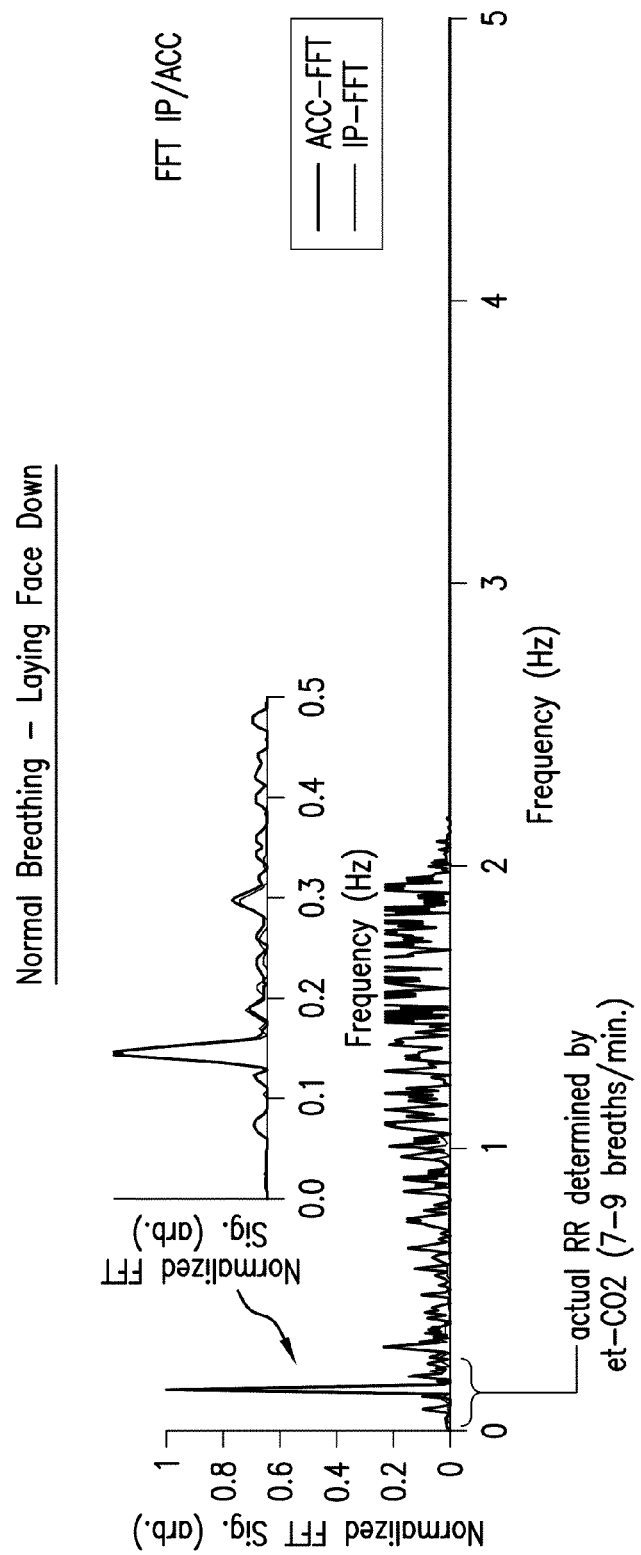
Figure 25A:
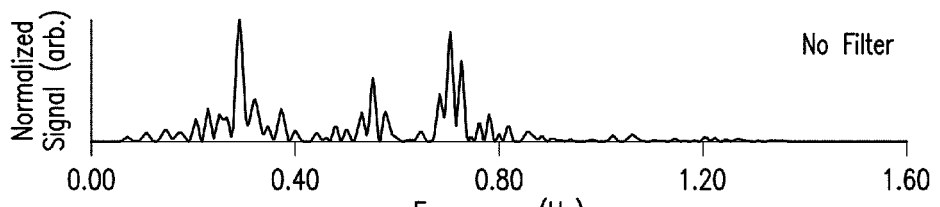
FIGS. 25A-E show frequency-domain power spectra of, respectively, an IP waveform processed with no smoothing filter (FIG. 25A), a 5.0 Hz smoothing filter (FIG. 25B), a 2.5 Hz smoothing filter (FIG. 25C), a 1.0 Hz smoothing filter (FIG. 25D), and a 0.5 Hz smoothing filter (FIG. 25E)
Figure 25B:
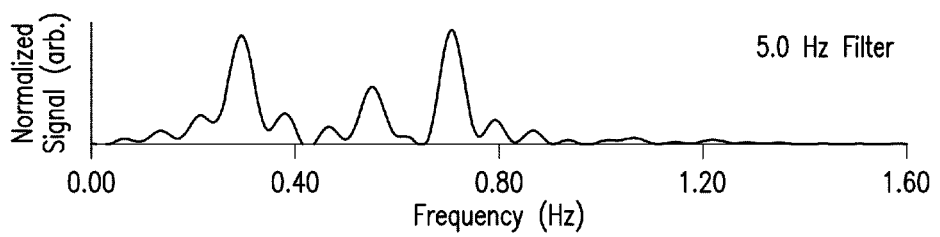
Figure 25C:
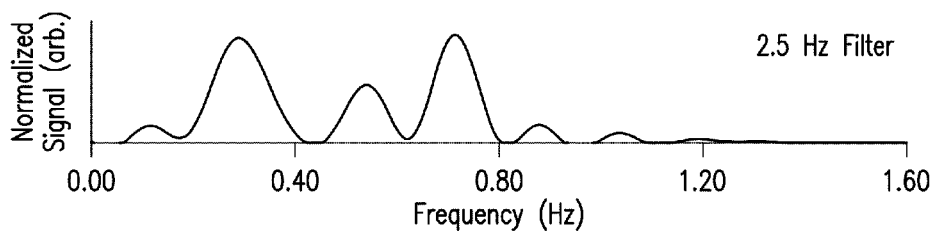
Figure 25D:
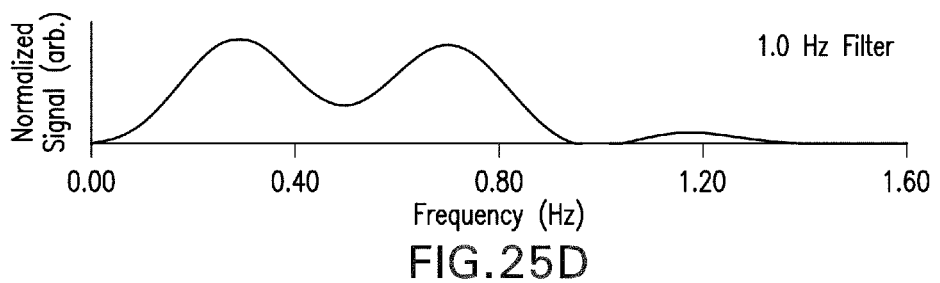
Figure 25E:
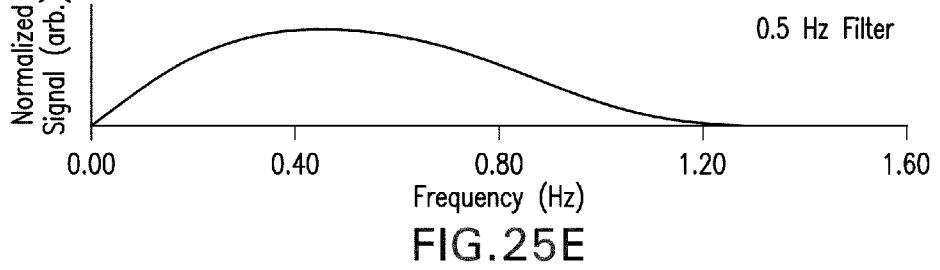
Figure 26A:
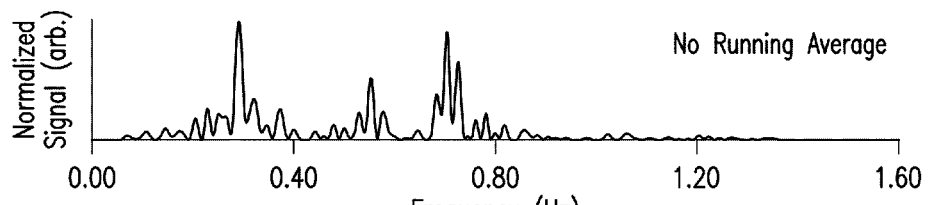
FIGS. 26A-E show frequency-domain power spectra of, respectively, an IP waveform processed with no running average (FIG. 26A), a 10-point running average (FIG. 26B), a 20-point running average (FIG. 26C), a 50-point running average (FIG. 26D), and a 100-point running average (FIG. 25E)
Figure 26B:
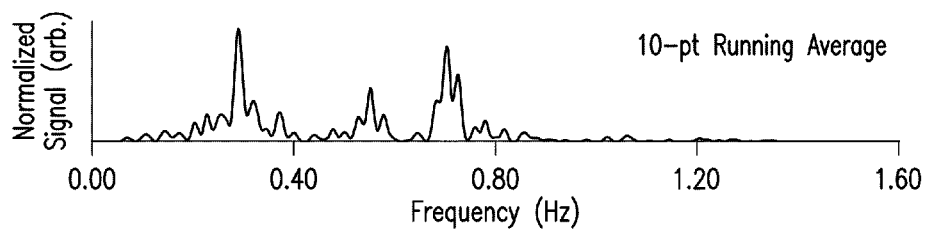
Figure 26C:
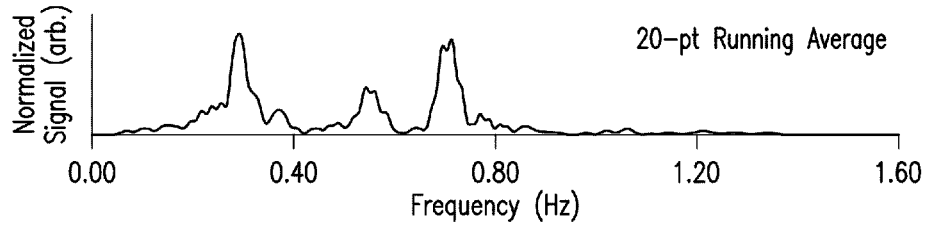
Figure 26D:
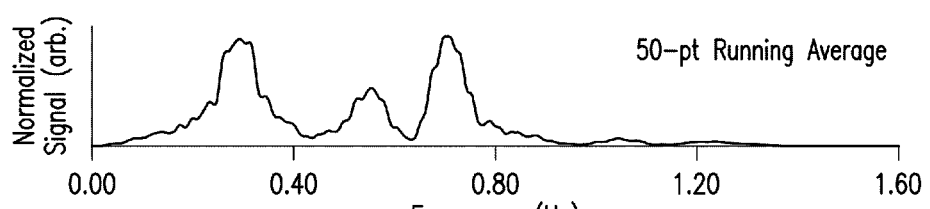
Figure 26E:
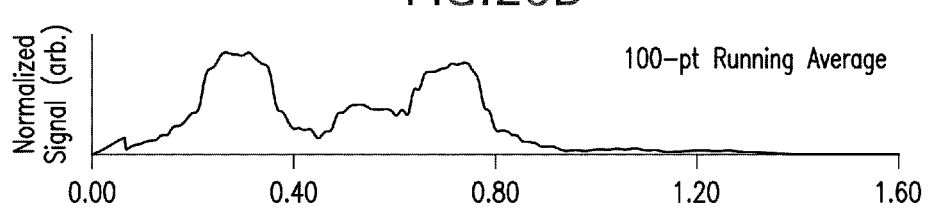

As shown in FIGS. 22-24, when the patient is stationary, ACC waveforms measured from the patient's chest (or, alternatively, belly) are sensitive to RR. This is because slight, breathing-induced motions of the patient's torso can be detected by the accelerometer. These figures show the time-domain IP waveforms (FIGS. 22A, 23A, 24A) and ACC waveforms (FIGS. 22B, 23B, 24B), both of which show pulses, lined up exactly in time, that correspond to individual breaths. The frequency-domain power spectrum (FIGS. 22C, 23C, 24C) show how the frequency components of these time-domain waveform are roughly equivalent, indicating both waveforms are sensitive to RR. This equivalency holds for normal breathing when the patient is on their back (FIG. 22); fast, shallow breathing when the patient is on their back (FIG. 23); and normal breathing when the patient is lying face down (FIG. 24). In all these cases both the ACC and IP waveforms can be processed collectively or independently to estimate RR. For collective processing, RRs may be determined from both waveforms, and then averaged together to generate a single value. Or a value may be determined from each waveform, and then subjected to a series of metrics (like those described above using $\alpha$, $\beta$, $\epsilon 1$, $\epsilon 2$) to determine if one or both of the calculated RRs is valid. Processing of the waveforms may involve simple pulse-counting algorithms that analyze time-domain waveforms, like the ones shown in FIGS. 22A, 22B, 23A, 23B, 24A, 24B, or more sophisticated spectral-analysis algorithms that analyze frequency-domain waveforms, like the ones shown in FIGS. 22C, 23C, 24C.

FIGS. 25 and 26 show how a filtering algorithm (FIG. 25) and rolling average (FIG. 26), when applied to a conventional power spectrum, facilitates determination of RR. The power spectrum in FIG. 25A (shown in the figure's top portion) is unprocessed, and features a collection of peaks positioned in three groupings near 0.3, 0.6, and 0.7 Hz. As described above, a low-pass smoothing filter based on a FIR function smoothes out these sharply varying features, resulting in a continuous spectrum that is relatively easy to analyze to determine a single frequency corresponding to RR. In this case, the smoothing filter is processing the power spectrum as if it were a time-domain waveform. FIG. 25B, for example, shows the spectrum after processing with a 5 Hz low-pass filter. Here, the individual peaks are mostly smoothed out, resulting in three primary peaks related to RR. Note that these peaks are not necessarily artifacts, and instead are due to physiological variations in the patient's breathing pattern. Progressively decreasing the filter cutoff removes more and more of the features that result in sharply varying peaks in the frequency spectrum. Ultimately when a 0.5 Hz filter is used, this results in a single, broad peak that lacks the definition to accurately determine RR. As described with reference to FIGS. 20F and 21F, the ideal smoothing filter has a cutoff of about 4 Hz.

FIG. 26 shows an alternate embodiment of the invention wherein a rolling average is used in place of the smoothing filter described above with reference to FIG. 25. Here, the rolling average is gradually increased from 0 points (FIG. 26A, at the top of the page) to 100 points. When the average is increased above about 20 points the features in the frequency spectrum begin to blend together to form a well-defined peak that can be easily analyzed using the peak-finding algorithm referenced above.

Referring to FIGS. 27 and 28, the number of time-domain samples used to calculate an associated Fourier Transform and power spectrum will have a significant influence on the resolution of the power spectrum. In general, increasing the number of time-domain samples will increase resolution in the power spectrum. According to this invention, the frequency-domain resolution can be arbitrarily increased by adding constant values to the time-domain ACC and IP waveform. In this technique, typically called 'zero padding', the constant values are typically 0, or alternatively a constant value.

Both FIGS. 27 and 28 show a time-domain IP waveform (FIGS. 27A and 28A, shown at the top of the page) along with associated power spectra calculated, respectively, using 1000 points (FIGS. 27B, 28B), 500 points (FIG. 27C, 28C), and 250 points (FIG. 27D, 28D). The IP waveform for this figure was sampled at 25 Hz, and thus the time-domain markers that correspond to the above-mentioned points are indicated by a light gray circle (1000 points), a dark gray circle (500 points), and a black circle (250 points). As shown in FIGS. 27B, 28B, 27C, 28C, power spectra determined with both 1000-point and 500-point Fourier Transforms feature roughly the same frequency profile, with, as expected, the 1000-point spectra showing relatively greater resolution. Power spectra calculated from the 250-point Fourier Transform show one or more very broad peaks, and, importantly, undergo a frequency shift which trends toward higher frequencies for the dominant peak. Such a frequency shift will result in an erroneous value for the eventual RR. For this reason, it is preferred that the Fourier Transform calculation use a minimum of 500 points, which corresponds to 10 seconds of data sampled at 50 Hz for the time-domain ACC and IP waveforms. The ideal number of points for this calculation is about 750, which at 50 Hz can be achieved in 15 seconds. Additionally, the frequency-domain data shown in FIGS. 27 and 28 was calculated with substantially fewer time-domain samples than that used for all previous figures (e.g. FIGS. 20, 21; Fourier Transforms for these figures were calculated with approximately 5000 points).

Figure 20F:
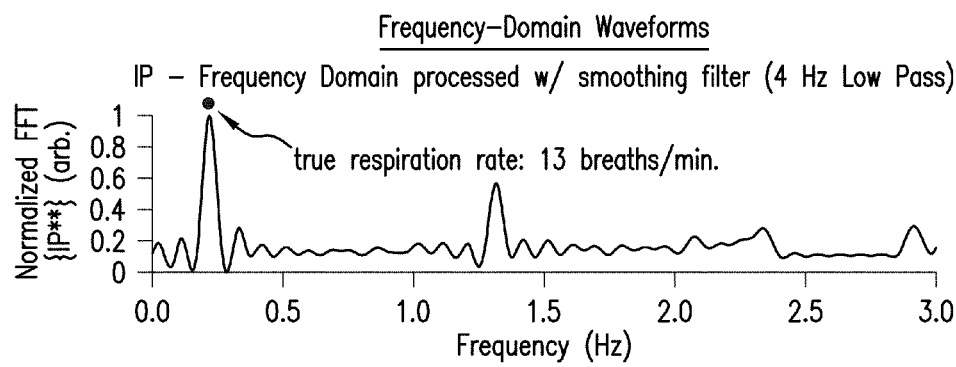
Figure 21F:
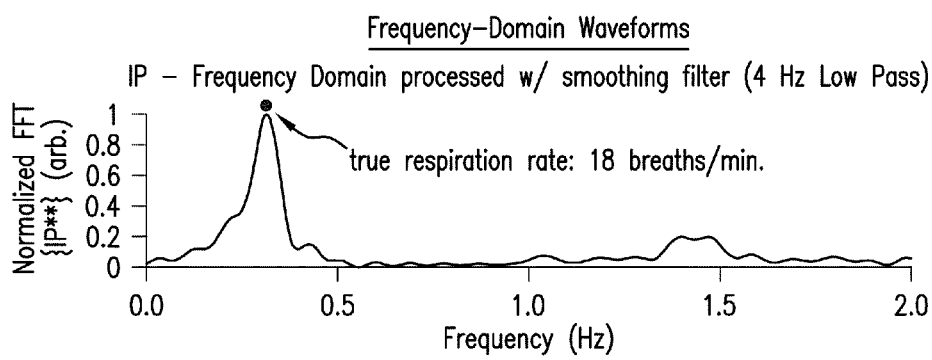

This results in a relatively low-resolution power spectrum that may not need the additional 4 Hz smoothing filter, indicated above with reference to FIGS. 20F and 21F. Here, the smoothing filter is essentially artificially applied due to the relatively low resolution of the power spectra.

Processing ACC Waveforms to Determine Posture

In addition to activity level, as described above and indicated in FIGS. 21-24, a patient's posture can influence how the above-described system generates alarms/alerts from RR, cNIBP, and other vital signs. For example, the alarms/alerts related to both RR and cNIBP may vary depending on whether the patient is lying down or standing up. FIG. 29 indicates how the body-worn monitor can determine motion-related parameters (e.g. degree of motion, posture, and activity level) from a patient 410 using time-dependent ACC waveforms continuously generated from the three accelerometers 412, 413, 414 worn, respectively, on the patient's chest, bicep, and wrist. The height of the patient's arm can affect the cNIBP measurement, as blood pressure can vary significantly due to hydrostatic forces induced by changes in arm height. Moreover, this phenomenon can be detected and exploited to calibrate the cNIBP measurement, as described in detail in the above-referenced patent applications, the contents of which have been previously incorporated by reference. As described in these documents, arm height can be determined using DC signals from the accelerometers 413, 414 disposed, respectively, on the patient's bicep and wrist. Posture, in contrast, can be exclusively determined by the accelerometer 412 worn on the patient's chest. An algorithm operating on the wrist-worn transceiver extracts DC values from waveforms measured from this accelerometer and processes them with an algorithm described below to determine posture.

Specifically, torso posture is determined for a patient 410 using angles determined between the measured gravitational vector and the axes of a torso coordinate space 411. The axes of this space 411 are defined in a three-dimensional Euclidean space where $\vec{R}_{CV}$ is the vertical axis, $\vec{R}_{CH}$ is the horizontal axis, and $\vec{R}_{CN}$ is the normal axis. These axes must be identified relative to a 'chest accelerometer coordinate space' before the patient's posture can be determined.

The first step in determining a patient's posture is to identify alignment of $\vec{R}_{CV}$ in the i chest accelerometer coordinate space. This can be determined in either of two approaches. In the first approach, $\vec{R}_{CV}$ is assumed based on a typical alignment of the body-worn monitor i relative to the patient. During a manufacturing process, these parameters are then pre-programmed into firmware operating on the wrist-worn transceiver. In this procedure it is assumed that accelerometers within the body-worn monitor are applied to each patient with essentially the same configuration. In the second approach, $\vec{R}_{CV}$ is identified on a patient-specific basis. Here, an algorithm operating on the wrist-worn transceiver prompts the patient (using, e.g., video instruction operating on the wrist-worn transceiver, or audio instructions transmitted through a speaker) to assume a known position with respect to gravity (e.g., standing upright with arms pointed straight down). The algorithm then calculates $\vec{R}_{CV}$ from DC values corresponding to the x, y, and z axes of the chest accelerometer while the patient is in this position. This case, however, still requires knowledge of which arm (left or right) the monitor is worn on, as the chest accelerometer coordinate space can be rotated by 180 degrees depending on this orientation. A medical professional applying the monitor can enter this information using the GUI, described above. This potential for dual-arm attachment requires a set of two pre-determined vertical and normal vectors which are interchangeable depending on the monitor's location. Instead of manually entering this information, the arm on which the monitor is worn can be easily determined following attachment using measured values from the chest accelerometer values, with the assumption that $\vec{R}_{CV}$ is not orthogonal to the gravity vector. i The second step in the procedure is to identify the alignment of $\vec{R}_{CN}$ in the chest accelerometer coordinate space. The monitor determines this vector in the same way it determines $\vec{R}_{CV}$ using one of two approaches. In the first approach the monitor assumes a typical alignment of the chest-worn accelerometer on the patient. In the second approach, the alignment is identified by prompting the patient to assume a known position with respect to gravity. The monitor then calculates $\vec{R}_{CN}$ from the DC values of the time-dependent ACC waveform.

The third step in the procedure is to identify the alignment of $\vec{R}_{CH}$ in the chest accelerometer coordinate space. This vector is typically determined from the vector cross product of $\vec{R}_{CV}$ and $\vec{R}_{CN}$, or it can be assumed based on the typical alignment of the accelerometer on the patient, as described above.

A patient's posture is determined using the coordinate system described above and in FIG. 29, along with a gravitational vector $\vec{R}_G$ that extends normal from the patient's chest. The angle between $\vec{R}_{CV}$ and $\vec{R}_G$ is given by Eq. 20:

$$\theta_{VG}[n] = \arccos\left(\frac{\vec{R}_G[n] \cdot \vec{R}_{CV}}{\|\vec{R}_G[n]\|\|\vec{R}_{CV}\|}\right) \quad (20)$$

where the dot product of the two vectors is defined as:

$$\vec{R}_G[n] \cdot \vec{R}_{CV} = (y_{Cx}[n] \times r_{CVx}) + (y_{Cy}[n] \times r_{CVy}) + (y_{Cz}[n] \times r_{CVz}) \quad (21)$$

The definition of the norms of $\vec{R}_G$ and $\vec{R}_{CV}$ are given by Eqs. 22 and 23:

$$\|\vec{R}_G[n]\| = \sqrt{(y_{Cx}[n])^2 + (y_{Cy}[n])^2 + (y_{Cz}[n])^2} \quad (22)$$

$$\|\vec{R}_{CV}\| = \sqrt{(r_{CVx})^2 + (r_{CVy})^2 + (r_{CVz})^2} \quad (23)$$

As indicated in Eq. 24, the monitor compares the vertical angle $\theta_{VG}$ to a threshold angle to determine whether the patient is vertical (i.e. standing upright) or lying down:

if $\theta_{VG} \leq 45°$ then Torso State=0, the patient is upright (24)

If the condition in Eq. 24 is met the patient is assumed to be upright, and their torso state, which is a numerical value equated to the patient's posture, is equal to 0. The patient is assumed to be lying down if the condition in equation (5) is not met, i.e. $\theta_{VG} > 45$ degrees. Their lying position is then determined from angles separating the two remaining vectors, as defined below.

The angle $\theta_{NG}$ between $\vec{R}_{CN}$ and $\vec{R}_G$ determines if the patient is lying in the supine position (chest up), prone position (chest down), or on their side. Based on either an assumed orientation or a patient-specific calibration procedure, as described above, the alignment of $\vec{R}_{CN}$ is given by Eq. 25, where i, j, k represent the unit vectors of the x, y, and z axes of the chest accelerometer coordinate space respectively:

$$\vec{R}_{CN} = r_{CNx}\hat{i} + r_{CNy}\hat{j} + r_{CNz}\hat{k} \quad (25)$$

The angle between $\vec{R}_{CN}$ and $\vec{R}_G$ determined from DC values extracted from the chest ACC waveform is given by Eq. 26:

$$\theta_{NG}[n] = \arccos\left(\frac{\vec{R}_G[n] \cdot \vec{R}_{CN}}{\|\vec{R}_G[n]\|\|\vec{R}_{CN}\|}\right) \quad (26)$$

The body-worn monitor determines the normal angle $\theta_{NG}$ and then compares it to a set of predetermined threshold angles to determine which position in which the patient is lying, as shown in Eq. 27:

if $\theta_{NG} \leq 35°$ then Torso State=1, the patient is supine if $\theta_{NG} \geq 135°$ then Torso State=2, the patient is prone (27)

If the conditions in Eq. 27 are not met then the patient is assumed to be lying on their side. Whether they are lying on their right or left side is determined from the angle calculated between the horizontal torso vector and measured gravitational vectors, as described above.

The alignment of $\vec{R}_{CH}$ is determined using either an assumed orientation, or from the vector cross-product of $\vec{R}_{CV}$ and $\vec{R}_{CN}$ as given by Eq. 28, where i, j, k represent the unit vectors of the x, y, and z axes of the accelerometer coordinate space respectively. Note that the orientation of the calculated vector is dependent on the order of the vectors in the operation. The order below defines the horizontal axis as positive towards the right side of the patient's body.

$$\vec{R}_{CH} = r_{CVx}\hat{i} + r_{CVy}\hat{j} + r_{CVz}\hat{k} = \vec{R}_{CV} \times \vec{R}_{CN} \quad (28)$$

The angle $\theta_{HG}$ between $\vec{R}_{CH}$ and $\vec{R}_G$ is determined using Eq. 29:

$$\theta_{HG}[n] = \arccos\left(\frac{\vec{R}_G[n] \cdot \vec{R}_{CH}}{\|\vec{R}_G[n]\|\|\vec{R}_{CH}\|}\right) \quad (29)$$

The monitor compares this angle to a set of predetermined threshold angles to determine if the patient is lying on their right or left side, as given by Eq. 30:

if $\theta_{HG} \geq 90°$ then Torso State=3, the patient is on their right side if $\theta_{NG} < 90°$ then Torso State=4, the patient is on their left side (30)

Table 1 describes each of the above-described postures, along with a corresponding numerical torso state used to render, e.g., a particular icon on a remote computer:

TABLE 1 postures and their corresponding torso states

| Posture | Torso State |
| --- | --- |
| standing upright | 0 |
| supine: lying on back | 1 |
| prone: lying on chest | 2 |
| lying on right side | 3 |
| lying on left side | 4 |
| undetermined posture | 5 |

FIGS. 30A and 30B show, respectively, graphs of time-dependent ACC waveforms measured along the x, y, and z-axes (FIG. 30A), and the torso states (i.e. postures; FIG. 30B) determined from these waveforms for a moving patient, as described above. As the patient moves, the DC values of the ACC waveforms measured by the chest accelerometer vary accordingly, as shown in FIG. 30A. The body-worn monitor processes these values as described above to continually determine $\vec{R}_G$ and the various quantized torso states for the patient, as shown in FIG. 30B. The torso states yield the patient's posture as defined in Table 1. For this study the patient rapidly alternated between standing, lying on their back, chest, right side, and left side within a time period of about 160 seconds. As described above, different alarm/alert conditions (e.g. threshold values) for vital signs can be assigned to each of these postures, or the specific posture itself may result in an alarm/alert. Additionally, the time-dependent properties of the graph can be analyzed (e.g. changes in the torso states can be counted) to determine, for example, how often the patient moves in their hospital bed. This number can then be equated to various metrics, such as a 'bed sore index' indicating a patient that is so stationary in their bed that lesions may result. Such a state could then be used to trigger an alarm/alert to the supervising medical professional.

Hardware for Measuring RR

FIGS. 4A and 4B show how the body-worn monitor 100 described above attaches to a patient 70 to measure RR, cNIBP, and other vital signs. These figures show two configurations of the system: FIG. 4A shows the system used during the indexing portion of the Composite Technique, and includes a pneumatic, cuff-based system 85, while FIG. 4B shows the system used for subsequent RR and cNIBP measurements. The indexing measurement typically takes about 60 seconds, and is typically performed once every 4 hours. Once the indexing measurement is complete the cuff-based system 85 is typically removed from the patient. The remainder of the time the monitor 100 performs the RR, HR, SpO2 and cNIBP measurements.

The body-worn monitor 100 features a wrist-worn transceiver 72, described in more detail in FIG. 5, featuring a touch panel interface 73 that displays RR and other vital signs. A wrist strap 90 affixes the transceiver 72 to the patient's wrist like a conventional wristwatch. A flexible cable 92 connects the transceiver 72 to an optical sensor 94 that wraps around the base of the patient's thumb. During a measurement, the optical sensor 94 generates a time-dependent PPG waveform which is processed along with an ECG to measure cNIBP, SpO2, and, in some applications, RR. To determine ACC waveforms the body-worn monitor 100 features three separate accelerometers located at different portions on the patient's arm and chest. The first accelerometer is surface-mounted on a circuit board in the wrist-worn transceiver 72 and measures signals associated with movement of the patient's wrist. As described above, this motion can also be indicative of that originating from the patient's fingers, which will affect the SpO2 measurement. The second accelerometer is included in a small bulkhead portion 96 included along the span of the cable 82. During a measurement, a small piece of disposable tape, similar in size to a conventional bandaid, affixes the bulkhead portion 96 to the patient's arm. In this way the bulkhead portion 96 serves two purposes: 1) it measures a time-dependent ACC waveform from the mid-portion of the patient's arm, thereby allowing their posture and arm height to be determined as described in detail above; and 2) it secures the cable 82 to the patient's arm to increase comfort and performance of the body-worn monitor 100, particularly when the patient is ambulatory. The third accelerometer is mounted in the sensor module 74 that connects through cables 80a-c to ECG electrodes 78a-c. As described in detail above, this accelerometer, which can also be mounted closer to the patient's belly, measures respiration-induced motion of the patient's chest and belly. These signals are then digitized, transmitted through the cable 82 to the wrist-worn transceiver 72, where they are processed with an algorithm as described above to determine RR.

The cuff-based module 85 features a pneumatic system 76 that includes a pump, valve, pressure fittings, pressure sensor, manifold, analog-to-digital converter, microcontroller, and rechargeable Li:ion battery. During an indexing measurement, the pneumatic system 76 inflates a disposable cuff 84 and performs two measurements according to the Composite Technique: 1) it performs an inflation-based measurement of oscillometry to determine values for SYS, DIA, and MAP; and 2) it determines a patient-specific relationship between PTT and MAP. These measurements are described in detail in the above-referenced patent applications entitled: 'VITAL SIGN MONITOR FOR MEASURING BLOOD PRESSURE USING OPTICAL, ELECTRICAL, AND PRESSURE WAVEFORMS' (U.S. Ser. No. 12/138,194; filed Jun. 12, 2008) and 'BODY-WORN SYSTEM FOR MEASURING CONTINUOUS NON-INVASIVE BLOOD PRESSURE (cNIBP)' (U.S. Ser. No. 12/650,354; filed Nov. 15, 2009), the contents of which have been previously incorporated herein by reference.

The cuff 84 within the cuff-based pneumatic system 85 is typically disposable and features an internal, airtight bladder that wraps around the patient's bicep to deliver a uniform pressure field. During the indexing measurement, pressure values are digitized by the internal analog-to-digital converter, and sent through a cable 86 according to a CAN protocol, along with SYS, DIA, and MAP blood pressures, to the wrist-worn transceiver 72 for processing as described above. Once the cuff-based measurement is complete, the cuff-based module 85 is removed from the patient's arm and the cable 86 is disconnected from the wrist-worn transceiver 72. cNIBP is then determined using PTT, as described in detail above.

To determine an ECG, the body-worn monitor 100 features a small-scale, three-lead ECG circuit integrated directly into the sensor module 74 that terminates an ECG cable 82. The ECG circuit features an integrated circuit that collects electrical signals from three chest-worn ECG electrodes 78a-c connected through cables 80a-c. As described above, the ECG electrodes 78a-c are typically disposed in a conventional Einthoven's Triangle configuration, which is a triangle-like orientation of the electrodes 78a-c on the patient's chest that features three unique ECG vectors. From these electrical signals the ECG circuit determines up to three ECG waveforms, which are digitized using an analog-to-digital converter mounted proximal to the ECG circuit, and sent through the cable 82 to the wrist-worn transceiver 72 according to the CAN protocol. There, the ECG and PPG waveforms are processed to determine the patient's blood pressure. Heart rate and RR are determined directly from the ECG waveform using known algorithms, such as those described above. More sophisticated ECG circuits (e.g. five and twelve-lead systems) can plug into the wrist-worn transceiver to replace the three-lead system shown in FIGS. 4A and 4B.

FIG. 5 shows a close-up view of the wrist-worn transceiver 72. As described above, it attaches to the patient's wrist using a flexible strap 90 which threads through two D-ring openings in a plastic housing 106. The transceiver 72 features a touch-panel display 120 that renders a GUI 73 which is altered depending on the viewer (typically the patient or a medical professional). Specifically, the transceiver 72 includes a small-scale infrared barcode scanner 102 that, during use, can scan a barcode worn on a badge of a medical professional. The barcode indicates to the transceiver's software that, for example, a nurse or doctor is viewing the user interface. In response, the GUI 73 displays vital sign data and other medical diagnostic information appropriate for medical professionals. Using this GUI 73, the nurse or doctor, for example, can view the vital sign information, set alarm parameters, and enter information about the patient (e.g. their demographic information, medication, or medical condition). The nurse can press a button on the GUI 73 indicating that these operations are complete. At this point, the display 120 renders an interface that is more appropriate to the patient, such as time of day and battery power.

The transceiver 72 features three CAN connectors 104a-c on the side of its upper portion, each which supports the CAN protocol and wiring schematics, and relays digitized data to the internal CPU. Digital signals that pass through the CAN connectors include a header that indicates the specific signal (e.g. ECG, ACC, or pressure waveform from the cuff-based module) and the sensor from which the signal originated. This allows the CPU to easily interpret signals that arrive through the CAN connectors 104a-c, such as those described above corresponding to RR, and means that these connectors are not associated with a specific cable. Any cable connecting to the transceiver can be plugged into any connector 104a-c. As shown in FIG. 4A, the first connector 104a receives the cable 82 that transports a digitized ECG waveform determined from the ECG circuit and electrodes, and digitized ACC waveforms measured by accelerometers in the sensor module 74 and the bulkhead portion 96 associated with the ECG cable 82.

The second CAN connector 104b shown in FIG. 5 receives the cable 86 that connects to the pneumatic cuff-based system 85 used for the pressure-dependent indexing measurement (shown in FIG. 4A). This connector 104b receives a time-dependent pressure waveform delivered by the pneumatic system 85 to the patient's arm, along with values for SYS, DIA, and MAP values determined during the indexing measurement. The cable 86 unplugs from the connector 104b once the indexing measurement is complete, and is plugged back in after approximately four hours for another indexing measurement.

The final CAN connector 104c can be used for an ancillary device, e.g. a glucometer, infusion pump, body-worn insulin pump, ventilator, or et-CO2 measurement system. As described above, digital information generated by these systems will include a header that indicates their origin so that the CPU can process them accordingly.

The transceiver includes a speaker 101 that allows a medical professional to communicate with the patient using a voice over Internet protocol (VoIP). For example, using the speaker 101 the medical professional could query the patient from a central nursing station or mobile phone connected to a wireless, Internet-based network within the hospital. Or the medical professional could wear a separate transceiver similar to the shown in FIG. 5, and use this as a communication device. In this application, the transceiver 72 worn by the patient functions much like a conventional cellular telephone or 'walkie talkie': it can be used for voice communications with the medical professional and can additionally relay information describing the patient's vital signs and motion. The speaker can also enunciate pre-programmed messages to the patient, such as those used to calibrate the chest-worn accelerometers for a posture calculation, as described above.

Other Embodiments of the Invention

RR can also be calculated using a combination of ACC, ECG, PPG, IP, and other signals using algorithms that differ from those described above. For example, these signals can be processed with an averaging algorithm, such as one using a weighted average, to determine a single waveform that can then be processed to determine RR. Some of these measurement techniques are described, for example, in the following patent application, the contents of which are incorporated herein by reference: 'BODY-WORN MONITOR FOR MEASURING RESPIRATION RATE' (U.S. Ser. No. 12/559,419; filed Sep. 14, 2009). Or the ACC waveform can be used alone, without being integrated in an adaptive filtering algorithm, to determine RR without relying on IP. In this case the ACC waveform is filtered with a simple bandpass filter, e.g. a finite impulse response filter, with a set passband (e.g. 0.01→5 Hz). Similarly, multiple ACC waveforms, such as those measured along axes (e.g. the x or y-axes) orthogonal to the vector normal to the patient's chest (i.e. the z-axis), can be processed with or without adaptive filtering to determine RR. In this case the waveforms may be averaged together with a weighted average to generate a single waveform, which is then filtered, derivatized, and signal processed as described above to determine RR. Similarly, envelopes associated with the ECG and PPG waveforms can be processed in a similar manner to determine RR. In still other embodiments, other sensors, such as detectors for ultra wide-band radar or acoustic microphones, can detect signals indicative of RR and used with ACC or IP waveforms and the adaptive filtering approach described above to determine RR. Here, the alternative sensors are typically used to replace measurement of the IP waveform, although they can also be used to replace measurement of the ACC waveform. An acoustic sensor suitable for this application is described, for example, in the following co-pending patent application, the contents of which are incorporated herein by reference: DEVICE FOR DETERMINING RESPIRATORY RATE AND OTHER VITAL SIGNS (U.S. Ser. No. 12/171,886; filed Jul. 12, 2008).

In addition to those methods described above, the body-worn monitor can use a number of additional methods to calculate blood pressure and other properties from the optical and electrical waveforms. These are described in the following co-pending patent applications, the contents of which are incorporated herein by reference: 1) CUFFLESS BLOOD-PRESSURE MONITOR AND ACCOMPANYING WIRELESS, INTERNET-BASED SYSTEM (U.S. Ser. No. 10/709, 015; filed Apr. 7, 2004); 2) CUFFLESS SYSTEM FOR MEASURING BLOOD PRESSURE (U.S. Ser. No. 10/709, 014; filed Apr. 7, 2004); 3) CUFFLESS BLOOD PRESSURE MONITOR AND ACCOMPANYING WEB SERVICES INTERFACE (U.S. Ser. No. 10/810,237; filed Mar. 26, 2004); 4) VITAL SIGN MONITOR FOR ATHLETIC APPLICATIONS (U.S. Ser. No.; filed Sep. 13, 2004); 5) CUFFLESS BLOOD PRESSURE MONITOR AND ACCOMPANYING WIRELESS MOBILE DEVICE (U.S. Ser. No. 10/967,511; filed Oct. 18, 2004); 6) BLOOD PRESSURE MONITORING DEVICE FEATURING A CALIBRATION-BASED ANALYSIS (U.S. Ser. No. 10/967,610; filed Oct. 18, 2004); 7) PERSONAL COMPUTER-BASED VITAL SIGN MONITOR (U.S. Ser. No. 10/906,342; filed Feb. 15, 2005); 8) PATCH SENSOR FOR MEASURING BLOOD PRESSURE WITHOUT A CUFF (U.S. Ser. No. 10/906,315; filed Feb. 14, 2005); 9) PATCH SENSOR FOR MEASURING VITAL SIGNS (U.S. Ser. No. 11/160,957; filed Jul. 18, 2005); 10) WIRELESS, INTERNET-BASED SYSTEM FOR MEASURING VITAL SIGNS FROM A PLURALITY OF PATIENTS IN A HOSPITAL OR MEDICAL CLINIC (U.S. Ser. No. 11/162,719; filed Sep. 9, 2005); 11) HAND-HELD MONITOR FOR MEASURING VITAL SIGNS (U.S. Ser. No. 11/162,742; filed Sep. 21, 2005); 12) CHEST STRAP FOR MEASURING VITAL SIGNS (U.S. Ser. No. 11/306, 243; filed Dec. 20, 2005); 13) SYSTEM FOR MEASURING VITAL SIGNS USING AN OPTICAL MODULE FEATURING A GREEN LIGHT SOURCE (U.S. Ser. No. 11/307,375; filed Feb. 3, 2006); 14) BILATERAL DEVICE, SYSTEM AND METHOD FOR MONITORING VITAL SIGNS (U.S. Ser. No. 11/420,281; filed May 25, 2006); 15) SYSTEM FOR MEASURING VITAL SIGNS USING BILATERAL PULSE TRANSIT TIME (U.S. Ser. No. 11/420,652; filed May 26, 2006); 16) BLOOD PRESSURE MONITOR (U.S. Ser. No. 11/530,076; filed Sep. 8, 2006); 17) TWO-PART PATCH SENSOR FOR MONITORING VITAL SIGNS (U.S. Ser. No. 11/558,538; filed Nov. 10, 2006); and, 18) MONITOR FOR MEASURING VITAL SIGNS AND RENDERING VIDEO IMAGES (U.S. Ser. No. 11/682,177; filed Mar. 5, 2007).

Other embodiments are also within the scope of the invention. For example, other measurement techniques, such as conventional oscillometry measured during deflation, can be used to determine SYS for the above-described algorithms. Additionally, processing units and probes for measuring pulse oximetry similar to those described above can be modified and worn on other portions of the patient's body. For example, optical sensors with finger-ring configurations can be worn on fingers other than the thumb. Or they can be modified to attach to other conventional sites for measuring SpO2, such as the ear, forehead, and bridge of the nose. In these embodiments the processing unit can be worn in places other than the wrist, such as around the neck (and supported, e.g., by a lanyard) or on the patient's waist (supported, e.g., by a clip that attaches to the patient's belt). In still other embodiments the probe and processing unit are integrated into a single unit.

In other embodiments, a set of body-worn monitors can continuously monitor a group of patients, wherein each patient in the group wears a body-worn monitor similar to those described herein. Additionally, each body-worn monitor can be augmented with a location sensor. The location sensor includes a wireless component and a location-processing component that receives a signal from the wireless component and processes it to determine a physical location of the patient. A processing component (similar to that described above) determines from the time-dependent waveforms at least one vital sign, one motion parameter, and an alarm parameter calculated from the combination of this information. A wireless transceiver transmits the vital sign, motion parameter, location of the patient, and alarm parameter through a wireless system. A remote computer system featuring a display and an interface to the wireless system receives the information and displays it on a user interface for each patient in the group.

In embodiments, the interface rendered on the display at the central nursing station features a field that displays a map corresponding to an area with multiple sections. Each section corresponds to the location of the patient and includes, e.g., the patient's vital signs, motion parameter, and alarm parameter. For example, the field can display a map corresponding to an area of a hospital (e.g. a hospital bay or emergency room), with each section corresponding to a specific bed, chair, or general location in the area. Typically the display renders graphical icons corresponding to the motion and alarm parameters for each patient in the group. In other embodiments, the body-worn monitor includes a graphical display that renders these parameters directly on the patient.

Typically the location sensor and the wireless transceiver operate on a common wireless system, e.g. a wireless system based on 802.11 (i.e. 'WiFi'), 802.15.4 (i.e. 'Bluetooth'), or cellular (e.g. CDMA, GSM) protocols. In this case a location is determined by processing the wireless signal with one or more algorithms known in the art. These include, for example, triangulating signals received from at least three different base stations, or simply estimating a location based on signal strength and proximity to a particular base station. In still other embodiments the location sensor includes a conventional global positioning system (GPS) that processes signals from orbiting satellites to determine patient's position.

The body-worn monitor can include a first voice interface, and the remote computer can include a second voice interface that integrates with the first voice interface. The location sensor, wireless transceiver, and first and second voice interfaces can all operate on a common wireless system, such as one of the above-described systems based on 802.11 or cellular protocols. The remote computer, for example, can be a monitor that is essentially identical to the monitor worn by the patient, and can be carried or worn by a medical professional. In this case the monitor associated with the medical professional features a GUI wherein the user can select to display information (e.g. vital signs, location, and alarms) corresponding to a particular patient. This monitor can also include a voice interface so the medical professional can communicate directly with the patient.

In other embodiments, the electrodes connect to the ECG circuit using a wireless interface. Here, each electrode includes a small, battery-powered microprocessor, radio, and analog-to-digital converter. The analog-to-digital converter converts an analog signal measured by the electrode into a digital signal. The radio then sends the digital signal to the ECG circuit, which processes signals from multiple electrodes using a differential amplifier to determine both ECG and IP waveforms as described above.

FIGS. 3A, 3B show yet another alternate embodiment of the invention wherein a sensor module 25 attaches to the belly of a patient 10 using an electrode 24 normally attached to the lower left-hand portion of the patient's torso. Specifically, the sensor module 25 includes a connector 253 featuring an opening that receives the metal snap or rivet present on most disposable ECG electrodes. Connecting the connector 253 to the electrode's rivet holds the sensor module 25 in place. This configuration reduces the number of cables in the body-worn monitor, and additionally secures an accelerometer 12 to the patient's belly. This is typically the part of their torso that undergoes the greatest motion during respiration, and thus generates ACC waveforms with the highest possible signal-to-noise ratio. Also contained within the sensor module 25 are the ECG circuit 26, the IP circuit 27, microprocessor 33, and a temperature sensor 34.

To measure IP and ECG waveforms, the sensor module 25 connects through cables to electrodes 20, 22 attached, respectively, to the upper right-hand and left-hand portions of the patient's torso. This system measures RR using the peak counting, adaptive filtering, and FFT-based approaches described above, and has the additional advantage of measuring a relatively large ACC signals indicating respiration-induced motions of the patient's belly. As described above, these signals are typically generated by the z-axis of the accelerometer 12, which is normal to the patient's torso. ACC signals along the x and y-axes can be additionally processed to determine the patient's posture and activity level, as described above. Once RR and these motion-related properties are measured, a transceiver in the sensor module (not shown in the figure) transmits them in the form of a digital data stream through a cable to the wrist-worn transceiver for further processing.

Still other embodiments are within the scope of the following claims.

What is claimed is:

1. A method for measuring respiratory rate from a patient, comprising the following steps:
    (a) measuring a time-dependent impedance pneumography signal from the patient with an impedance pneumography sensor connected to at least two electrodes positioned noninvasively on the patient's torso, the impedance pneumography signal representing a time-dependent capacitance change in the patient's torso;
    (b) measuring at least one time-dependent motion signal with a motion sensor positioned noninvasively on the patient's torso, the at least one motion signal corresponding to motion of a portion of the patient's body to which the motion sensor is attached;
    (c) transmitting the impedance pneumography signal and the at least one motion signal to a processing system comprising a microprocessor and processing the impedance pneumography signal and the at least one motion signal using the processing system to determine the patient's respiratory rate, the processing steps comprising:
        (i) transforming the time-dependent impedance pneumography signal into a frequency-dependent impedance pneumography spectrum;
        (ii) transforming the time-dependent motion signal into a frequency-dependent motion spectrum;
        (iii) determining motion components from the frequency-dependent motion spectrum that correspond to the patient's motion;
        (iv) removing the motion components, or components calculated therefrom, from the frequency-dependent impedance pneumography spectrum to generate a processed frequency-dependent impedance pneumography spectrum; and
        (v) analyzing the processed frequency-dependent impedance pneumography spectrum to determine the patient's respiratory rate.

2. The method of claim 1, wherein step (c)(i) comprises taking a Fourier Transform of the time-dependent impedance pneumography signal.

3. The method of claim 2, wherein step (c)(i) comprises calculating a power spectrum of the time-dependent impedance pneumography signal.

4. The method of claim 1, wherein step (c)(ii) comprises calculating a Fourier Transform of the time-dependent motion signal.

5. The method of claim 4, wherein step (c)(ii) comprises calculating a power spectrum of the time-dependent motion signal.

6. The method of claim 1, wherein step (c)(iii) comprises calculating a peak in the frequency-dependent motion spectrum, the peak corresponding to the motion components.

7. The method of claim 6, further comprising processing the peak in the frequency-dependent motion spectrum to determine a digital filter.

8. The method of claim 7, further comprising determining a passband for the digital filter by processing the peak in the frequency-dependent motion spectrum, the passband configured to pass frequency components lying therein.

9. The method of claim 8, wherein step (c)(iv) further comprising processing the frequency-dependent impedance pneumography spectrum with the digital filter to remove motion components and generate the processed frequency-dependent impedance pneumography spectrum.

10. The method of claim 6, wherein step (c)(iv) comprises subtracting the motion components from the frequency-dependent impedance pneumography spectrum to generate the processed frequency-dependent impedance pneumography spectrum.

11. The method of claim 6, wherein step (c)(iv) comprises dividing the motion components from the frequency-dependent impedance pneumography spectrum to generate the processed frequency-dependent impedance pneumography spectrum.

12. The method of claim 7, wherein step (c)(iv) further comprises processing the frequency-dependent impedance pneumography spectrum with a smoothing function after applying the digital filter to generate the processed frequency-dependent impedance pneumography spectrum.

13. The method of claim 7, wherein step (c)(iv) further comprises processing the frequency-dependent impedance pneumography spectrum with an averaging function after applying the digital filter to generate the processed frequency-dependent impedance pneumography spectrum.

14. The method of claim 7, wherein step (c)(v) further comprises analyzing the processed frequency-dependent impedance pneumography spectrum to determine a spectral peak, the spectral peak corresponding to the patient's respiratory rate.

15. The method of claim 1, wherein the motion sensor is an accelerometer.

16. The method of claim 15, wherein the accelerometer is configured to generate a unique motion waveform for each axis of a coordinate system.

17. The method of claim 16, further comprising processing each unique motion waveform to determine a posture corresponding to the patient.

18. The method of claim 17, further comprising generating an alarm if the patient's respiratory rate is greater than a first pre-determined threshold, or less than a second pre-determined threshold.

19. The method of claim 18, further comprising processing the patient's respiratory rate and the posture corresponding to the patient to generate the alarm.

* * * * *